US012575840B2

(12) United States Patent　　(10) Patent No.: US 12,575,840 B2

Doty et al.　　(45) Date of Patent: Mar. 17, 2026

(54) ANKLE JOINT SYSTEM AND RELATED METHODS

(71) Applicant: Vilex LLC, McMinnville, TN (US)

(72) Inventors: Jesse F. Doty, Hixson, TN (US); Brock L. Johnson, Draper, UT (US); Daniel Triplett, Smithfield, UT (US); James Robbins, Logan, UT (US); Weston Bowcutt, Hyrum, UT (US); Zachary Charles Christensen, Wellsville, UT (US); Nick Ashby, Logan, UT (US); Nathan William Erickson, Beaver Dam, UT (US)

(73) Assignee: Vilex LLC, McMinnville, TN (US)

( * ) Notice: Subject to any disclaimer, the term of this patent is extended or adjusted under 35 U.S.C. 154(b) by 0 days.

(21) Appl. No.: 18/769,305

(22) Filed: Jul. 10, 2024

(65) Prior Publication Data

US 2025/0017603 A1　　Jan. 16, 2025

Related U.S. Application Data

(60) Provisional application No. 63/525,806, filed on Jul. 10, 2023.

(51) Int. Cl.
　　*A61B 17/17*　　(2006.01)
　　*A61B 17/00*　　(2006.01)
(52) U.S. Cl.
　　CPC .................... *A61B 17/1775* (2016.11); *A61B 2017/00367* (2013.01)
(58) Field of Classification Search
　　CPC .......................... A61B 17/1775; A61B 17/164
　　See application file for complete search history.

(56) References Cited

U.S. PATENT DOCUMENTS

| 6,102,956 | A | 8/2000 | Kranz |
| 7,534,246 | B2 | 5/2009 | Reiley et al. |
| 8,034,054 | B2 | 10/2011 | Griggs |
| 8,128,627 | B2 | 3/2012 | Meng et al. |
| 8,133,226 | B2 | 3/2012 | Chou et al. |

(Continued)

FOREIGN PATENT DOCUMENTS

| CN | 109938799 A | 6/2019 |
| CN | 116269662 A | 6/2023 |

OTHER PUBLICATIONS

International Search Report and Written Opinion for PCT/US2024/037476 dated Oct. 25, 2024.

*Primary Examiner* — Andrew Yang
(74) *Attorney, Agent, or Firm* — Reed Smith LLP; Matthew P. Frederick; Jennifer C. Black

(57) ABSTRACT

Systems and related methods for preparing and treating damage in an ankle joint. The system may include one or more of a reamer, a surgical device, a tibial implant, a placement tool, and a talar implant. The reamer may prepare an intramedullary canal for implantation of an implant. The reamer may include a plurality of nested reamer elements that may be expanded into the intramedullary canal. The surgical device may include a housing containing the reamer and be configured to orient the reamer with the intramedullary canal. The tibial implant may include a plurality of stem components. The placement tool may be configured to combine the plurality of stem components. The talar implant may be configured to be implanted in a talus.

20 Claims, 34 Drawing Sheets

(56) References Cited

U.S. PATENT DOCUMENTS

| | | | |
|---|---|---|---|
| 8,496,658 | B2 | 7/2013 | Stoneburner et al. |
| 8,715,362 | B2 | 5/2014 | Reiley et al. |
| 9,125,695 | B2 | 9/2015 | Early et al. |
| 9,402,640 | B2 | 8/2016 | Reynolds et al. |
| 9,452,056 | B2 | 9/2016 | Early et al. |
| 9,539,044 | B2 | 1/2017 | Lian |
| 9,629,726 | B2 | 4/2017 | Reiley et al. |
| 10,117,685 | B2 | 11/2018 | Ehmke et al. |
| 10,426,494 | B2 | 10/2019 | Saltzman et al. |
| 10,456,179 | B2 | 10/2019 | Luna et al. |
| 10,667,850 | B2 | 6/2020 | Sweeney et al. |
| 10,743,999 | B2 | 8/2020 | Reiley |
| 10,772,733 | B2 | 9/2020 | Lintula et al. |
| 10,888,338 | B2 | 1/2021 | Lintula et al. |
| 11,141,283 | B2 | 10/2021 | Fonte et al. |
| 11,179,234 | B2 | 11/2021 | Dacosta et al. |
| 11,202,714 | B2 | 12/2021 | Oh et al. |
| 11,246,712 | B2 | 2/2022 | Williams et al. |
| 11,318,024 | B2 | 5/2022 | Petranto |
| 11,324,601 | B2 | 5/2022 | Kowalczyk et al. |
| 11,446,152 | B2 | 9/2022 | Reiley et al. |
| 11,617,642 | B2 | 4/2023 | Dacosta et al. |
| 11,911,281 | B2 | 2/2024 | Williams et al. |
| 2003/0109932 | A1 * | 6/2003 | Keynan ................ A61F 2/3601 623/23.26 |
| 2009/0222008 | A1 * | 9/2009 | Hogg ................ A61B 17/1617 606/80 |
| 2010/0094292 | A1 | 4/2010 | Parrott |
| 2012/0065638 | A1 | 3/2012 | Moore |
| 2022/0087693 | A1 | 3/2022 | Kubacki, III |
| 2022/0192817 | A1 | 6/2022 | Gill et al. |
| 2022/0387181 | A1 | 12/2022 | Reiley et al. |
| 2023/0190306 | A1 | 6/2023 | Kowalczyk et al. |
| 2023/0190481 | A1 | 6/2023 | Kowalczyk et al. |
| 2023/0240833 | A1 | 8/2023 | Dacosta et al. |

* cited by examiner

42

45

42

43

43

43

43

208

265

256

258

ANKLE JOINT SYSTEM AND RELATED METHODS

CROSS-REFERENCE TO RELATED APPLICATION

This application claims the benefit of priority to U.S. Provisional Application Ser. No. 63/525,806 filed Jul. 10, 2023, the entire disclosure of which is incorporated herein by reference.

FIELD OF THE INVENTION

The present disclosure relates to systems and methods for preparing and treating damage in an ankle joint.

BACKGROUND OF THE INVENTION

Ankle injuries, including fractures or damage resulting from arthritis, can be treated with total ankle replacement systems. Total ankle replacement requires significant instrumentation, including jigs, guides, reamers, multiple implants, and other devices, coupled with invasive access techniques to gain access to the implantation site. In order to place a superior tibial implant in the tibia at the correct orientation, access is obtained inferiorly through the channels drilled through the calcaneus and talus. This creates a generally linear path, through the drilled channels, to both prepare the inner tibia and position the implants in place. Current total ankle replacement and the techniques used to access the implantation site are therefore complex and invasive.

SUMMARY OF THE INVENTION

In embodiments, a system for insertion in a posterior direction into an insertion site of an ankle joint includes a track assembly, a shaft, and an expandable surgical device. The track assembly includes a first axis and sized and shaped for insertion into the insertion site in a posterior direction. The shaft is rotatably coupled to the track assembly and configured to rotate about a second axis that is generally perpendicular to and intersects the first axis, wherein the shaft is configured to expand in a superior direction along the second axis. The expandable surgical device is coupled to the shaft and configured to rotate with the shaft, the expandable surgical device including a first bone engagement segment and a second bone engagement segment coupled to the shaft and movably coupled to the first bone engagement segment. When in a collapsed state, the first bone engagement segment includes the second bone engagement segment nested within the first bone engagement segment, and further wherein the track assembly including the first bone engagement segment and the second bone engagement segment nested within the track assembly. The shaft and the first bone engagement segment and the second bone engagement segment are configured such that rotation of the shaft causes the first bone engagement segment and the second bone engagement segments to expand relative to one another in the superior direction from the track assembly from the collapsed state into an expanded state.

In embodiments, the expandable surgical device includes a first height in a collapsed state, and a second height in an expanded state that is greater than the first height, and a diameter along any portion of the expandable surgical device does not increase during expansion into the expanded state.

In embodiments, the second height is at least twice the first height. In embodiments, the track assembly includes a first gear, a second gear spaced from the first gear along the first axis, and a track coupled to the first gear and the second gear, such that rotation of the first gear causes the track to rotate about the second axis and the second gear to rotate about a third axis. In embodiments, the system includes a clutch coupled to the track assembly and the expandable surgical device.

In embodiments, the expandable surgical device includes a base coupled to the shaft and movably coupled to the first bone engagement segment, wherein the clutch is configured to transition between a) a locked position where the expandable surgical device rotates in the collapsed state, and b) an unlocked position where the base does not rotate and each of the first and second bone engagement segments are permitted to rotate, thereby advancing in the superior direction.

In embodiments, the clutch includes a first plurality of engagement elements, wherein the base includes a second plurality of engagement elements configured to engage the first plurality of engagement elements of the clutch. In embodiments, when in the locked position, the first plurality of engagement elements engage with the second plurality of engagement elements of the clutch such that the base does not rotate.

In embodiments, when the clutch is in the locked position, each of the first and second bone engagement segments are configured to threadably rotate relative to each other sequentially to expand the expandable surgical device along the superior direction. In embodiments, the expandable surgical device includes a superior bone engagement segment that is superior to all other bone engagement segments when in the expanded state, and further wherein the superior bone engagement segment is included and nested within an adjacent bone engagement segment.

In embodiments, the system includes a base, wherein the first bone engagement segment is threadably coupled to the base, and the second bone engagement segment is threadably coupled to the first bone engagement segment and wherein the expandable surgical device further includes a third bone engagement segment threadably coupled to the second bone engagement segment, a fourth bone engagement segment threadably coupled to the third bone engagement segment, and a superior bone engagement segment threadably coupled to the fourth bone engagement segment, wherein rotation of the shaft causes the superior bone engagement segment to rotate and expand in the superior direction relative to the fourth bone engagement segment, the third bone engagement segment, the second bone engagement segment, and the first bone engagement segment.

In embodiments, when in the expanded state, the superior bone engagement segment is positioned superior relative to the other bone engagement segments, the fourth bone engagement segment is positioned superior relative to the first bone engagement segment, the second bone engagement segment, and the third bone engagement segment, a second bone engagement segment is threadably coupled to the first bone engagement segment and the shaft, such that, the second bone engagement segment is movable relative to the first bone engagement segment in response to rotation of the shaft, a third bone engagement segment is threadably coupled to the second bone engagement segment and the shaft, such that, the third bone engagement segment is movable relative to the second bone engagement segment in response to rotation of the shaft, and a fourth bone engagement segment is threadably coupled to the third bone engagement segment and the shaft, such that, the fourth bone engagement segment is movable relative to the third bone engagement segment in response to rotation of the shaft.

In embodiments, the first bone engagement segment and second bone engagement segment each include an internal thread and an external thread, wherein the external thread of the first bone engagement segment threadably engages the internal thread of the second bone engagement segment. In embodiments, the expandable surgical device includes a stop element that is configured to inhibit further advancement of at least one of a first bone engagement segment and a second bone engagement segment in the superior direction beyond a certain expansion distance. In embodiments, the stop element is selected from one of a mechanical detent and a projection, and wherein the stop element is configured such that it blocks further rotation relative to an adjacent bone engagement segment.

In embodiments, each of a plurality of bone engagement segments includes a diameter that is equal to or greater than a diameter of a superior-most bone engagement segment. In embodiments, a diameter of the first bone engagement segment that is inferior to a second bone engagement segment is greater than a diameter of the second bone engagement segment. In embodiments, at least one of the first bone engagement segment and the second bone engagement segment include a cutting element. In embodiments, at least one of the first bone engagement segment and the second bone engagement segment include a beveled edge configured to cut bone. In embodiments, the expandable surgical device includes an external surface configured for bony ingrowth surface.

In embodiments, the expandable surgical device includes an external surface with depth indicators. In embodiments, the expandable surgical device includes a generally conical shape when in a fully expanded state. In embodiments, the expandable surgical device includes a generally cylindrical shape when in a fully expanded state. In embodiments, the shaft and the expandable surgical device are cannulated. In embodiments, at least one of the first bone engagement segment and second bone engagement segment include cutting flutes.

In embodiments, the system includes a power source configured to generate rotative motion to the track assembly. In embodiments, the power source is removably couplable and is selected from one of a drill and manual rotational force of the user. In embodiments, the track assembly is configured to disengage from the expandable surgical device and be decoupled therefrom. In embodiments, the expandable surgical device includes an expandable reamer, and the first bone engagement segment and second bone engagement segment include first and second reamer segments. In embodiments, the expandable surgical device includes a tibial implant configured for implantation in an interior portion of the tibia.

In embodiments, the tibial implant further includes a plurality of connectable bone engagement segments, wherein each connectable bone engagement segment is configured to selectively engage an adjacent bone engagement segment in the interior portion of the tibia. In embodiments, the system includes a distal implant configured to engage at least a talus bone, the distal implant includes a lower surface that engages talus bone and a superior surface configured to movably engage an inferior surface of the tibial implant.

In embodiments, a method for insertion in a posterior direction into an ankle joint having a tibia and a talus bone includes a track assembly, a shaft, a clutch, and an expandable surgical device. The track assembly includes a first axis that extends in a posterior direction when inserted into an insertion site a distal end of the tibia. The shaft rotatably coupled to the track assembly and configured to rotate about a second axis that is generally perpendicular to and intersects the first axis, wherein the shaft is configured to expand in a superior direction along the second axis. The clutch coupled to the track assembly, the clutch includes one or more engagement members. The expandable surgical device is coupled to the shaft and rotatable about the second axis, the expandable surgical device includes a base and one or more slots that are configured to selectively engage the one or more engagement members of the clutch so that the base is selectively rotatable about the second axis, and a plurality of bone engagement segments movably coupled to the base and each other, the expandable surgical device includes a collapsed state, where the bone engagement segments are concentrically coupled to each other, and an expanded state, where the bone engagement segments expand along the second axis, wherein selective rotation of the base causes the bone engagement segments to expand along the second axis from the collapsed state into the expanded state.

In embodiments, a method includes inserting an expandable surgical device in a collapsed state into an insertion site of an ankle via an anterior approach, and rotating the expandable surgical device about an axis generally coincident with a tibial axis, causing a height of the expandable surgical device to increase in a proximal direction into an expanded state to engage an interior portion of a tibia intramedullary canal.

In embodiments, the expandable surgical device is selected from a group consisting of a reamer and an implant. In embodiments, the surgical device includes a first height in the collapsed state, and a second height in the expanded state, wherein the second height is at least twice the first height. In embodiments, increasing the height of the expandable surgical device into an expanded state further includes rotating a shaft that is coupled the expandable surgical device includes a base, a first bone engagement segment and a second bone engagement segment, engaging a clutch with the base to inhibit rotation of the base, and while rotating the shaft, causing the first and second bone engagement segments to expand in sequence in the superior direction to increase the height of the expandable surgical device.

In embodiments, the method further includes causing a superior bone engagement segment to rotate relative to the base, the first bone engagement segment, and the second bone engagement segment, to permit the superior bone engagement segment to expand in the superior direction relative to the base. In embodiments, when the first and second bone engagement segments are threadably coupled to each other, wherein increasing the height of the expandable surgical device into an expanded state further includes causing rotation of a second bone engagement segment relative to the first bone engagement segment and the base to permit the second bone engagement segment to expand in the superior direction relative to the first bone engagement segment and the base, engaging a stop element on the base or the first bone engagement segment to inhibit further rotation of the second bone engagement segment, and causing rotation of the first bone engagement segment relative to the base to permit the first bone engagement segment to expand in the superior direction relative to the base.

In embodiments, the method further includes inserting a guidewire into the interior portion of the tibia, and inserting the expandable surgical device over the guidewire in an osteotomy. In embodiments, engaging a clutch with the base includes engaging the base with an engagement element selected from at least one of a spoke and a cog into slots in the surgical device inhibit rotation of the base. In embodiments, the first bone engagement segment further includes a head reamer element, the second bone engagement segment further includes at least one intermediate reamer element, and a third bone engagement segment includes a base reamer element, the at least one intermediate reamer element and the base reamer element further includes leading faces includes cutting teeth.

In embodiments, a surgical device includes a housing, a reamer, and an adjustment mechanism. The housing includes a longitudinal length disposed along a first axis, a width, and at least one location feature disposed on the longitudinal length, a reamer disposed entirely within the housing. The reamer is nested entirely within the housing. The reamer includes a plurality of nested reamer elements including a first reamer element and a second reamer element nested within the first reamer element, the first reamer element and the second reamer element configured to telescope out of the housing. The adjustment mechanism includes a first adjustment mechanism face disposed on a second axis and configured to contact an anterior surface of a patient's tibia. The adjustment mechanism is configured to be movably attached to the housing along the longitudinal length.

In embodiments, the first adjustment mechanism face is configured to contact the anterior surface of the patient's tibia when the adjustment mechanism is at a contact location along the longitudinal length, and wherein the at least one location feature is configured to determine the contact location. In embodiments, the first axis and the second axis are substantially perpendicular. In embodiments, the at least one location feature includes an indicator along at least a portion of the width of the housing. In embodiments, the reamer is oriented substantially perpendicularly to the longitudinal length of the housing. In embodiments, the housing includes at least two location features disposed along the longitudinal length.

In embodiments, the housing further includes a first lateral side and a second lateral side, the adjustment mechanism further includes a first stabilizing arm configured to contact the first lateral side and a second stabilizing arm configured to contact the second lateral side.

In embodiments, the housing further includes a first section of a first length, first width, and first height, and a second section of a second length, second width, and second height, wherein the reamer is disposed within the first section, wherein the first width and first height are greater than the second width and second height, and wherein the first length is less than the second length. In embodiments, a resected area of a patient's ankle joint includes a resection length, a resection width, and a resection height, wherein the resection width is greater than or equal to the first width, the resection height is greater than or equal to the first height, and the resection length is greater than or equal to the first length. In embodiments, the first section of the housing further includes a nose disposed proximally to the patient's tibia.

In embodiments, a method of orienting a reamer includes providing the reamer, orienting the reamer within a housing, the housing includes at least one location feature, providing an adjustment mechanism includes a first adjustment mechanism face configured to contact an anterior surface of a patient's tibia, movably affixing the adjustment mechanism to the housing, positioning the housing partially within a resected area of a patient's tibia joint based on a position of the at least one location feature of the housing with respect to the anterior surface of the patient's tibia, sliding the adjustment mechanism along a longitudinal length of the housing until the first adjustment mechanism face contacts an anterior surface of the patient's tibia, and determining whether the adjustment mechanism, when contacting the anterior surface of the patient's tibia, aligns the reamer with an intramedullary canal of the patient's tibia.

In embodiments, when the adjustment mechanism is determined not to align with the intramedullary canal of patient's tibia, the method further includes positioning the housing partially within the resected area of the patient's tibia joint based on a position of a second location feature of the housing with respect to the anterior surface of the patient's tibia, and determining whether the adjustment mechanism, when contacting the anterior surface of the patient's tibia, aligns the reamer with the intramedullary canal of the patient's tibia.

In embodiments, when the adjustment mechanism is determined to align the reamer with the intramedullary canal of the patient's tibia, further includes locking the adjustment mechanism relative to the first location feature of the housing. In embodiments, the method includes advancing the reamer into the intramedullary canal of the patient's tibia. In embodiments, the method includes removing the reamer from the intramedullary canal of the patient's tibia and inserting an implant into the intramedullary canal. In embodiments, the first location feature includes an indicator along a portion of a width of the housing.

In embodiments, the housing further includes a first section includes a first length, first width, and first height, and a second section includes a second length, second width, and second height, wherein the reamer is disposed within the first section, wherein the first width and height are greater than the second width and height, respectively, and wherein the first length is less than the second length. In embodiments, the housing further includes a shaft oriented substantially parallel to the first axis, the housing includes a patient distal end and a patient proximal end, wherein the shaft is configured to be engaged by a power driver at the patient distal end.

In embodiments, the housing further includes a first gear and a second gear and the reamer further includes a plurality of nested reamer elements, wherein the shaft is configured to engage the first gear at a first location within the housing disposed between the patient proximal end and the patient distal end, wherein the second gear is configured to engage the first gear at a second location within the housing disposed between the patient proximal end and the first location and is configured to engage the reamer at a third location within the housing disposed between the patient proximal end and the second location, wherein rotation of the shaft is configured to cause rotation of the first gear and the second gear, wherein rotation of the first gear and the second gear is configured to cause rotation of the reamer, and wherein rotation of the reamer is configured to cause expansion of the plurality of nested reamer elements in a superior direction from the housing from the collapsed state into an expanded state.

In embodiments, the plurality of nested reamer elements further includes a head reamer element, at least one intermediate reamer element, and a base reamer element, the at least one intermediate reamer element further includes leading faces includes cutting teeth.

In embodiments, the head reamer element is disposed superior to all other of the plurality of nested reamer elements when in an expanded state and wherein the head reamer element is nested within an adjacent one of the plurality of nested reamer elements.

In embodiments, the plurality of nested reamer elements includes a third reamer element, wherein the second reamer element is threadably coupled to the first reamer element and the third reamer element is threadably coupled to the second reamer element, and wherein rotation of the shaft is configured to cause the first reamer element to rotate and expand in the superior direction relative to the second reamer element and the third reamer element.

In embodiments, the surgical device further includes a clutch coupled to the housing and the reamer, wherein the clutch is configured to control rotation of at least one of the shaft, the first gear, the second gear, and the reamer.

In embodiments, the surgical device is configured to be connected to the patient's tibia using a plurality of pins. In embodiments, the surgical device is not configured to be used with additional guide elements attached to the anterior surface or an inferior surface of the patient's tibia. In embodiments, the housing further includes a shaft oriented parallel to the longitudinal axis, wherein the shaft is configured to be engaged by a power driver.

In embodiments, the first reamer element further includes an internal thread and an external thread and the second reamer element further includes an internal thread and an external thread, wherein the external thread of the first reamer element is configured to threadingly engage the internal thread of the second reamer element.

In embodiments, the reamer further includes at least one stop element configured to inhibit further advancement of at least one of the plurality of reamer elements in a superior direction beyond a certain expansion distance relative to an adjacent one of the plurality of nested reamer elements.

In embodiments, the housing further includes a patient distal end and a patient proximal end and includes a first gear and a second gear and the reamer further includes a plurality of nested reamer elements, wherein the shaft is configured to engage the power driver at the patient distal end and is configured to engage the first gear at a first location within the housing disposed between the patient proximal end and the patient distal end, wherein the second gear is configured to engage the first gear at a second location within the housing disposed between the patient proximal end and the first location, wherein rotation of the shaft causes rotation of the first gear and the second gear, wherein rotation of the first gear and the second gear causes rotation of the reamer, and wherein rotation of the reamer cause expansion of the plurality of nested reamer elements.

In embodiments, the plurality of nested reamer elements further includes a head reamer element, at least one intermediate reamer element, and a base reamer element, the head reamer element and the at least one intermediate reamer element further includes leading faces includes cutting teeth. In embodiments, the surgical device is configured to be connected to the patient's tibia using a plurality of pins. In embodiments, the surgical device is not configured to be used with additional guide elements attached to the anterior surface or an inferior surface of the patient's tibia.

In embodiments, a tibial intramedullary surgical implant includes a head stem component, at least one intermediate stem component, and a base stem component. The head stem component includes an inferior face includes a recess. The at least one intermediate stem component includes a superior face includes a projection and a base end includes a recess. The base stem component includes a superior face includes a projection. The projection of the superior face of the at least one intermediate stem component is configured to be received in the recess of the inferior face of the head stem component to form a first press-fit connection. The projection of the superior face of the base stem component is configured to be received in the recess of the inferior face of at least one intermediate stem component to form a second press-fit connection.

In embodiments, the projection of the head end and the recess of the base end further include substantially frusto-conical cross-sections. In embodiments, projection of the head end of the at least one intermediate stem component includes a projection cross-sectional dimension and the projection of the head end of the base stem component includes the projection cross-sectional dimension. In embodiments, the recess of the base end of the head stem component includes a recess cross-sectional dimension and the recess of the base end of the at least one intermediate stem component includes the recess cross-sectional dimension. In embodiments, the recess cross-sectional dimension and the projection cross-sectional dimension are substantially the same.

In embodiments, the head stem component includes a first cross-sectional dimension, the at least one intermediate stem component includes a second cross-sectional dimension, and the base stem component includes a third cross-sectional dimension, wherein the first cross-sectional dimension is less than or equal to the second cross-sectional dimension and the second cross-sectional dimension is less than or equal to the third cross-sectional dimension.

In embodiments, the implant is disposed along a longitudinal axis and the head stem component includes a sidewall and at least one bore disposed through the sidewall, at least one intermediate stem component includes a sidewall and at least one bore disposed through the sidewall, and base stem component includes a sidewall and at least one bore disposed through the sidewall, and wherein the at least one bore through each of the head stem component, at least one intermediate stem component, and base stem component are oriented perpendicularly to the longitudinal axis.

In embodiments, the recess of the head stem component, projection of the at least one intermediate stem component, recess of the at least one intermediate stem component, and projection of the base stem component each include a Morse taper. In embodiments, the Morse taper of each of the recess of the head stem component, projection of the at least one intermediate stem component, recess of the at least one intermediate stem component, and projection of the base stem component are configured to form a press-fit. In embodiments, the Morse taper of the recess of the head stem component includes a first recess taper angle, the Morse taper of the projection of the at least one intermediate stem component includes a first projection taper angle, the Morse taper of the recess of the at least one intermediate stem component includes a second recess taper angle, and the Morse taper of the projection of the base stem component includes a second projection taper angle, and wherein the first recess taper angle, the first projection taper angle, the second recess taper angle, and the second projection taper angle include an angle within 1° of one another.

In embodiments, the recess of the head stem component includes a first recess height and a first recess width, the projection of the at least one intermediate stem component includes a first projection height and a first projection width, the recess of the at least one intermediate stem component includes a second recess height and a second recess width, and the projection of the base stem component includes a second projection height and a second projection width. In embodiments, the first recess height, first projection height, second recess height, and second projection height are configured to form a press-fit and the first recess width, first projection width, second recess width, and second projection width are configured to form a press-fit. In embodiments, the first recess height, first projection height, second recess height, and second projection height include a tolerance of 0.125 mm and the first recess width, first projection width, second recess width, and second projection width include a tolerance of 0.125 mm.

In embodiments, In embodiments, a method of implanting a surgical implant includes drilling an intramedullary canal in a patient's tibia, inserting a head stem component into the intramedullary canal, wherein the head stem component includes a base end includes a recess, inserting at least one intermediate stem component into the intramedullary canal, wherein the at least one intermediate stem component includes a head end includes a projection and a base end includes a recess, engaging the recess of the head stem component with the projection of the at least one intermediate stem component, forming a press-fit connection between the projection and the recess, inserting a base stem component into the intramedullary canal, wherein the base stem component includes a head end includes a projection, engaging the recess of the at least one intermediate stem component with the projection of the base stem component, and forming a press-fit connection between the projection and the recess.

In embodiments, a surgical device system for repairing an ankle joint includes an implant and a placement tool. The implant oriented along a longitudinal axis and includes a plurality of stem components includes sidewalls, wherein the plurality of stem components each include at least one bore through the sidewalls of the plurality of stem components and oriented perpendicularly to the longitudinal axis. The placement tool includes a first prong and a second prong, a first arm, and a second arm, wherein the first arm and the second arm are configured to intersect at a pivot point. The first prong and the second prong of the placement tool are configured to engage with two of the at least one bores of adjacent stem components.

In embodiments, the plurality of stem components each include a substantially circular cross-section. In embodiments, the first prong includes a first engagement element and second engagement element, and the second prong includes a third engagement element and fourth engagement element, wherein the first engagement element and the third engagement element are configured to be inserted into one of the at least one bore of adjacent stem components, and wherein the second engagement element and the fourth engagement element are configured to be inserted into one of the at least one bore of adjacent stem components. In embodiments, the plurality of stem components each include at least two bores. In embodiments, the first prong includes a first engagement element and a second engagement element, and the second prong includes a third engagement element and a fourth engagement element, the first engagement element and the third engagement element configured to be inserted into two of the at least one bores of a first adjacent stem component, and the second engagement element and the fourth engagement element configured to be inserted into two of the at least one bores of a second adjacent stem component.

In embodiments, the first arm includes the first prong and a first grip section and the second arm includes the second prong and a second grip section. In embodiments, the placement tool further includes a pivot component disposed at the pivot point.

In embodiments, the implant further includes a proximal end and a distal end disposed distally to the proximal end with respect to the longitudinal axis, and the plurality of stem components further include a head stem component disposed at the distal end of the implant and includes an inferior face disposed on a proximal end of the head stem component, a first recess extending distally from the inferior face and extending to a distal recess face, and two head stem bores disposed distally with respect to the distal recess face of the first recess, at least one intermediate stem component disposed proximally with respect to the head stem component, the at least one intermediate stem component includes an inferior face disposed on a proximal end of each at least one intermediate stem component, a second recess disposed on the inferior face of each at least one intermediate stem component and extending distally from the inferior face of the at least one intermediate stem to a distal recess face, and two intermediate stem bores disposed distally with respect to the distal recess face of the second recess, and a base stem component disposed proximally with respect to the at least one intermediate stem component, the base stem component includes an inferior face disposed on a proximal end of the base stem component, a third recess disposed on the inferior face of the base stem component and extending distally from the inferior face of the base stem to a distal recess face, and two base stem bores intersecting with the third recess proximal to the distal recess face of the third recess.

In embodiments, the implant includes a vertical centerline and wherein the two head stem bores of the head stem component includes a first bore laterally offset from the vertical centerline in a first direction to a lateral offset distance, and a second bore laterally offset from the vertical centerline in a second direction to the lateral offset distance, wherein the second direction is opposite to the first direction, the two intermediate stem bores of the at least one intermediate stem component includes a third bore laterally offset from the vertical centerline in the first direction to the lateral offset distance, and a fourth bore laterally offset from the vertical centerline in the second direction to the lateral offset distance, and the two base stem bores of the base stem component includes a fifth bore laterally offset from the vertical centerline in the first direction to the lateral offset distance, and a sixth bore laterally offset from the vertical centerline in the second direction to the lateral offset distance. In embodiments, the first bore, second bore, third bore, fourth bore, fifth bore, and sixth bore further include an anterior opening and a posterior opening.

In embodiments, the first prong includes a first engagement element and a second engagement element, and a second prong includes a third engagement element and a fourth engagement element, wherein the first engagement element is configured to be inserted into one of the anterior opening or posterior opening of the first bore, third bore, and fifth bore, wherein, when the first engagement element is inserted into the anterior opening of one of the first bore, third bore, and fifth bore, the second engagement element is configured to be inserted into an adjacent anterior opening, when the first engagement element is inserted into the posterior opening of one of the first bore, third bore, and fifth bore, the second engagement element is configured to be inserted into an adjacent posterior opening, when the third engagement element is inserted into the anterior opening of one of the third bore and fifth bore, the fourth engagement element is configured to be inserted into an adjacent opening, and when the third engagement element is inserted into the posterior opening of one of the third bore and fifth bore, the fourth engagement element is configured to be inserted into an adjacent opening.

In embodiments, the first engagement element, second engagement element, third engagement element, and fourth engagement element include a first insertion length, second insertion length, third insertion length, and fourth insertion length, respectively, and the first bore, second bore, third bore, fourth bore, fifth bore, and sixth bore include a first bore length, second bore length, third bore length, fourth bore length, fifth bore length, and sixth bore length, respectively, wherein the first insertion length and third insertion length are greater than the first bore length, third bore length, and fifth bore length, and wherein the second insertion length and fourth insertion length are greater than the second bore length, fourth bore length, and sixth bore length.

In embodiments, method of inserting an implant into an intramedullary canal of a tibia, includes providing an implant oriented along a longitudinal axis and includes a head stem component includes a first bore, a second bore, and an inferior face includes a first recess, and at least one intermediate stem component includes a third bore, a fourth bore, an inferior face includes a second recess, and a superior face includes a first engagement feature, providing a placement tool includes a first prong and a second prong, wherein the first prong includes a first engagement element and a second engagement element and the second prong includes a third engagement element and a fourth engagement element, inserting the first engagement element into the first bore and the second engagement element into the second bore, inserting the third engagement element into the third bore and the fourth engagement element into the fourth bore, inserting the first engagement feature into the first recess, and squeezing the placement tool to apply pressure to the head stem component and the at least one intermediate stem component to engage the first engagement feature and the first recess.

In embodiments, the implant further includes a base stem component includes a fifth bore, a sixth bore, a superior face includes a second engagement feature, and an inferior face includes a third recess. In embodiments, the first bore, second bore, third bore, fourth bore, fifth bore, and sixth bore further include an anterior opening and a posterior opening. In embodiments, the method includes squeezing the placement tool to apply pressure to the at least one intermediate stem component and the base stem component to engage the second engagement feature and second recess. In embodiments, the method includes providing a tray includes a superior face includes a third engagement feature, and inserting the third engagement feature into the third recess.

In embodiments, the method includes inserting the first engagement element into the third bore and the second insertion element into the fourth bore, inserting the third engagement element into the fifth bore and the fourth engagement element into the sixth bore, and squeezing the gripping mechanism to apply pressure to the at least one intermediate stem component and the base stem component to engage the second engagement feature and the second recess. In embodiments, the first bore and second bore of the head stem component are substantially coplanar, the first bore and second bore of the at least intermediate stem component are substantially coplanar, and the first bore and second bore of the base stem component are substantially coplanar.

In embodiments, a surgical implant system includes a reamer and an implant stem. The reamer includes a first reamer component includes a first substantially circular cross-sectional shape includes a first reamer circumference, a second reamer component includes a second substantially circular cross-sectional shape includes a second reamer circumference, and a third reamer component includes a third substantially circular cross-sectional shape includes a third reamer circumference, wherein the second reamer component is configured to engage the first reamer component and the third reamer component. The implant stem, includes a head stem component includes a first substantially circular cross-sectional shape includes a head stem circumference substantially equal to the first reamer circumference, at least one intermediate stem component includes a second substantially circular cross-sectional shape includes an intermediate stem circumference substantially equal to the second reamer circumference, and a base stem component includes a third substantially circular cross-sectional shape includes a base stem circumference substantially equal to the third reamer circumference. The at least one intermediate stem component is configured to engage the head stem component and the third stem component.

In embodiments, a surgical implant for ankle replacement surgery includes expandable surgical device and a tray. The expandable surgical device oriented along a longitudinal axis and includes a base stem component, wherein the base stem component includes a body, the body includes a substantially circular cross-section, an inferior face, the inferior face includes a circumferential opening, and a recess extending distally from the circumferential opening to an distal wall of the recess, the recess includes a neck portion extending distally from the circumferential opening, the neck portion includes a proximal end disposed at the circumferential opening and a distal end, the recess further includes a substantially spherical segment extending distally from the distal end of the neck portion to the distal wall of the recess, the substantially spherical segment forming a cross-sectional dimension of increasing diameter beginning at the distal end of the neck portion and reaching a maximum recess diameter at an equator, the recess transitioning at the equator to a cross-sectional dimension of decreasing diameter, terminating at the distal wall of the recess. The tray includes a ball member includes a plurality of petals centered around a central axis, the plurality of petals includes a rounded outer wall, the rounded outer wall includes a substantially spherical segment substantially matching the contour of the substantially spherical segment of the recess, the plurality of petals includes a radially retracted position and a radially extended position, wherein the plurality of petals are further from the central axis in the radially extended position. The ball member of the tray is configured to be received in the neck portion of the recess of the base stem component when the petals are in the radially retracted position, and further configured such that the position of the tray can be rotatably adjusted relative to the base stem component when the petals are not in a radially extended position, and the tray is locked in a position in relation to the base stem component when the plurality of petals are in the radially extended position.

In embodiments, the tray further includes a vertically oriented opening centered around the central axis, and the surgical implant further includes a nut configured to be received within the vertically oriented opening and at least partially surrounded by the plurality of petals. In embodiments, the nut includes a substantially frustoconical portion. In embodiments, the plurality of petals further includes a substantially frustoconical wall opposite the rounded outer wall and adjacent to and engaging the substantially frustoconical portion of the nut. In embodiments, at least a portion of the vertically oriented opening includes an internal thread. In embodiments, at least a portion of the nut includes an external thread configured to engage the internal thread of the vertically oriented opening. In embodiments, the nut is configured to move distally and apply a radially outward force on the plurality of petals by engagement of the frustoconical portion of the nut with the frustoconical walls of the plurality of petals. In embodiments, a tibial tray tap is configured to apply upward force to the nut.

In embodiments, the tibial tray tap includes a superior arm, an intermediate arm, and a lower arm, the superior arm includes an engagement element, wherein the engagement element is configured to engage the nut and the intermediate arm is laterally offset from and substantially parallel to the longitudinal axis.

In embodiments, a method of inserting a surgical implant includes providing a surgical implant and providing a tray. The surgical implant includes a base stem component including a body, the body includes a substantially circular cross-section, an inferior face, the inferior face includes a circumferential opening, a recess extending distally from the circumferential opening to an distal wall of the recess, the recess includes a neck portion extending distally from the circumferential opening, the neck portion includes a proximal end disposed at the circumferential opening and a distal end, the recess further includes a substantially spherical segment extending distally from the distal end of the neck to the distal wall of the recess, the substantially spherical segment forming a cross-sectional dimension of increasing diameter beginning at the distal end of the neck and reaching a maximum recess diameter at an equator, the recess transitioning at the equator to a cross-sectional dimension of decreasing diameter, terminating at the distal wall of the recess. The tray includes a ball member includes a plurality of petals centered around a central axis, the plurality of petals includes a rounded outer wall, the rounded outer wall includes a substantially spherical segment substantially matching the contour of the substantially spherical segment of the recess, the plurality of petals includes a radially retracted position and a radially extended position, wherein the plurality of petals are further from the central axis in the extended position. The method includes inserting the base stem component into an intramedullary canal of a patient's tibia, and inserting the ball member of the tray into the recess of the base stem component, wherein the ball member of the tray is configured to be received in the neck portion of the recess of the base stem component when the plurality of petals are in the radially retracted position, and further configured such that the position of the tray can be rotatably adjusted relative to the base stem component when the plurality of petals are not in a radially extended position, and the tray is locked in a position in relation to the base stem component when the plurality of petals are in the radially extended position.

In embodiments, the tray further includes a vertically oriented opening, the method further includes providing a nut, engaging the nut in the vertically oriented opening of the tray, advancing the nut distally through the vertically oriented opening in the tray into an opening disposed within the plurality of petals, expanding the plurality of petals outward to engage an inner sidewall of the recess. In embodiments, the method includes providing a tibial tray tap including a superior arm, an intermediate arm, and a lower arm, wherein the superior arm includes an engagement element, engaging the tibial tray with the engagement element, applying upward force to the lower arm of the tibial tray tap. In embodiments, the tibial tray is configured to engage a first artificial joint surface. In embodiments, the tibial tray further includes a vertically oriented opening centered around the central axis, and the tray further includes a nut configured to be received within the vertically oriented opening and at least partially surrounded by the plurality of petals.

In embodiments, the nut includes a substantially frustoconical portion. In embodiments, the plurality of petals further includes a substantially frustoconical wall opposite the rounded outer wall and adjacent to and engaging the substantially frustoconical portion of the nut. In embodiments, at least a portion of the vertically oriented opening includes an internal thread. In embodiments, at least a portion of the nut includes an external thread configured to engage the internal thread of the vertically oriented opening. In embodiments, the nut is configured to move distally and apply a radially outward force on the plurality of petals by engagement of the substantially frustoconical portion of the nut with the substantially frustoconical walls of the plurality of petals. In embodiments, advancing the nut distally through the vertically oriented opening in the tray includes applying a wrench to the nut.

In embodiments, a talar implant includes a body and a first keel. The body includes an inferior face. The first keel disposed on the inferior face of the body and includes a first keel length, a first keel depth, and a first keel width. The first keel length is greater than the first keel depth and the first keel width. In embodiments, a second keel includes a second keel length, a second keel depth, and a second keel width. In embodiments, the second keel length is greater than the second keel depth and the second keel width. In embodiments, the first keel and the second keel include substantially trapezoidal cross-sections. In embodiments, the first keel includes a first proximal keel length and the second keel includes a second proximal keel length, the first proximal keel length and second proximal keel length disposed proximally to the body, and wherein the first keel includes a first distal keel length and the second keel includes a second distal keel length, the first distal keel length and second distal keel length disposed distally to the body. In embodiments, the proximal keel lengths are greater than the distal keel lengths. In embodiments, the first keel and the second keel further include keel features. In embodiments, the first keel and the second keel further include cross-sectional keel openings. In embodiments, the cross-sectional keel openings include a shape selected from one of substantially trapezoidal cross-sections, oblong cross-sections, non-circular cross-sections, and fin shaped cross-sections.

In embodiments, the talar implant includes a peg. In embodiments, the peg further includes a substantially cylindrical shape terminating in a substantially hemispherical shape. In embodiments, the first keel and the second keel further include a first keel arm and the second keel arm, respectively. In embodiments, the peg is disposed at an angle with respect to an inferior face of the body. In embodiments, the first keel arm and the second keel arm are disposed at the angle with respect to the inferior face of the body. In embodiments, a superior face of the body includes a sulcus. In embodiments, a first artificial joint surface is configured to engage the superior face of the body.

DETAILED DESCRIPTION

In the following detailed description of embodiments, reference may be made to the accompanying drawings, which form a part hereof and in which may be shown, by way of illustration, specific embodiments in which the invention may be practiced. Specific details disclosed herein may be in every case a non-limiting embodiment representing concrete ways in which the concepts of the invention may be practiced. This serves to teach one skilled in the art to employ the present invention in virtually any appropriately detailed system, structure or manner consistent with those concepts. It will be seen that various changes and alternatives to the specific described embodiments and the details of those embodiments may be made within the scope of the invention. Because many varying and different embodiments may be made within the scope of the inventive concepts herein described and in the specific embodiments herein detailed without departing from the scope of the present invention, it may be to be understood that the details herein may be to be interpreted as illustrative and not as limiting.

The various directions such as "superior," "lower," "inferior," "top," "back," "front," "perpendicular", "vertical", "horizontal," "length" and "width" and so forth used in the detailed description of embodiments may be made only for easier explanation in conjunction with the drawings to express the concepts of the invention. The elements in embodiments may be oriented differently while performing the same function and accomplishing the same result as obtained with the embodiments herein detailed, and such terminologies may be not to be understood as limiting the concepts which the embodiments exemplify.

Figure 1:
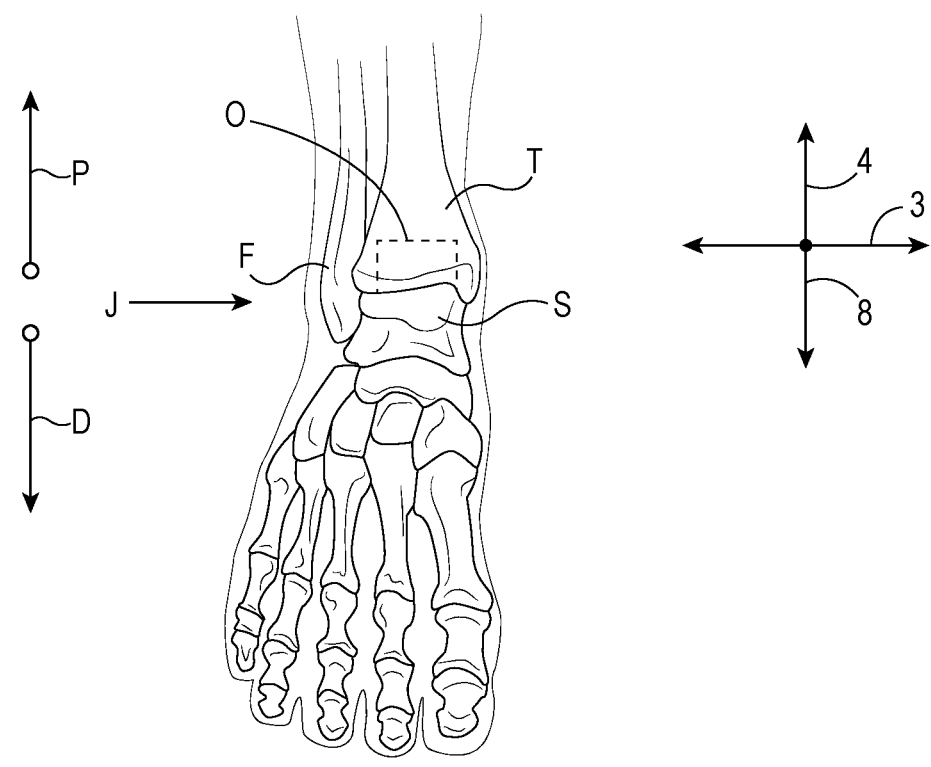
FIG. 1 is an anterior view of an ankle joint.
Figure 2:
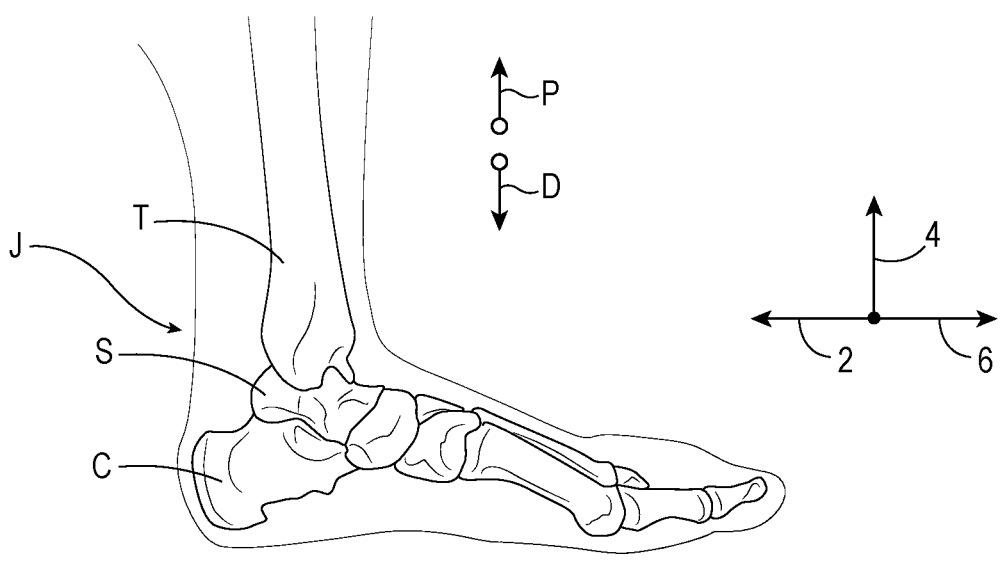
FIG. 2 is a lateral view of an ankle joint.

In describing the system 10 below, various directional references may be used and may be shown in FIGS. 1 and 2. A posterior direction 2 refers to a direction from an anterior portion of the ankle joint toward the posterior portion of the ankle joint. An anterior direction 6 may be opposite the posterior direction 2. A superior direction 4 may be perpendicular to the anterior direction 6 and posterior direction 2 and extends generally upwardly away from the bottom of the foot (e.g. toward the knee (not shown)). Superior Direction may be also sometimes referred to as 'proximal' P direction toward the head from the foot. The inferior direction 8 may be opposite the superior direction 4. Inferior Direction may be sometimes referred to as 'plantar' direction toward the foot from the head. A transverse direction 3 may be generally perpendicular to the anterior direction, posterior direction, and superior-inferior direction. The transverse direction 3 generally may include both a lateral and medial directions. Furthermore, with reference to a surgical device, a proximal direction Pis towards the top of the device when implanted and distal direction D may be toward the bottom of the device when implanted or in use. All of the aforementioned directional references are used to illustrate the invention with reference to the anatomy of the ankle joint J but should not be considered limiting unless specifically indicated as limiting.

As used herein, the use of the word "a" or "an" when used in conjunction with the term "comprising" (or the synonymous "having" or "including") in the claims and/or the specification may mean "one," but it may be also consistent with the meaning of "one or more," "at least one," and "one or more than one." In addition, as used herein, the phrase "connected to" means joined to or placed into communication with, either directly or through intermediate components.

As shown in FIGS. 1-46, embodiments of the present disclosure include a surgical system. The surgical system may include at least one of a surgical device 10, an implant 200, a placement tool 300, a tibial tray tap 400, and a talar implant 600.

I. Expandable Reamer and Implant

Embodiments of the present disclosure may include surgical system 10 configured for preparation and implantation primarily of a device in the tibia T of the ankle joint J. FIGS. 1 and 2 illustrates a typical ankle J including a distal tibia T and fibula F engaging the talus S via various ligaments (ligaments not shown). The calcaneus C sits inferior to the talus T and forms the heel of the foot. Embodiments of the system as described herein may be inserted into an insertion site O at the tibia, as shown in FIGS. 1 and 2 (shown in dashed lines). An insertion site may be an any location prepared to receive the expandable surgical device therein and may be an osteotomy or an arthrotomy. The system 10, therefore, may be configured to specifically enter the insertion site O in a posterior direction 2. In certain embodiments, the system 10 does not require access to the tibia via a combined anterior and plantar approach for instrumentation through the plantar foot pad and tissues as well as violating the bones of the calcaneus C and talus S.

Figures 3, 4:
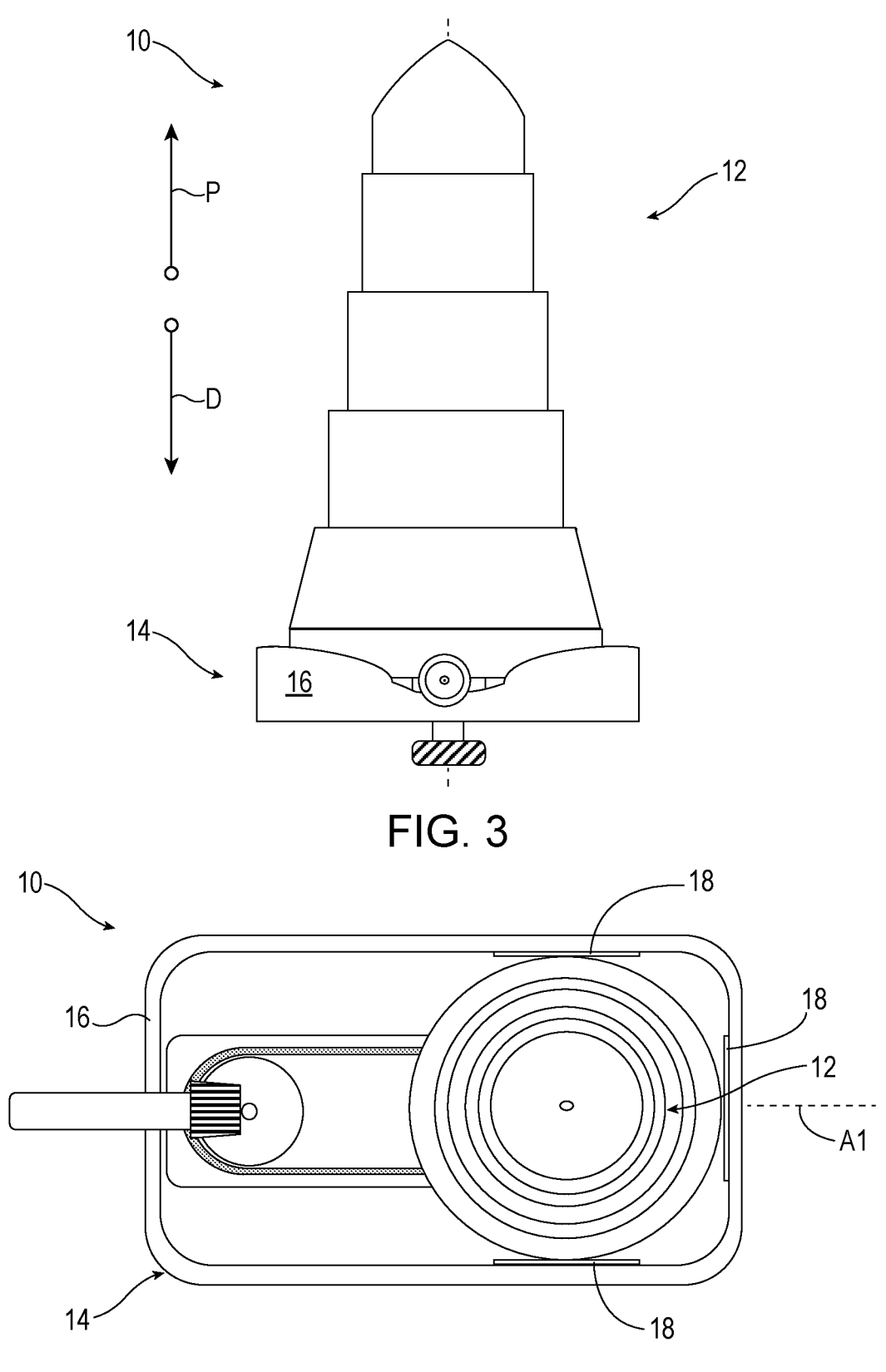
FIG. 3 is an anterior elevation view of a surgical system, including a fully expanded surgical device and track assembly.
FIG. 4 is a top view of the surgical system illustrated in FIG. 3.

FIGS. 3 and 4 illustrate an embodiment of the surgical system 10 for treating a damaged ankle joint. The system 10 may include an expandable surgical device 12, a track assembly 14, and optional additional distal implants (not shown). In some instances, the expandable surgical device 12 will serve as a reamer to instrument and prepare the tibia and a final implant to be left expanded in the tibia, both used to prepare the space and stabilize the distal portion of the tibia T. In other cases, the system 10 may include an expandable surgical device 12 configured as a reamer, which may be removed once the tissue site may be prepared, and an additional implant, for example implant 112 (FIG. 17) may be inserted in the inner portion of the tibia. Other equipment, such as guidewires, cutters, guides, nuts, bolts, mechanical articulations, and the like may be may included in the surgical system 10, as needed.

In certain embodiments, the system 10, including the expandable surgical device 12 and track assembly 14 may be insertable into insertion site O the tibia T in a posterior direction 2. This approach can be described as an anterior approach or access to the inner part of the tibia T. Once in position, the expandable surgical device 12 may be actuated to expand in a superior direction 4 (or proximal direction P) into the inner portion of the tibia T (see FIGS. 20 and 21). In certain embodiments, the expandable surgical device 10 may be configured to expand in a superior direction 4 without increasing its diameter during expansion.

Figure 5:
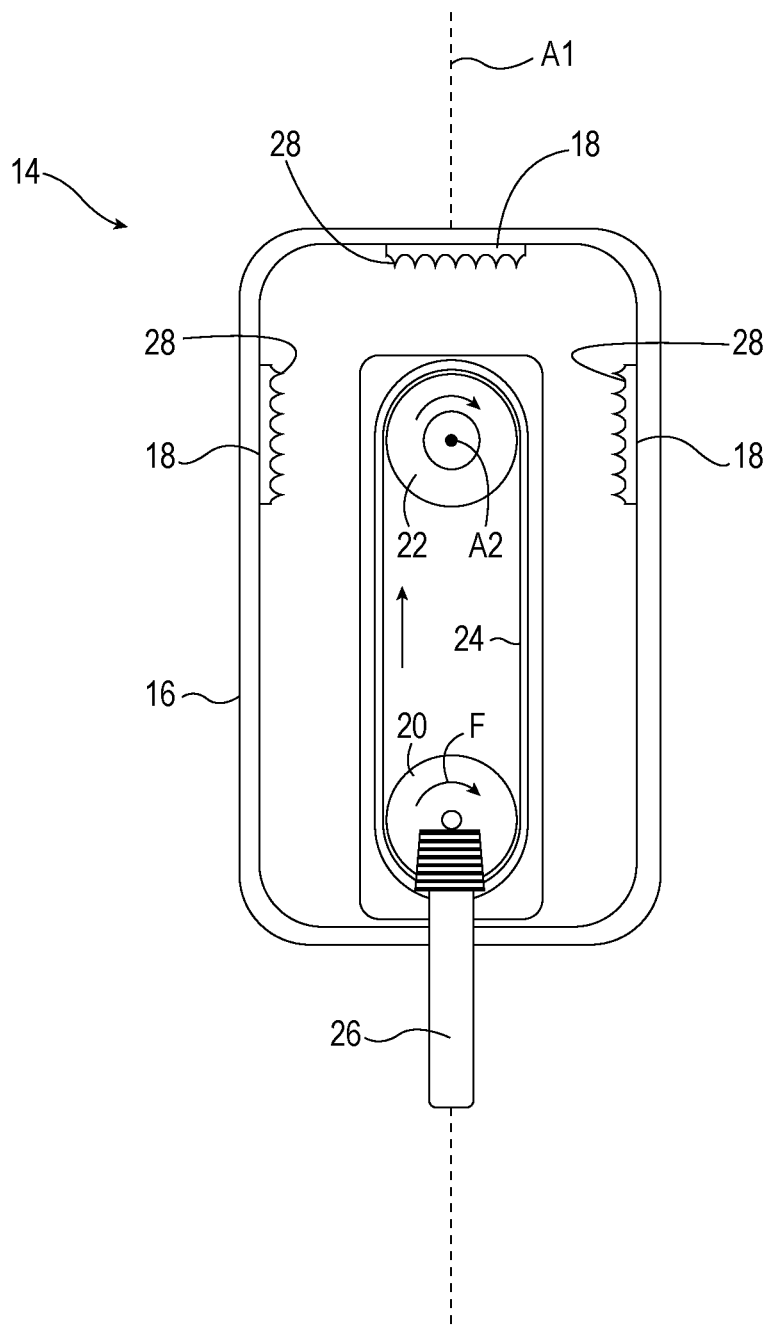
FIG. 5 is a top view of the track assembly with the surgical device removed, illustrating a part of the drive mechanism for expanding the surgical device.

In certain embodiments, referring to the embodiment shown in FIGS. 4 and 5, the track assembly 14 guides the surgical device 10 in place and serves as an interface for a power source. More specifically, the track assembly 14 may be used to transfer power from a power source into rotative motion, which may be used to cause expansion of the surgical device 12 in the superior direction 4. In certain embodiments, the track assembly 14 may include a generally elongated size and shape that may be suitable for insertion in from the anterior approach into the insertion site O in the posterior direction 2. In certain embodiments, the track assembly 14 may include a tray 16 having a length (not labeled) that extends along a first axis A1 and width (not labeled) that may be perpendicular to the length. While a rectangular shape may be shown, the tray can may include a number of different configurations and shapes. In certain embodiments, the track assembly 14 may be also configured to be substantially decoupled from the expandable surgical device 12 after insertion and removed from the surgical site.

Continuing with FIGS. 4 and 5, in one embodiment, the track assembly 14 may include a first gear 20, a second gear 22 spaced from the first gear 20 along the first axis A1, and a track 24 coupled to the first gear 20 and the second gear 22. The first gear 20, second gear 22 each may include teeth that interface with teeth on the track 24. In this configuration, rotation of the first gear 20 in rotational direction F causes the track 24 to rotate, which in turn causes the second gear 22 to rotate about the second axis A2. The second axis A2 may be perpendicular to and intersects the first axis A1. A power source 26, which in certain embodiments may be a drill with a threaded bit, can engage the first gear 22, which may include upper teeth or threads (not shown). Activation of the power source causes its bit to rotate (in a first orientation) and when engaged with the first gear 20, cause the gear to rotate in a first direction F. This, in turn, causes the track 24 to rotate, which, in turn, causes the second gear 22 to rotate in the first direction F about the second axis A2. Reversing rotation can occur by reversing rotational direction of the bit on the power source 26. Thus, the power source and track assembly may be designed to transfer rotative motion about an axis along a first plane from a power source into a rotative motion about a second plane (the second gear) that may be orthogonal to the first plane. The ability to transfer rotative motion around a first axis A1, via a drill or power source 26, into rotative motion about a second axis A2 (such as the second gear) that may be perpendicular to first axis A1 allows the system 10 to be inserted into the insertion site O in collapsed state and then expanded proximally during use. While a gear and track system may be shown to transfer power from the power source into rotational motion of the second gear 22, other mechanisms, such as a series of gears, belts, chain drives and other mechanical devices may be used. In another embodiment non-powered manual force from the surgeon transferred to the track assembly, could be used to create rotative motion along any desired plane, as may be the case. Other embodiments are shown and described herein.

Referring to FIGS. 4 and 5, in one embodiment, the track assembly 14 also may include a clutch 18. The clutch 18 may be configured to selectively engage and disengage a portion of the expandable surgical device 12 to control expansion in use. In the example shown, the clutch 18 may include a first plurality of engagement elements 28 that may be configured to engage a base 30 of the expandable surgical device 12, as further explained below. The engagement elements 28 may be teeth, projections, friction elements, detents, or any features that can engage a complimentary feature of the base 30. The clutch function could also be derived from a spoke or other form of stop to control rotation of certain segments while allowing rotation of other segments to selectively control expansion of the surgical device. For example, the clutch could be a spoke or cog, which can be engaged or disengaged periodically to selectively allow rotation of such segments of the surgical device thereby allowing further control of reaming or extension of the device height.

Figures 6, 7:
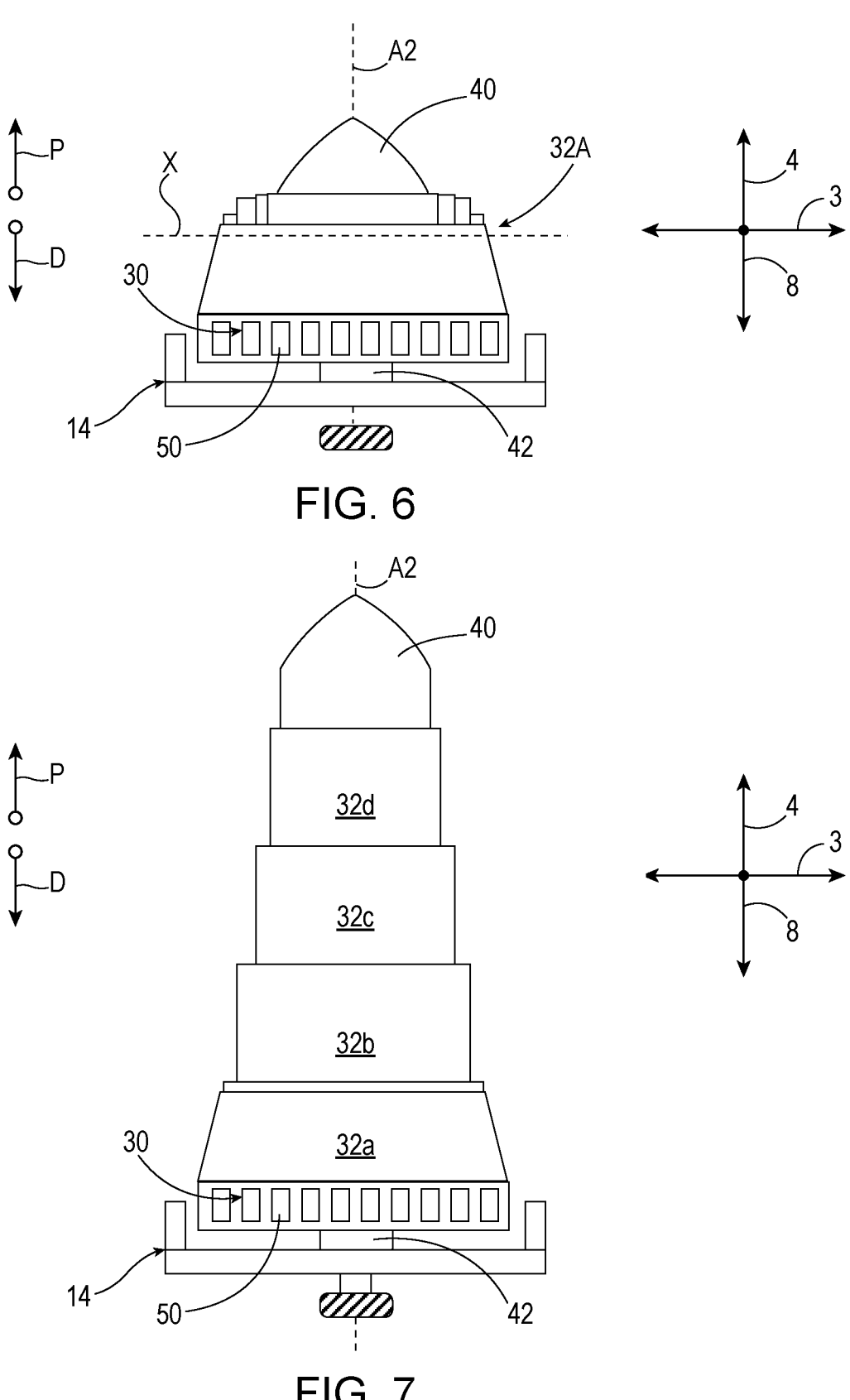
FIG. 6 is an elevation view of the surgical device in a collapsed state.
FIG. 7 is an elevation view of the surgical device in an expanded state.
Figure 8:
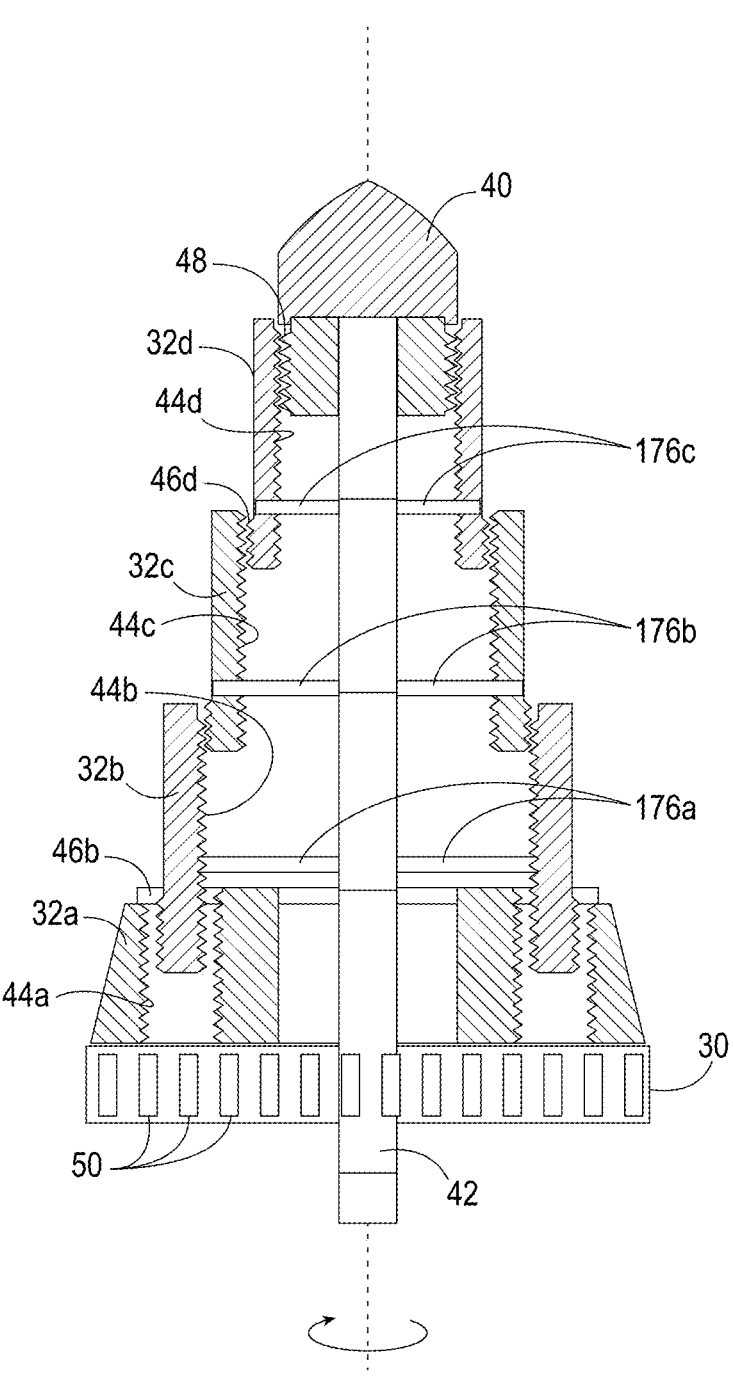
FIG. 8 is a cross-sectional elevation view of the surgical device shown in FIG. 7 in the expanded state.

FIGS. 6-8 illustrate an embodiment, with the expansion of the expandable surgical device 12 in a superior direction 4. The expandable surgical device 12 may include a base 30 and one or more bone engagement segments 32. The one or more bone engagement segments may include a superior bone engagement segment 40. The superior bone engagement segment 40 may be the superior or proximal-most portion of the surgical device 12. In one embodiment, the surgical device 12 also may include a shaft 42 coupled to the second gear 22 and each of the bone engagement segments 32, 40. In certain embodiment, the shaft 42 may be also configured to expand or telescope proximally as the device expands. Thus, in one example, the shaft 42 may be a telescoping shaft 42. In other embodiments, shaft 42 may be unitary and non-telescoping, and translates as the surgical device 12 expands. As the second gear 22 rotates, the shaft 42 rotates about the second axis A2 with it.

In one embodiment, the base 30 may be coupled to the shaft 42 and rotates with the shaft 42. In certain embodiment, the base 30 may include an outer wall with a plurality of engagement elements 50. The engagement elements 50 of the base 30 may be configured to engage with the engagement elements 28 of the clutch 18. The engagement elements 50 may be teeth, projections, friction elements, detents, or any features that can engage a complimentary feature of the clutch engagement elements 28.

In one embodiment, referring to FIGS. 6 and 7, the expandable surgical device 12 may include at least one bone engagement segment 32 in addition to the superior bone engagement segment 40 that may be movably coupled to each other and movable relative to each other. In the embodiment shown, the bone engagement segments may be generally circular in cross-section and may be nested together in a collapsed state as shown in FIG. 6. In this embodiment, four connected bone engagement segments 32 and a superior bone engagement segment 40 may be shown. More specifically, the surgical device 12 may include a first bone engagement segment 32a coupled to the base 30, a second bone engagement segment 32b coupled to the first bone engagement segment 32a, a third bone engagement segment 32c coupled to the second bone engagement segment 32b and a fourth bone engagement segment 32d coupled to the third bone engagement segment 32c. In the illustrated embodiment, the superior bone engagement segment 42 may be coupled to the fourth bone engagement segment 32d and forms a proximal-most bone engagement segment and may be superior to all other bone engagement segments when the surgical device 12 may be in the expanded state. While four interconnected bone engagement segments may be shown, fewer than four or more than four could be used. For example, the surgical device may include first bone engagement segment and a second bone engagement segment.

In one embodiment, the bone engagement segments 32 may be threadably coupled to each other such that each segment may be rotatable up to a certain point or distance. As shown, each bone engagement segment 32a-32b may include an internal thread and an external thread. In certain embodiment, at least one or more of the bone segments 32a-32d may include an external thread that extends along only a portion of its outer surface. For example, as shown in FIG. 8, bone engagement segment 32d may include in internal thread 44d that extends along an entirety of its inner surface and an external thread 46d that extends along only a portion of its outer surface. In one embodiment, bone engagement segments 32b, 32c, and 32d may be configured in a similar fashion with partial external threading. In one embodiment, superior bone engagement segment 40 may include an external thread 48. The first bone engagement segment 32a may include an internal thread 44a. But the internal thread 44a of the first bone engagement segment 32a threadably engages the external thread 44b of the second bone engagement segment 32b. The internal thread 44b of the second bone engagement segment 32b threadably engages the external thread 44c of the third bone engagement segment 32c. The internal thread 44c of the third bone engagement segment 32c threadably engages the external thread 44d of the fourth bone engagement segment 32d. The internal thread 44c of the third bone engagement segment 32c threadably engages the external thread 44d of the fourth bone engagement segment 32d. The internal thread 44d of the fourth bone segment 32d threadably engages the external thread 48 of the superior bone engagement element 40. In this way, and using rotative motion, each bone segment may be threadably and rotatably coupled to each other and in one embodiment, each segment will expand in sequence, e.g. the superior segment, then the fourth segment, then the third segment, then the second segment.

In one embodiment, the expandable surgical device 12 may include a stop element or locking mechanism (not shown) that may be configured to inhibit further advancement of a respective bone engagement segment in the superior direction beyond a certain expansion distance. In the embodiment shown, the stop element may include the partial external threading of the bone engagement segments 32, a mechanical detent, or a projection that blocks further rotation of an adjacent bone engagement segment 32 and/or superior bone engagement element 40.

In certain embodiments, each bone engagement segment 32 may include a diameter configured to aid in engaging bone. In the embodiment shown, each bone engagement segment 32 may include a diameter that may be equal to or greater than a diameter of superiorly adjacent bone engagement segment. This, in turn, creates a generally conical shape when in the fully expanded state, for example as shown in FIG. 7. However, in other embodiments, each bone engagement segment 32 may include a substantially similar diameter (see FIG. 18), therefore providing a more cylindrical shape configuration when fully expanded.

In certain embodiments, the bone engagement segments 40, 32 may be configured to engage bone, such as an inner portion of the tibia. When configured as a reamer 12, each bone engagement segment 40, 32 may include cutting elements 54', 56', 58', beveled edges, and the like, on one or more exterior surfaces, to aid in cutting into the bone during use. In one embodiment, the cutting elements 54', 56', 58' may include cutting teeth disposed on leading faces 54, 56, 58. In another embodiment, the cutting elements 54', 56', 58' may include cutting surfaces on exterior surfaces. In some embodiments, the bone engagement segments 40, 32, 30 may be configured to permit bone in-growth and may include an outer surface with bone in-growth structures, such as pores, holes, apertures and the like. In certain embodiments, the outer surface of the bone engagement segments may include depth indicators as needed. In further embodiments, the entire surgical device 12, including bone engagement segments 32, 40 and shaft 42 may be cannulated to fit over or along a guide wire.

In certain embodiments, the clutch 18 may be coupled to the track assembly 14 and can be activated to selectively engage the base 30 of the expandable surgical device 12. More specifically, the clutch 18 may be configured to transition between a) a locked position where the expandable surgical device 12 rotates, and b) an unlocked position where the base 30 does not rotate and each of bone engagement segments 32, 40 may be permitted to rotate, thereby advancing in the superior direction 4. More specifically, in the locked position, the base engagement elements 50 engage with the clutch engagement elements 28 so that the base 30 does not rotate. But in the locked position, the shaft 42 continues to permit rotation of the bone segments 32 and 40. This continued rotation causes a sequence expansion or elevation of the bone segments.

In other embodiments, the surgical device 12 may be configured to transition between a collapsed state and an expanded state. In the collapsed state, as shown in FIG. 6, bone engagement segments 32 may be nested together along a common plane X, and in the expanded state, as shown in FIG. 7, the bone engagement segments expand along the second axis A2 in the superior direction 4. Accordingly, the expandable surgical device may include a first height in a collapsed state (FIG. 6), and a second height in an expanded state (FIG. 7) that may be greater than the first height. In one embodiment, the second height, when in a fully expanded state may be at least twice the first height. Furthermore, a diameter along any portion of the expandable surgical device 12 does not increase during expansion into the expanded state. That is, the height of the device 12 increases during use but its diameter does not. This permits successive expansion of the bone engagement segments into the interior portion of the tibia T and aids in engaging the bone during use.

Figures 9, 10, 11, 12:
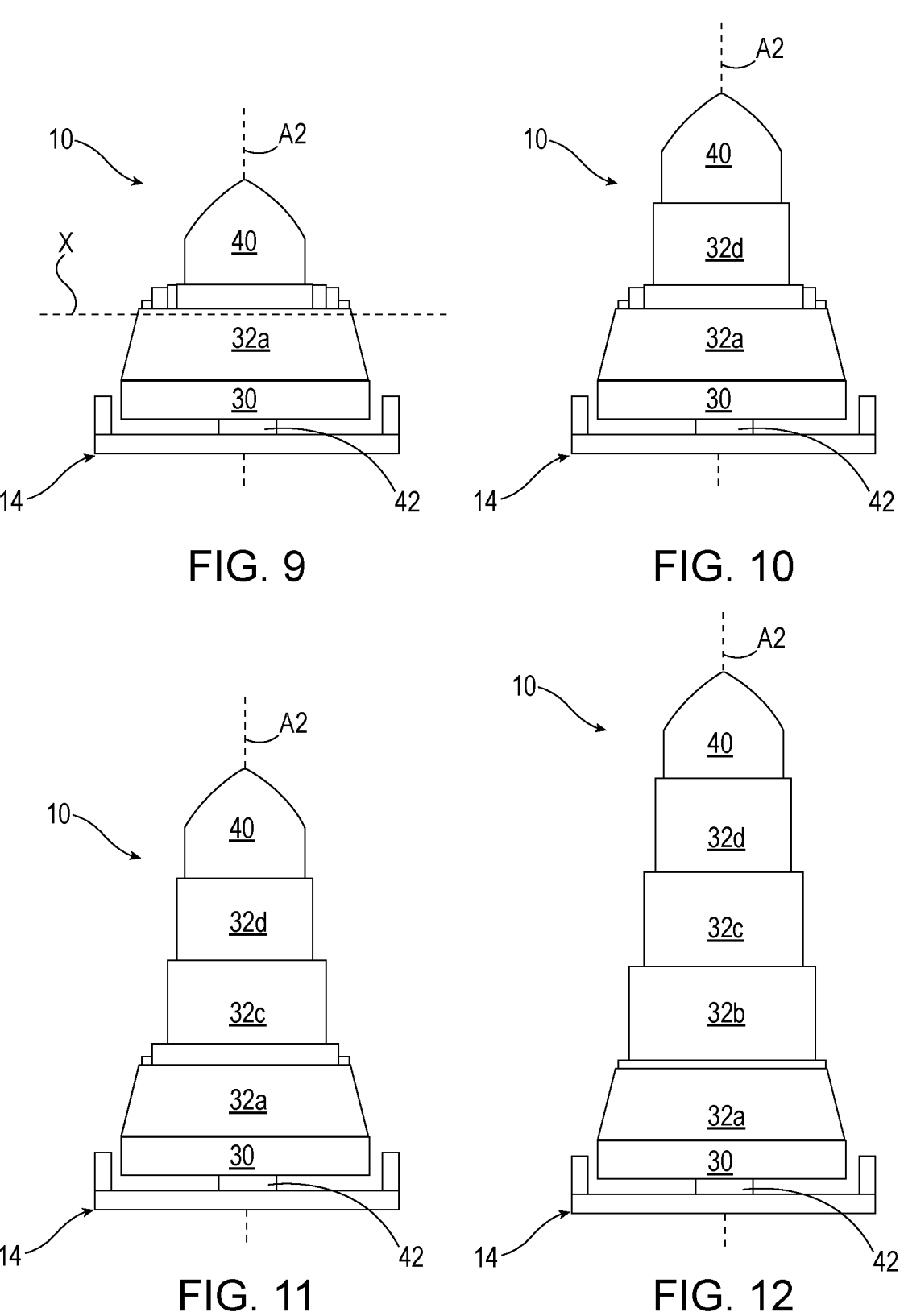
FIG. 9 illustrates the surgical device in a first stage of its transition from a collapsed state into an expanded state.
FIG. 10 illustrates the surgical device in a second stage of its transition from a collapsed state into an expanded state.
FIG. 11 illustrates the surgical device in a third stage of its transition from a collapsed state into an expanded state.
FIG. 12 illustrates the surgical device in a fourth stage of its transition from a collapsed state into an expanded state.

FIGS. 6 and 9-12 illustrates an embodiment including the expansion of one embodiment from the collapsed state (FIG. 6) into the expanded state (FIG. 10) when the clutch may be in the locked position (and the base 30 does not rotate). In the embodiment shown, in FIG. 9, when the power source (not shown) may be supplying rotative power, the track assembly 14 permits the shaft 42 to rotate about the second axis A2. When the clutch 18 may be engaged and in a locked position, continued rotation of the shaft 42 causes the superior engagement segment 40 to rotate and advance upwardly, as shown in FIG. 9. In one embodiment, once the superior engagement segment 40 may be in its final position, the fourth engagement segment 32d, as shown in FIG. 10, begins it rotation upward in the proximal direction. Once the fourth engagement segment 32d may be in its final position, the third engagement segment 32c, as shown in FIG. 11, begins its rotation upward. Once the third engagement segment 32c may be in its final positions, the second bone engagement segment 32b, as shown in FIG. 12, begins its rotation upward in the proximal direction. In this way, each bone engagement segment moves independently and in sequence once advancement of a proximal bone engagement segment may be complete, until a final desired height of the expandable surgical device 12 may be attained, as shown in FIG. 12.

In other embodiments, engagement sections 32 rotate upward at the same time as one another. In other embodiments, the engagement sections 32 may rotate upward respective to adjacent segments until a stop element is reached.

Figure 13:
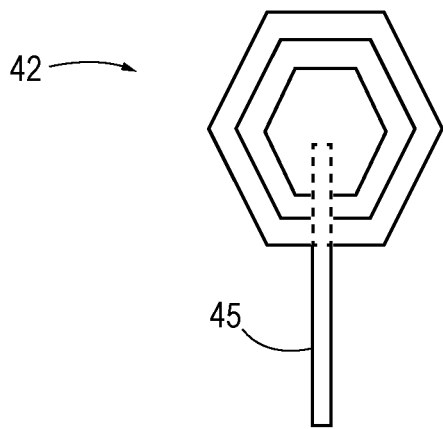
FIG. 13 is a top view of an expandable shaft used in the surgical device shown in FIGS. 1-12.
Figure 14:
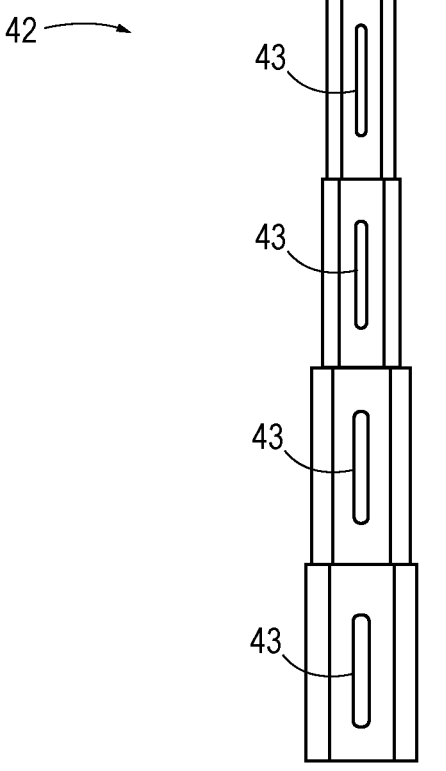
FIG. 14 is a side view of the expandable shaft shown in FIG. 13.

FIGS. 13 and 14 illustrate an embodiment of an expandable drive shaft 42 used in the surgical device 12. The expandable drive shaft 42 may include multiple drive shaft segments that correspond to the bone engagement segments described above. In one embodiment, each drive shaft segment may include a slot 43. The slots 43 of each drive shaft segment may be aligned with each other when the drive shaft segments 42 may be fully collapsed. In this way, an engagement rod 45 can be engage one or more of the slots 43 to inhibit rotation of the draft shaft segments. The engagement rod 45 can be selectively removed or reinserted to lock rotation of the segments but may be also rotatable along with the draft shaft 42. In certain embodiments, the engagement rod may be a spoke or cog as needed. The shaft 42 may be unitary and non-telescoping, and translates as the surgical device 12 expands. The bone engagement segments may be generally circular in cross-section and may be nested together in a collapsed state.

In other embodiments, only the superior engagement segment 40 is driven, and superior engagement segment 40 rotates until its stop element of its outer threads 48 engage, at which point both superior engagement segment 40 and fourth engagement segment 32d are caused to rotate together by nature of the stop element not permitting relative movement between fourth engagement segment 32d and superior engagement segment 40. When the stop element of outer threads 46d of fourth engagement segment 32d engages, fourth engagement segment 32d, superior engagement segment 40 and third engagement segment 32c rotate together by nature of two stop elements not permitting relative movement between such elements, and so forth. In this embodiment, at first only superior engagement segment 40 is driven, and then each sequential distal engagement segment is driven in sequence as each sequential distal engagement segment engages its stop element, until at one point superior engagement segment 40 and all engagement segments 32 are driven simultaneously.

Figure 15:
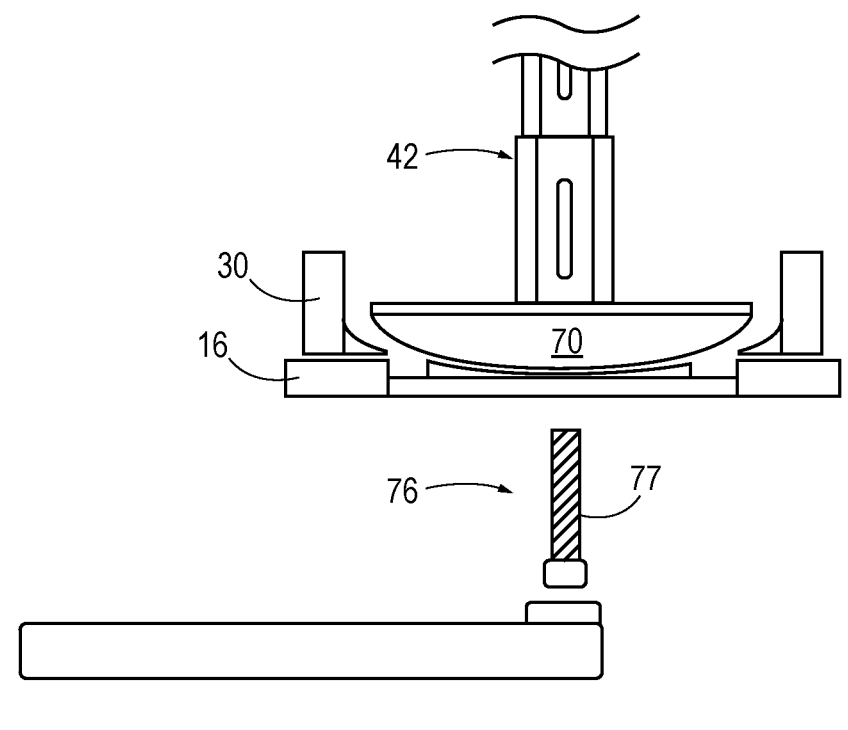
FIG. 15 is a side schematic view of a mechanism used to expand and/or rotate the surgical device shown in FIGS. 1-14.
Figure 16A:
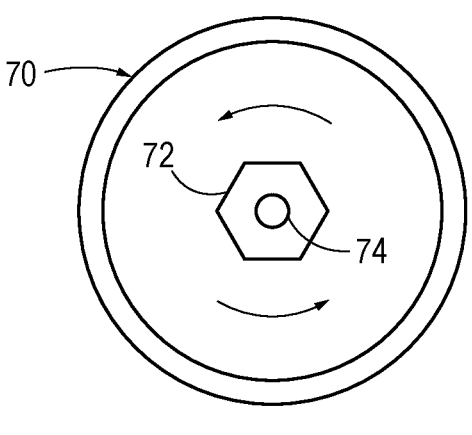
FIG. 16A is a top view of a disc used in the mechanism shown in FIG. 15.
Figure 16A:
Figure 16B:
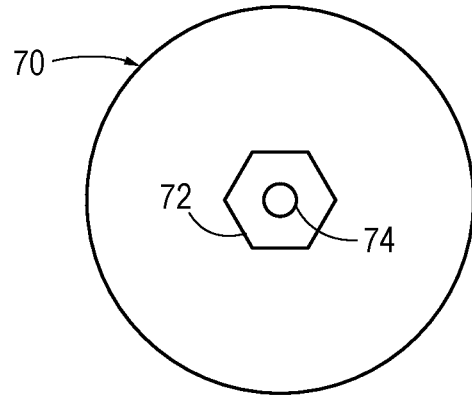
FIG. 16B is a bottom view of the disc shown in FIG. 16A.

The embodiments of FIGS. 15-16B illustrate an embodiment of a mechanism for engaging the base 30 carried by the tray 16. The mechanism may include an articulating disc 70 having an upper surface and a curved lower surface. The disc 70 may include a first engagement feature 72 configured with the hex shape as shown and a second engagement feature 74 configured as a thread bore. A screw 76 may include a head and shaft 77. The head may include a shape configured to mate with the first engagement feature 73 of the disc. The shaft 77 may be threaded to engage the second engagement feature 74, e.g. the threaded bore.

In certain embodiments, all of the bone engagement segments and drive shaft segments rotate together to, for example, ream or position the surgical device in the desired position. For the proximal most segment to rotate or expand upwardly, then the remaining outer bone engagement segments stop rotating while the inner segments rotate and extend upwardly.

In some embodiments, the surgical device may be configured such that none of the bone engagement segment or drive shaft segments may be locked so that rotation may be uninhibited. However, the surgical device may be configured to lock all of the segments (bone engagement and drive shaft segments) to ream the tibial space as needed. In this embodiment, the engagement rod 45 may be extended through the slots of the drive shaft all the way toward the center of the surgical device. Here, the engagement rod or spoke rotates with the construct. The engagement rod can be selectively removed from the slots of the inner draft shaft while the inner drive shaft rotate.

In one embodiment, the surgical device can be removed by reverse rotation to thread out of the tibial space. Alternatively, the user can disengage the head and turn while locking each component from rotation, which allows removal of the surgical device as needed.

Figure 17:
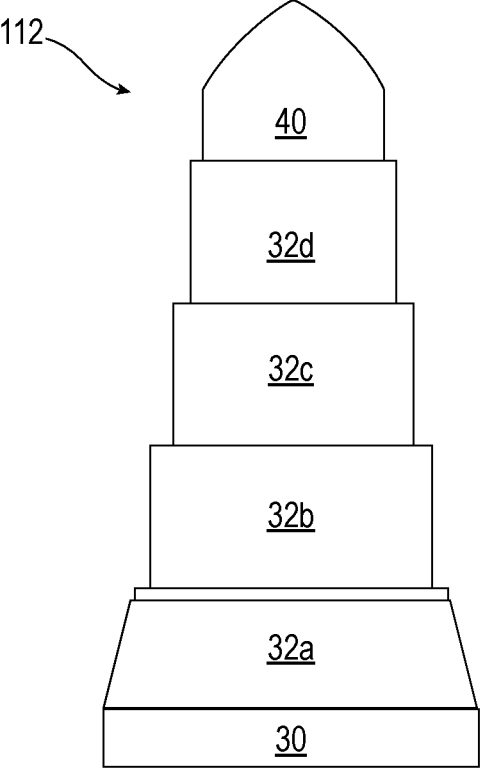
FIG. 17 illustrates the surgical device could be configured as an implant, with the track assembly removed.

FIG. 17 illustrates an embodiment of a system 110 whereby the expandable surgical device 12 may be configured as a tibial reaming implant 112. In other words, the expandable tibial implant 112 may be configured as both a reamer and an implant. This, in turn, removes the need to ream the tissue beforehand so that the user can both ream and implant the tibial implant 112 in a single operation. The system 110 may include a distal implant configured to engage at least a talus bone. The distal implant may include a lower surface that engages talus bone and an upper surface configured to movably engage a bottom surface of the tibial implant.

Figures 18, 19:
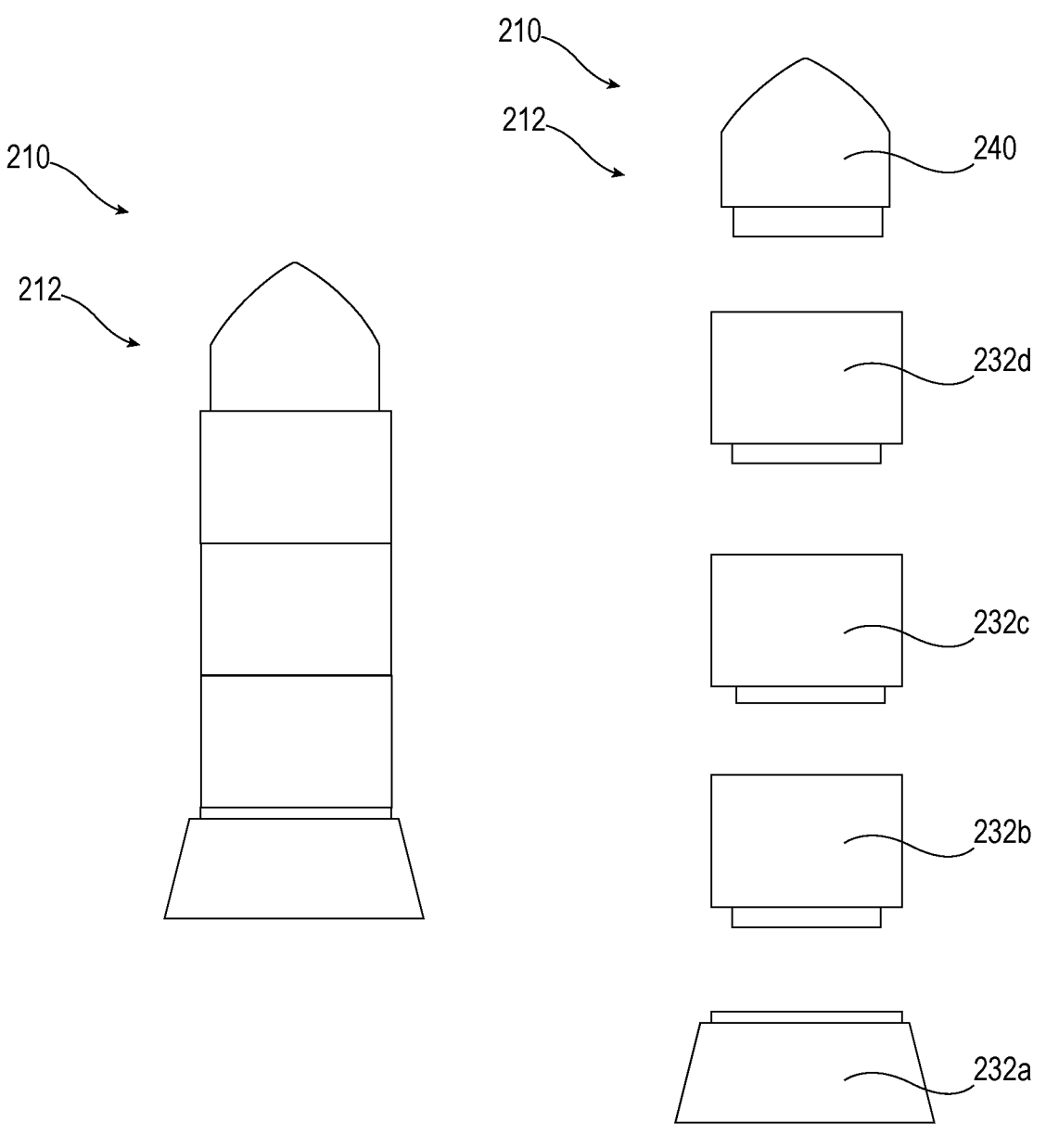
FIG. 18 illustrates an embodiment of an implant that includes multiple modular segments, which could be used after the reamer shown in FIGS. 1-12 prepares the site.
FIG. 19 illustrates an embodiment of an implant that includes multiple modular segments, which could be used after the reamer shown in FIGS. 1-12 prepares the site.
Figure 20:
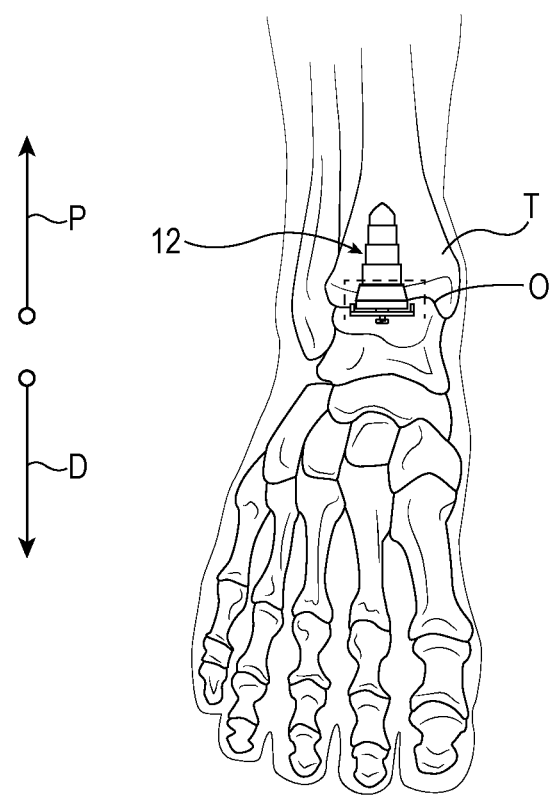
FIG. 20 illustrates the reamer/implant in the ankle joint in a fully expanded state.
Figure 21:
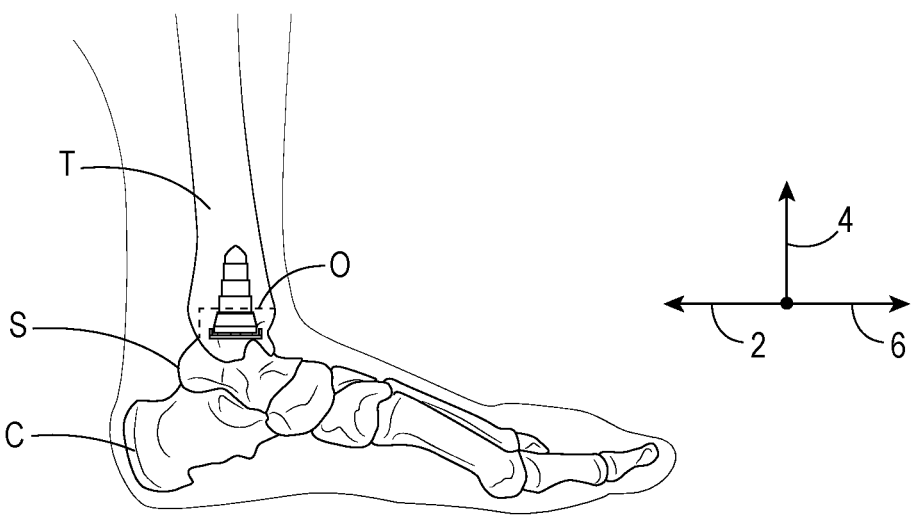
FIG. 21 illustrates the reamer/implant in the ankle joint in a fully expanded state.

FIGS. 18 and 19 illustrate another embodiment of a surgical system 210 including an expandable surgical device 12 configured as a reamer to prepare tissue, and a modular tibial implant 212, and an optional distal implant (not numbered or shown). In the embodiment shown in FIGS. 18 and 19, once the interior portion of the tibia may be reamed with the expandable surgical device 12 as described above, the modular tibial implant 212 may be then inserted into the tibia. The tibial implant 212 may include a plurality of connectable bone engagement segments 232a-232d, 40. Each connectable bone engagement segment 232a-232b and 40 may be configured to be separately inserted into the prepared space and selectively engage an adjacent bone engagement segment in the interior portion of the tibia. The system 210 may include a distal implant configured to engage at least a talus bone. The distal implant may include a lower surface that engages talus bone and an upper surface configured to movably engage a bottom surface of the tibial implant.

In certain embodiments, the system 10, 110, 210 may be used to prepare or treat an ankle joint. As shown in FIGS. 1 and 2 and FIGS. 20 and 21, the method may include forming an insertion site O in an anterior portion of a distal end of a tibia Tor going directly through the distracted ankle joint. Then, a user may insert the expandable surgical device 12, in a collapsed state, into the insertion site O in a posterior direction 4. At this point, the device 12 does not engage the talus or calcaneus bone as the approach may be anterior as opposed to inferior. Next, with the expandable surgical device 12 in the insertion site O, the user increases a height of the expandable surgical device 12 into an expanded state, in a superior direction 4 that may be perpendicular to the posterior direction 2, to engage an interior portion of the tibia T.

In certain embodiments, increasing the height of the surgical device 12 may be accomplished by rotating the expandable surgical device 12 about an axis A2 that may be aligned with the superior direction 4. This in turn, may require rotation of a shaft 42 that may be coupled with the expandable surgical device 12. Then, a user can engage a clutch 18, or insert a cog or spoke through perforations in the device, which inhibits rotation of the base, but permits rotation of the bone engagement segments, in sequence, as described above, which increases the overall height of the device 12 in the tibial space. In one embodiment, initial engagement of the clutch causes the base to stop rotation but permits the superior bone engagement segment 40 to rotate relative to 1) the base, and 2) the remaining bone engagement segments 32, which allows the superior bone engagement segment 40 to expand in the superior direction relative to the base.

In some embodiments, during rotation of the shaft and bone engagement segments, the bone engagement segments rotate and expand in a superior or proximal direction until a bone engagement segment engages a stop element. The stop element may inhibit further rotation of the bone engagement segment while permitting an inferiorly positioned bone engagement segment to rotate and thus expand in a superior direction.

Figure 22A:
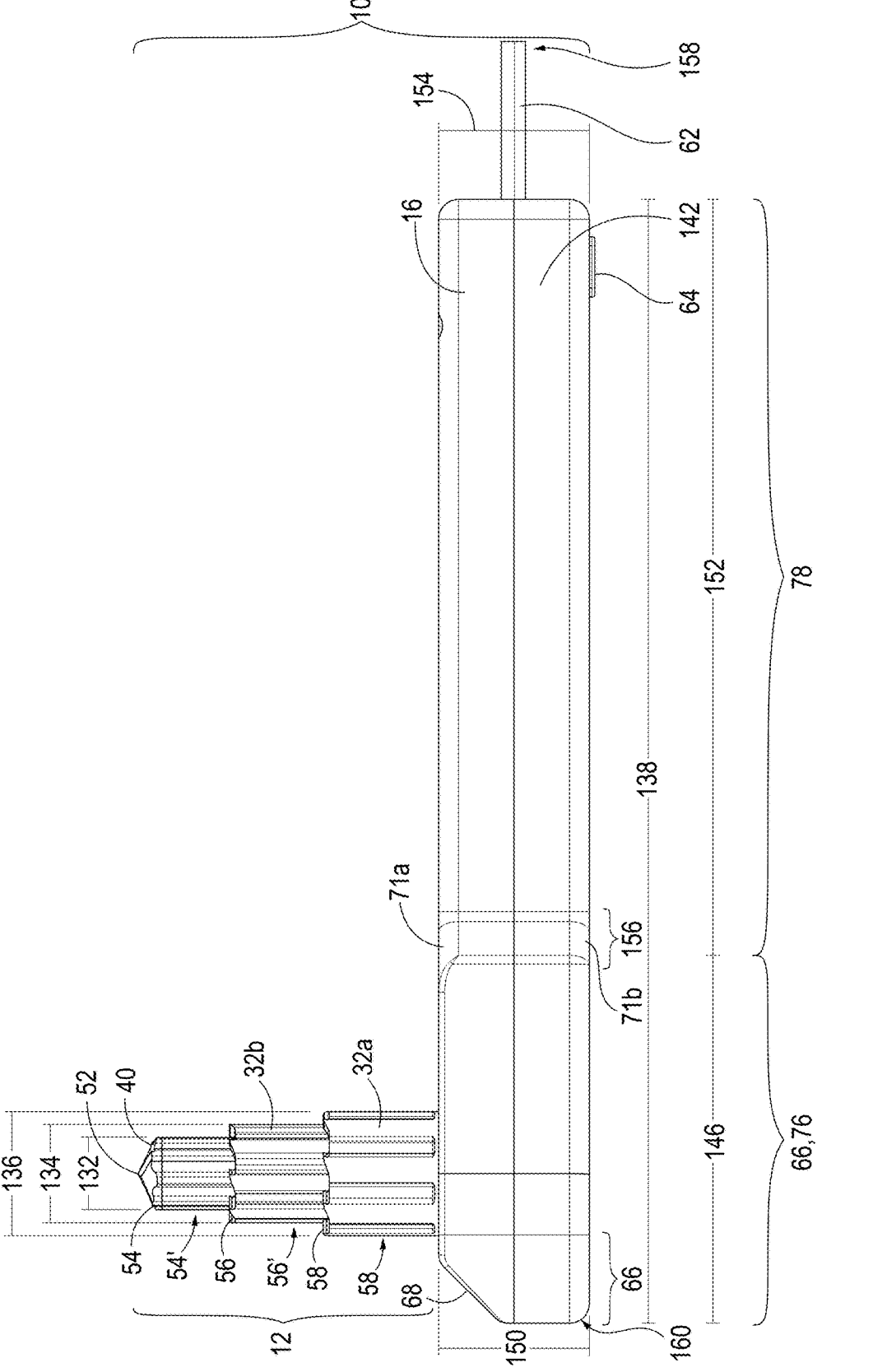
FIG. 22A is a side views of embodiments of a housing and reamer.
Figure 22B:
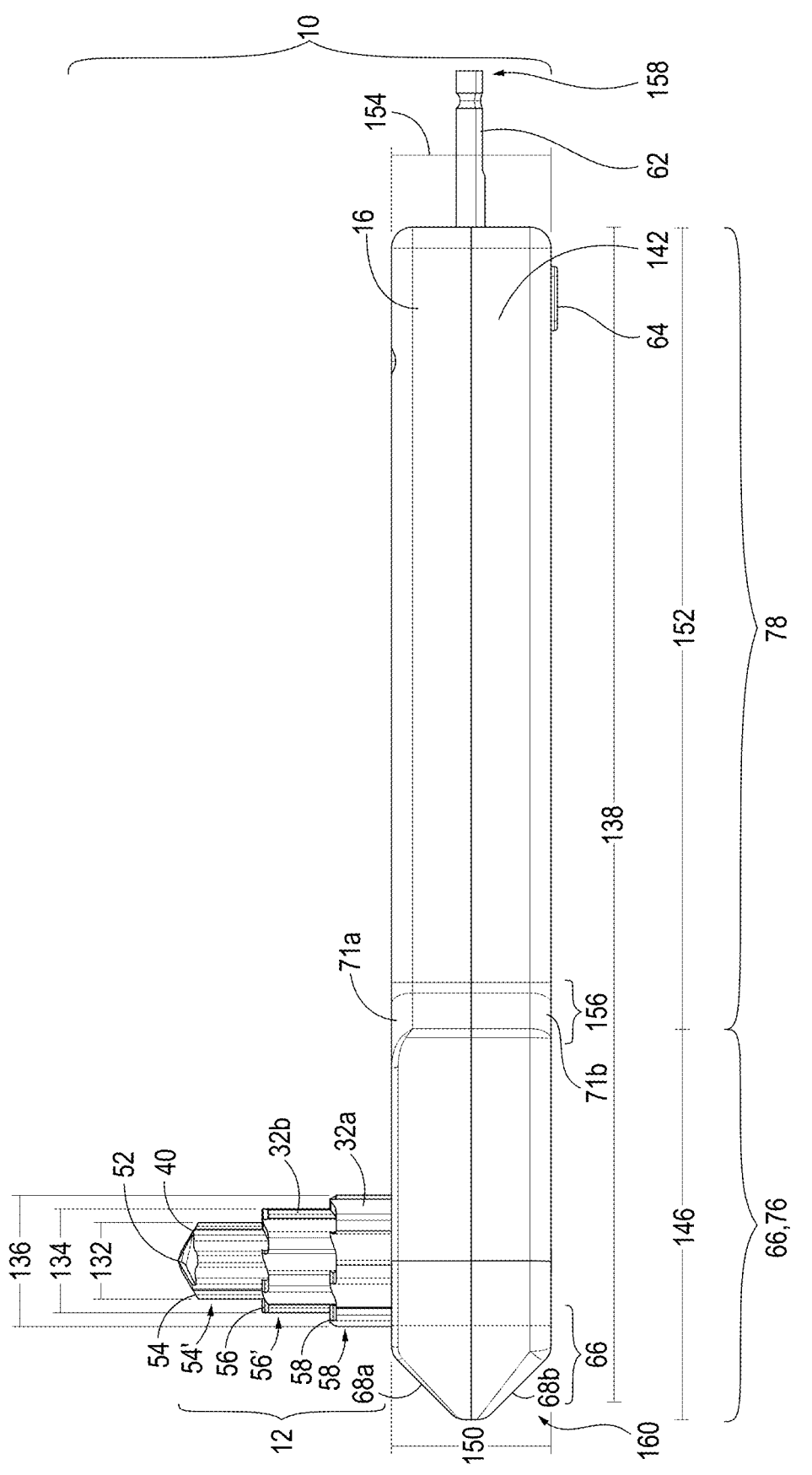
FIG. 22B is a side view of embodiments of a housing and reamer.

In embodiments, as shown in FIG. 22, the surgical system may include a reamer 12 and an implant 200. The reamer 12 may include a first reamer component 40, a second reamer component 32b, and a third reamer component 32a. The first reamer component 40 may include any suitable cross-sectional shape, including but not limited to a substantially circular cross-sectional shape, a substantially rectangular cross-sectional shape, and a substantially irregular cross-sectional shape. The first reamer component 40 may include a first substantially circular cross-sectional shape with a first reamer circumference 132. The second reamer component 32b may include any suitable cross-sectional shape, including but not limited to a substantially circular cross-sectional shape, a substantially rectangular cross-sectional shape, and a substantially irregular cross-sectional shape. The second reamer component 32b may include a second substantially circular cross-sectional shape with a second reamer circumference 134. The third reamer component 32a may include any suitable cross-sectional shape, including but not limited to a substantially circular cross-sectional shape, a substantially rectangular cross-sectional shape, and a substantially irregular cross-sectional shape. The third reamer component 32a may include a third substantially circular cross-sectional shape with a third reamer circumference 136. The second reamer component 32b may be configured to be disposed between the first reamer component 40 and the third reamer component 32a. In certain embodiments, first reamer component has a circular cross-section and nests within second reamer component 32b, and second reamer component 32b has a circular cross-section and nests within first reamer component 32a, which also has a circular cross-section.

In embodiments, the reamer components 40, 32a-b may include surface elements (not shown) configured to facilitate removal of bone shavings, including but not limited to openings, pores, and channels.

II. Reamer Housing

In embodiments, as shown in FIGS. 22-27, 46A-46B, the surgical device 10 may include a housing 16, a reamer 12, and an adjustment mechanism 100. The housing 16 may include a longitudinal length 138 disposed along a first axis A. The housing 16 may include at least one location feature 73, 74 disposed on the longitudinal length 138. The housing 16 may include a track assembly.

In embodiments, as shown in FIGS. 22-27, the at least one location feature 73, 74 may be configured to facilitate orientation of the reamer 12 with respect to the patient's intramedullary canal. The at least one location feature 73, 74 may include an indicator 73, 74 along a width 140 or partial width of the housing 16 along a third axis D. The third axis D may be substantially perpendicular to the first axis A. The at least one location feature 73, 74 may include any suitable feature, including but not limited to a marking on the housing, at least one notch, at least one stop mechanism, at least one radiopaque element, at least one locking element, and at least one auditory element. In embodiments, the housing 16 may include at least two or more location features 73, 74 disposed along the longitudinal length 138.

In embodiments, as shown in FIGS. 26-27, 46A-46B, the housing 16 may include a first lateral side 142 and a second lateral side 144. The adjustment mechanism 100 may include a first arm 122 and a second arm 124. The first arm 122 may be disposed proximally to the first lateral side 142. The second arm 124 may be disposed proximally to the second lateral side 144. The first arm 122 and the second arm 124 may be configured to slide along the first lateral side 142 and second lateral side 144, respectively. A housing receiving channel 170 may be disposed between the first arm 120 and the second arm 122. The first arm 120 and the second arm 122 may each include a traverse opening 172. The traverse opening 172 of the first arm 120 and the second arm 122 may be configured to receive a traverse fixation element (not shown), for example, a fastener, including but not limited to a bolt and a nut. The traverse fixation element may be configured to secure the adjustment mechanism 100 to the housing 16 in a desired position.

Figure 26:
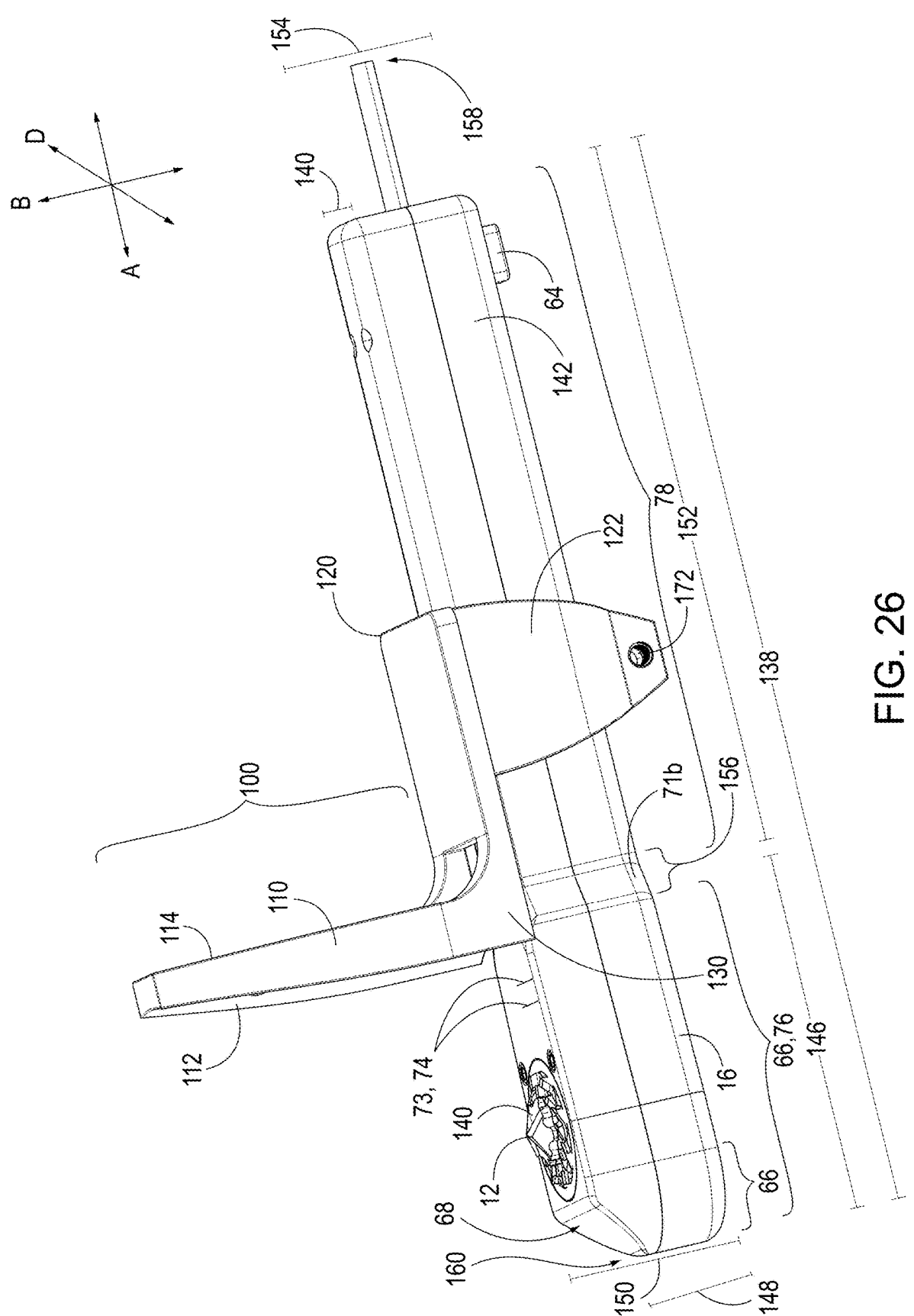
FIG. 26 is a perspective view of an embodiment of a housing, a reamer, and an adjustment mechanism.
Figure 27:
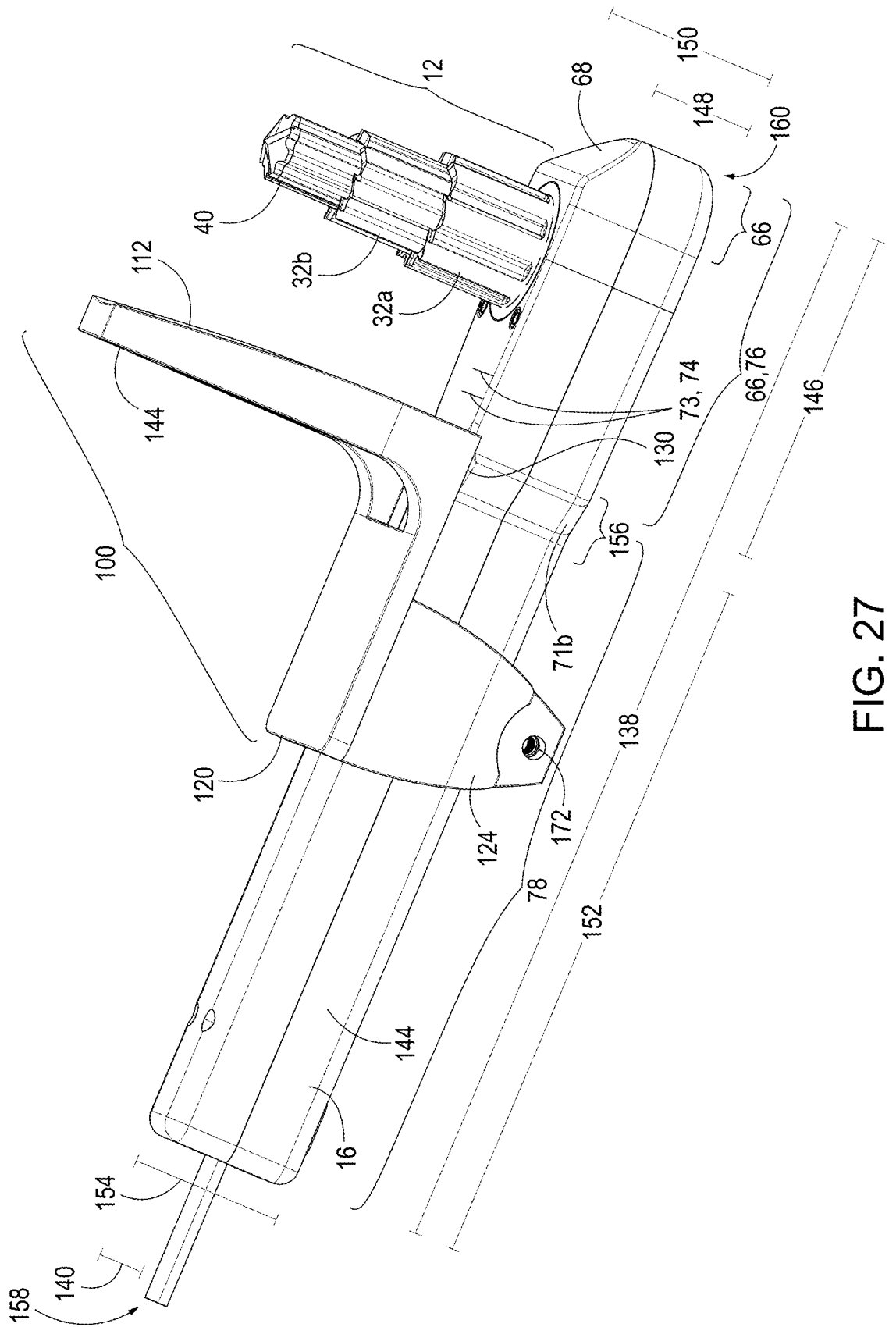
FIG. 27 is a perspective view of an embodiment of a housing, a reamer, and an adjustment mechanism.

Referring to the embodiment shown in FIGS. 26-27, the housing 16 may include a first section 76 and a second section 78. The first section 76 may include a reamer housing. The second section 78 may include a handle. The first section 76 may include a first length 146, a first width 148, and a first height 150. The second section 78 may include a second length 152, a second width 140, and a second height 154. The reamer 12 may be disposed within the reamer housing of the first section 76. The first width 148 and the first height 150 may be greater than the second width 140 and the second height 154. The first length 146 may be less than the second length 152. The first height 150 may have any suitable height. The first height 150 may be less than approximately 50 mm. The first height 150 may be between approximately 10 mm and 40 mm. The first height 150 may be between approximately 15 mm and 30 mm. The first height 150 may be between approximately 30 mm. In embodiments, the insertion site O may include a surgical resection site. The surgical resection site may include a surgical resection area. The surgical resection may be a of a patient's ankle joint may include a resection length, a resection width, and a resection height. The resection width may be greater than or equal to the first width 148. The resection length may be greater than or equal to the first length 146. The at least one engagement feature 73, 74 of the housing 16 may be configured to determine how far into the resection length the reamer 12 is configured to be inserted.

The at least one engagement feature 73, 74 of the housing 16 may be configured to orient the reamer 12 to align with the intramedullary canal of the patient's tibia. In one embodiment, the at least one engagement feature 73, 74 of the housing 16 may be configured to orient the reamer 12 to align with a leading edge of the patient's tibia when being inserted into the surgical resection site.

In embodiments, as shown in FIGS. 22-25, the housing 16 includes a patient proximal section 66. The patient proximal section 66 may include a nose. The patient proximal section 66 may be part of the first section 76. The patient proximal section 66 may include a ramped face 68. The patient proximal section 66 may include two ramped faces 68a, 68b. The patient proximal section 66 may be configured to facilitate positioning of a portion of the first section 76 of the housing within the surgical resection site, as the housing 16 is first being inserted into the surgical resection site.

In embodiments, as shown in FIGS. 22-25, the housing 16 may include an intermediate section 156. The intermediate section 156 may be disposed between the first section 76 and the second section 78. The intermediate section 130 may include at least one ramp face 71a, 71b. The intermediate section 130 may include a superior ramp face 71a and an inferior ramp surface 71b.

Referring to FIGS. 22-25, In embodiments, the housing 16 may include a shaft 62. The shaft 62 may be oriented substantially parallel to the first axis A. The housing 16 may include a patient distal end 158 and a patient proximal end 160. The shaft 62 may be configured to be engaged by a power driver (not shown) through an interface between the power driver and the shaft 62.

Figure 23:
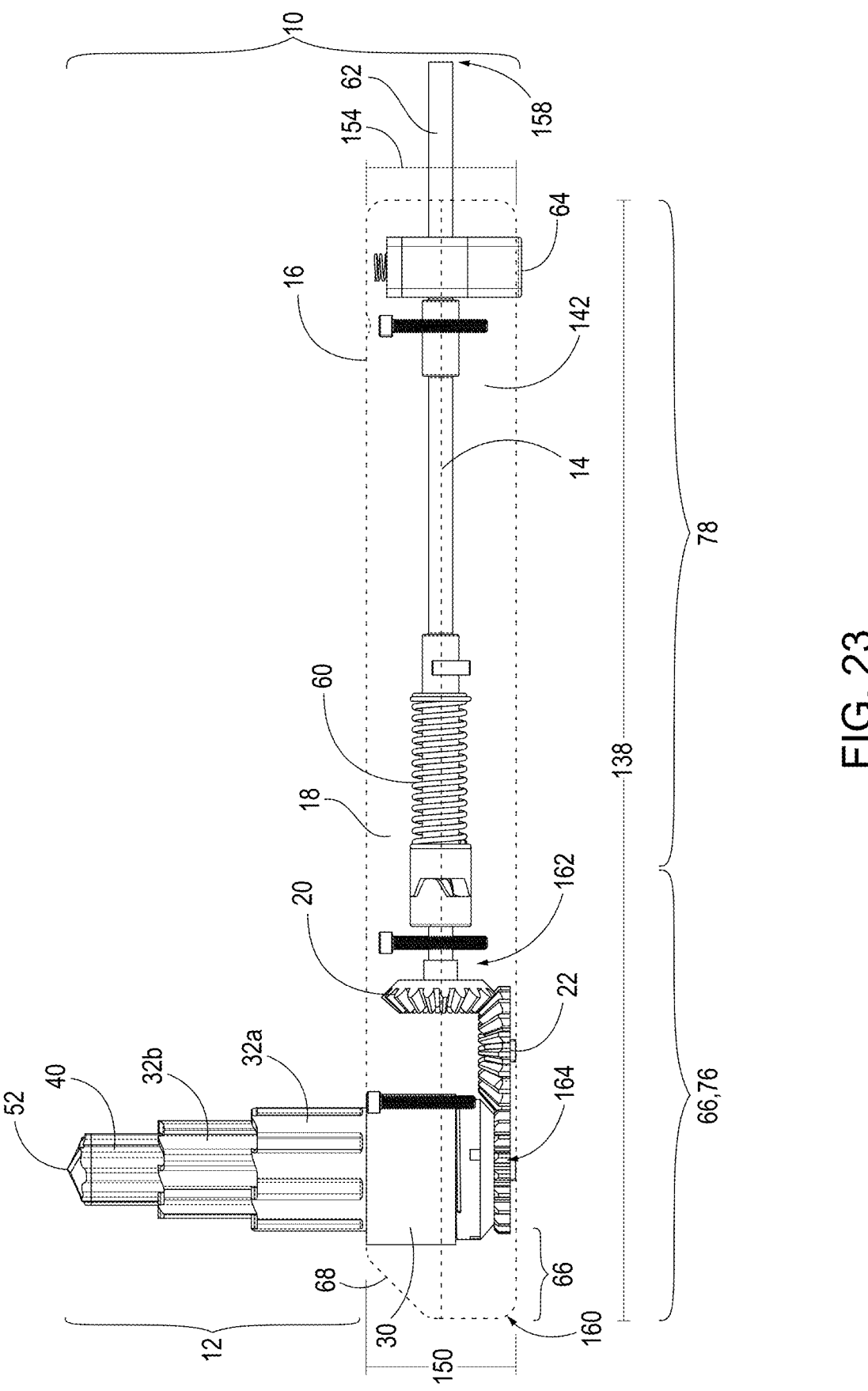
FIG. 23 is a transparent side view of an embodiment of a housing and reamer.
Figure 24:
FIG. 24 is a transparent side view of an embodiment of a housing and reamer.
Figure 25:
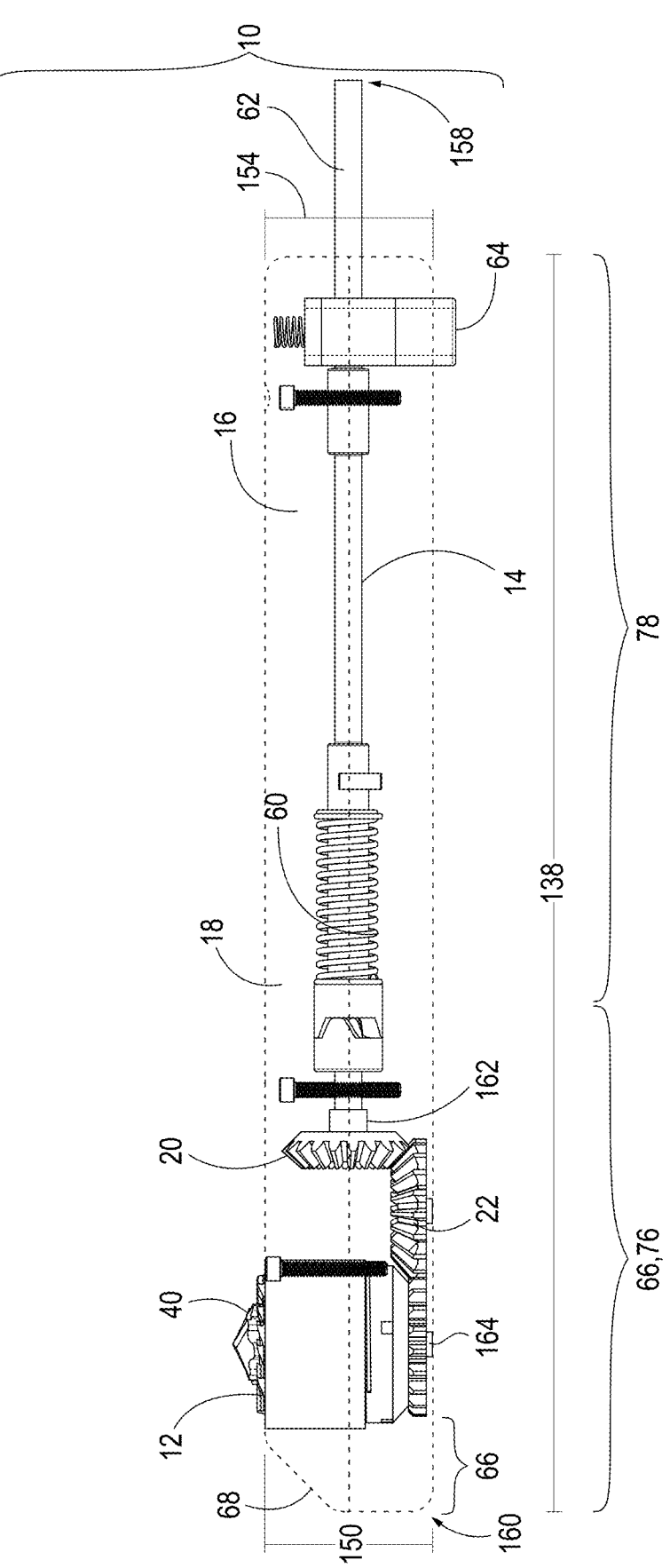
FIG. 25 is a transparent side view of an embodiment of a housing and reamer.

In embodiments, as shown in FIGS. 23-25, the housing 16 may include a first gear 20 and a second gear 22. The reamer 12 may include a plurality of nested reamer elements 32a-b, 40, 30. The shaft 62 may be configured to engage the power driver at the patient distal end 158. The shaft 62 may be configured to engage the first gear 20 at a first location 162 within the housing 16 disposed between the patient proximal end 160 and the patient distal end 158. The second gear 22 may be configured to engage the first gear 20 at a second location 164 within the housing disposed between the patient proximal end 160 and the first location 162. The second gear 22 may be configured to engage the reamer 12 at a third location 164 within the housing 16 disposed between the patient proximal end 160 and the second location 162. Rotation of the shaft 62 may be configured to cause rotation of the first gear 20 and the second gear 22. The first gear 20 may be oriented perpendicularly to the axis of shaft 62 such that rotation of the shaft 62 causes rotation of the first gear 20 with an axis of rotation perpendicular to the axis of rotation of shaft 62. The second gear 22 may be oriented substantially perpendicularly to the first gear 20 such that rotation of the first gear 20 causes rotation of the second gear 22 with an axis of rotation perpendicular to the axis of rotation of the first gear 20. In embodiments, the first gear 20 and the second gear 22 may comprise bevel gears or miter gears. The first gear 20 and second gear 22 may include gear teeth that engage one another to accomplish rotation. Rotation of the first gear 20 and the second gear 22 may be configured to cause rotation of the reamer 12. The reamer 12 may include a gear engagement feature (not shown) such that rotation of the second gear 22 while the second gear 22 and reamer 12 are engaged causes rotation of the reamer 12. The gear engagement feature may include any suitable element, including a gear, for example parallel axis gears or spur gears. The gear of the gear engagement feature may include teeth configured to engage the teeth of the second gear 22. Rotation of the reamer 12 may be configured to cause expansion of the plurality of nested reamer elements 40, 32a-b, 30.

In embodiments, as shown in FIGS. 23-25, the housing 16 may include a clutch 18. The clutch 18 may serve to allows the first gear 20 to be disconnected from shaft 62. The clutch 18 may include a spring 60. The housing 16 may include a release feature 64. The release feature 64 may include a button. The release feature 64 may include any other suitable element, including but not limited to a switch, a grip element, and a lockout element. When the shaft 62 is driven by the power source (not shown), the clutch 18 may be engaged, causing the first gear 20 to rotate. In embodiments, spring 60 may exert a force on the clutch, forcing the shaft 62 into engagement with the first gear 20, and activating clutch 18 may cause compressive force on the spring 60, disengaging shaft 62 and first gear 20. The clutch 18 may be configured to reach a maximum torque, causing the spring 60 to be compressed and stop application of rotational force to the first gear 20, which in turn may disengage shaft 62 and first gear 20, which in turn may stop application of rotational force to the reamer 12. The release feature 64 may be configured to be used when the clutch 18 fails to disengage shaft 62 and first gear 20. In alternative embodiments, the release feature 64 may be configured to be pressed prior to engaging the shaft 62 with the power source 26. In such embodiments, the shaft 62 may be unable to rotate without engaging release feature 64. The release feature 64 and the shaft 62 may be configured to be engaged with a collet (not shown), or some other element to hold shaft 62 disengaged from first gear 20 against the force of the spring 60.

In embodiments, as shown in FIG. 22A, the reamer 12 may be disposed entirely within the housing 16 when in a collapsed state. The reamer elements 30, 32a-b, 40 may be provided in a collapsed state in which the reamer elements 30, 32a-b, 40 are nested together within the housing 16. In embodiments, the reamer 12 may be disposed at least partially within the housing 16. The reamer 12 may be provided entirely within the housing 16 at a first, collapsed height. The first, collapsed height, measured from the housing 16, may be approximately 0 mm to 15 mm. The reamer 12 may be configured to expand to a second, expanded height. The second, expanded height may be approximately 5 mm to 200 mm. The second, expanded height may be approximately 10 mm to 100 mm.

In embodiments, as shown in FIGS. 22-27, the reamer 12 may be oriented substantially perpendicularly to the longitudinal length 138 of the housing 16. In other embodiments, the reamer 12 may be oriented at an angle less than or equal to 10° when measured from the longitudinal length 138 of the housing 16.

In embodiments, as shown in FIGS. 22-27, the plurality of nested reamer elements 40, 32a-b, 30 may include a head reamer element 40, at least one intermediate reamer element 32a-b, and a base reamer element 30. The head reamer element 40 and the at least one intermediate reamer element 32b may include cutting elements, 54', 56', 58'. The cutting elements, 54', 56', 58' may be disposed on the leading faces 54, 56, 58.

In embodiments, as shown in FIG. 24, the reamer 12 may include an advancement element 174. The advancement element 174 may include any suitable element, including but not limited to at least one spring and at least one shaft 42. The advancement element 174 may be configured to be engaged directly or indirectly by the second gear 22. Engagement by second gear 22 may be configured to cause rotation of the advancement element 174. Rotation of the advancement element 174 may be configured to rotate the plurality of nested reamer elements 40, 32a-b. Rotation of the plurality of nested reamer elements 40, 32a-b may cause distal advancement of the plurality of nested reamer elements 40, 32a-b. Distal advancement of the plurality of nested reamer elements 40, 32a-b may be configured in any suitable order. In one embodiment, the advancement element 174 may drive head reamer element 40 to be advanced first. Then, when head reamer element 40 is fully advanced, head reamer element 40 may engage with intermediate reamer element 32b, causing intermediate reamer element 32b to rotation and advance. When intermediate reamer element 32b is fully advanced, intermediate reamer element 32b may engage with intermediate reamer element 32b, causing intermediate reamer element 32b to advance.

In embodiments, as shown in FIG. 8, the plurality of nested reamer elements 40, 32a-b may include locking elements 176. The locking elements 176 may be configured to stop distal advancement of a corresponding reamer element 40, 32a-b when a desired distal advancement has been reached. Alternatively, the locking elements 176 may be configured to prevent distal advancement of a corresponding reamer element 40, 32a-b. The locking elements 176 may be configured to allow advancement of only one reamer element 40, 32a-b at a time, and in any order. The locking elements 176 may be configured to prevent advancement of an intermediate reamer element 32a-b such that only non-adjacent reamer elements 40, 32a-b are advanced. For example, one or more locking element 176 may be engagement such that the head reamer element 40 and the base reamer element 32a, are advanced, but the at least one intermediate reamer element 32b remains in a collapsed state.

In other embodiments, the user may be able to selectively advance reamer elements in other sequences. For example, in one embodiment, head reamer element 40 may be advanced first. Once the head reamer element 40 is fully advanced, intermediate reamer element 32b may be locked out such that it does not advance and remains nested within intermediate reamer element 32b, and intermediate reamer element 32a may advance instead, with intermediate reamer element 32b nested inside. In still further embodiments, the plurality of nested reamer elements 40, 32a-b may be distally advanced simultaneously.

In embodiments, as shown in FIGS. 26-27, 46A-46B, the adjustment mechanism 100 may include a first adjustment mechanism face 112 disposed on a second axis B. The first adjustment mechanism face 112 may be configured to contact an anterior surface of a patient's tibia. The adjustment mechanism 100 may be patient specific such that the first adjustment mechanism face 112 is configured to match contours of the anterior surface of the patient's tibia. The adjustment mechanism 100 may be configured to be movably attached to the housing 16 along the longitudinal length 138. In embodiments, as shown in FIGS. 22-27, the first axis A and the second axis B may be substantially perpendicular.

In embodiments, the surgical device 10 may be configured to be connected to the patient's tibia using a plurality of pins (not shown) or any other suitable fixation element(s). The plurality of pins may be configured to affix the adjustment mechanism 100. The adjustment mechanism 100 may include a plurality of pin holes 168. The plurality of pins may include approximately four to six pins. The plurality of pin holes 168 may include at least as may pin holes as the plurality of pins.

In embodiments, the surgical device 10 may be configured to be used without additional guide elements attached to the anterior surface or an inferior surface of the patient's tibia. In other words, no additional guide elements are required to use surgical device 10 to use and/or guide the reamer 12 on the patient's tibia.

In embodiments, as shown in FIGS. 26-27, 46A-46B, the adjustment mechanism 100 may include an adjustment feature 130 configured to orient the adjustment mechanism 100 with respect to the anterior surface of the patient's tibia. The adjustment feature 130 may be configured to interact with the at least one location feature 73, 74 of the housing 16 such that the adjustment mechanism 100 is configured to be positioned in a desirable alignment with the anterior surface of the patient's tibia, as discussed further below.

In embodiments, the present disclosure may include a method of orienting a reamer 12. The method may include providing the reamer 12. The method may include orienting the reamer 12 within a housing 16. The method may include sliding an adjustment mechanism 100 along a longitudinal length 138 of the housing 16 until the adjustment mechanism 100 aligns with a first location feature 73 disposed along the longitudinal length 138 of the housing 16. The first location feature 73 may correspond to a target depth of a patient's tibia. The method may include determining whether the adjustment mechanism 100, when configured to the first location feature 73, aligns with a target location on the patient's tibia.

In embodiments, when the adjustment mechanism 100 is determined not to align with the patient's tibia, the method may include sliding the adjustment mechanism 100 along the longitudinal length 138 of the housing 16 until the adjustment mechanism aligns with a second location feature 74 disposed along the longitudinal length 138 of the housing 16. The method may include determining whether the adjustment mechanism 100, when aligned with the second location feature 74, aligns the reamer 12 with the target location on the patient's tibia.

In embodiments, when the adjustment mechanism 100 may be determined to align the reamer 12 with the target location on the patient's tibia, the method may include locking the adjustment mechanism 100 relative to the first location feature 73 of the housing 16.

In embodiments, the method may include advancing the reamer 12 into an intramedullary canal of the patient's tibia. Advancement of the reamer 12 may include advancement of one or more of a plurality of nested reamer elements 40, 32a-b. Advancement of the reamer 12 may include engaging a shaft 62 with a power source. The shaft 62 may be configured to be rotated by the power source. Rotation of the shaft 62 may be caused by engaging a clutch 18. Engagement of the clutch 18 may cause rotation of a first gear 20, which may cause rotation of a second gear 22. Rotation of the second gear 22 may cause rotation of a advancement element 174. Rotation of the advancement element 174 may cause rotation and distal advancement of one or more of the nested reamer elements 40, 32a-b. The nested reamer elements 40, 32a-b may be advanced one at a time, sequentially or non-sequentially, or simultaneously. If the nested reamer elements 40, 32a-b are advanced one at a time, the head reamer element 40 may be advanced first, then the at least one intermediate reamer element 32b, then the base reamer element 32a. The reamer 12 may be configured such that not all of the reamer elements 40, 32a-b are distally advanced. A locking element 176 may be engaged such that one or more of the nested reamer elements 40, 32a-b are not distally advanced. The clutch 18 may release force on the reamer 12 if the clutch reaches a maximum torque. After the head reamer element 40 has been advanced, the user may be able to check the reamer's 12 position within the intramedullary canal. If the position is proper, the next reamer element 32a-b may be distally advanced. If the position is not proper, the reamer 12 can be repositioned. In embodiments, the method may include removing the reamer 12 from the intramedullary canal of the patient's tibia and inserting an implant 200 into the intramedullary canal.

III. Expandable Implant

Referring to FIGS. 28-33, 35, 38, In embodiments, the surgical implant 200 may include a surgical stem. The surgical implant 200 may include an expandable surgical device. The surgical implant 200 may include at least one stem component 202, 204, 206. The surgical implant 200 may include a plurality of stem components 202, 204, 206. The surgical implant 200 may include a head stem component 202, at least one intermediate stem component 204, a base stem component 206. The surgical implant 200 may include a plurality of intermediate stem components 204. The surgical stem 200 may include a maximum stem height. The maximum stem height may be approximately 5 mm to 200 mm. The maximum stem height may be approximately 10 mm to 100 mm. The at least one stem component 202, 204, 206 may be configured to permit bone in-growth and may include an outer surface with bone in-growth structures, such as pores, holes, apertures and the like.

Figure 32:
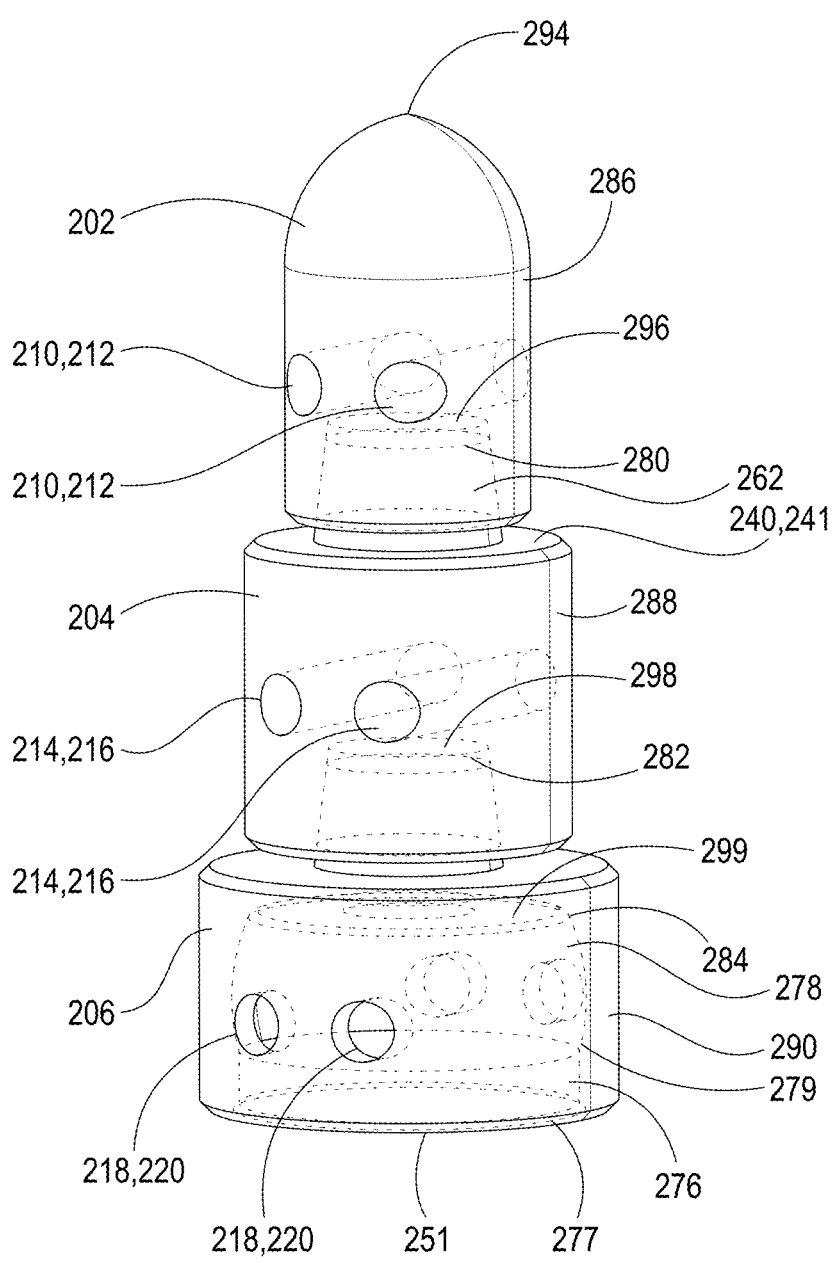
FIG. 32 is a transparent perspective view of an embodiment of a surgical implant.
Figure 33:
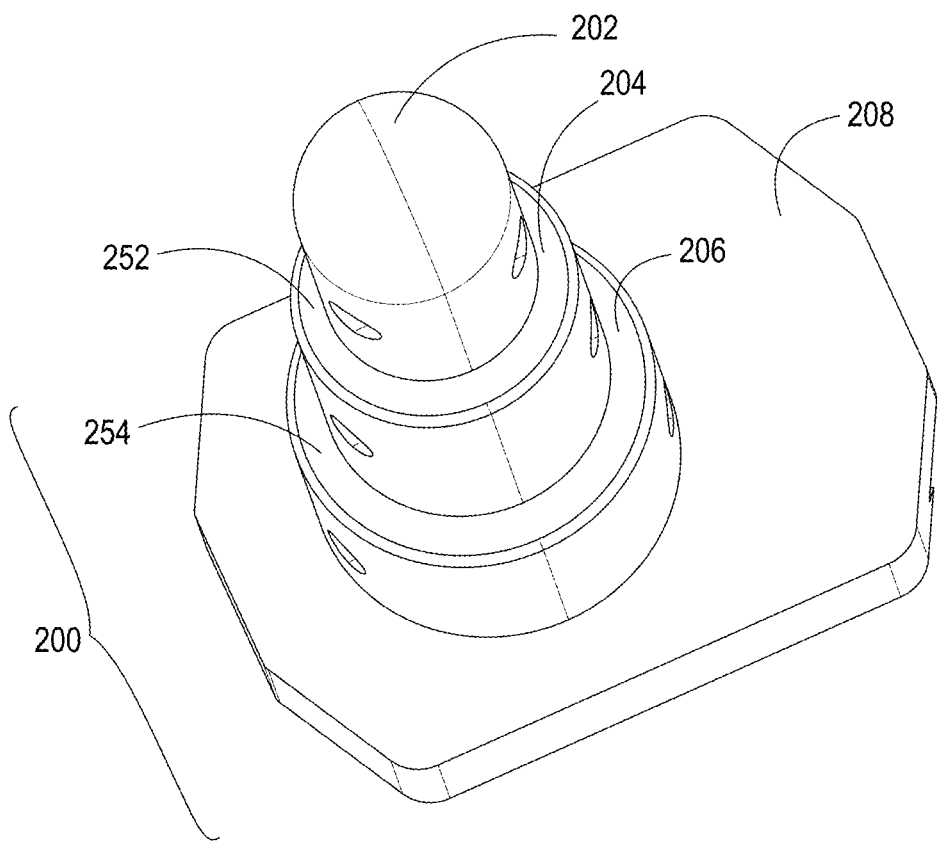
FIG. 33 is a top perspective view of an embodiment of a surgical implant.
Figure 34:
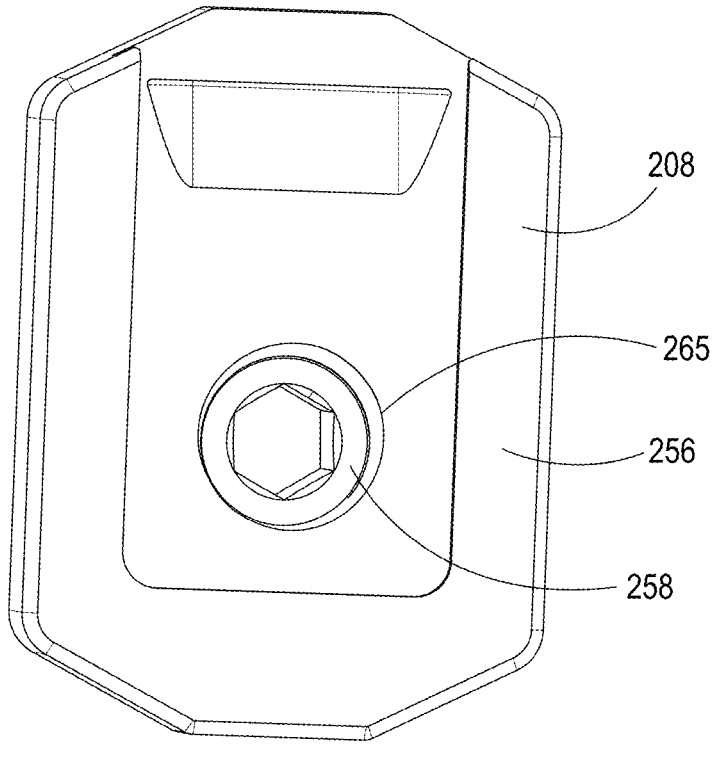
FIG. 34 is a bottom view of an embodiment of a tibial tray.
Figure 35:
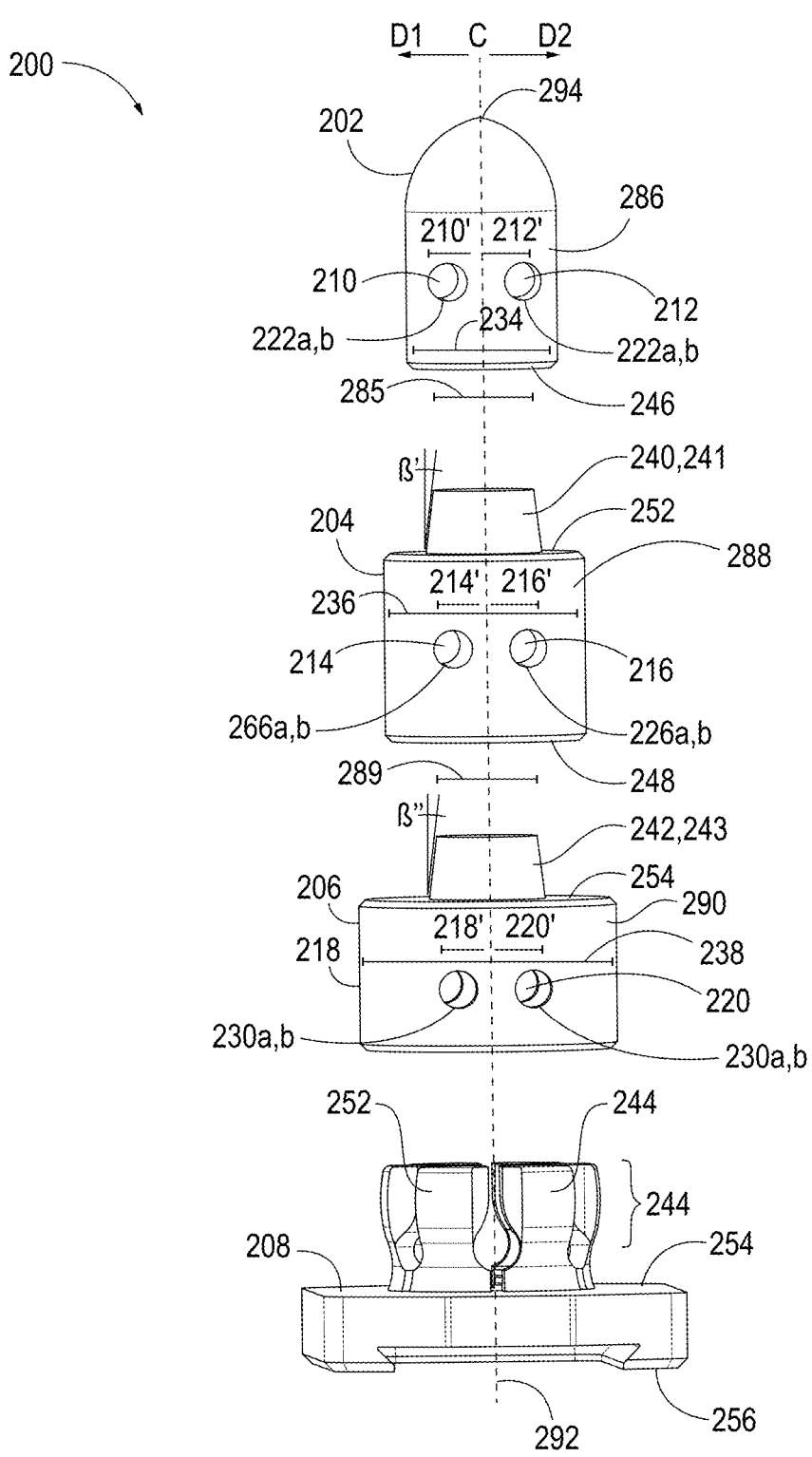
FIG. 35 is an exploded view of an embodiment of a surgical implant.

In embodiments, as shown in FIG. 35, the head stem component 202 may include an inferior face 246. The inferior face 246 may include a recess 280, as shown in FIG. 32. The head stem component 202 may be disposed at a distal end 294 of the implant 200, as shown in FIG. 28.

In embodiments, as shown in FIG. 35, the at least one intermediate stem component 204 may include a superior face 252. The superior face 252 may include an engagement feature 240 projecting therefrom. The engagement feature 240 may include a projection 241. The at least one intermediate stem component 204 may include an inferior face 248. The inferior face 248 may include a recess 282, as shown in FIG. 32.

In embodiments, as shown in FIG. 35, the base stem component 206 may include a superior face 254. The superior face 254 may include an engagement feature 242. The engagement feature 242 may include a projection 243.

Figure 28:
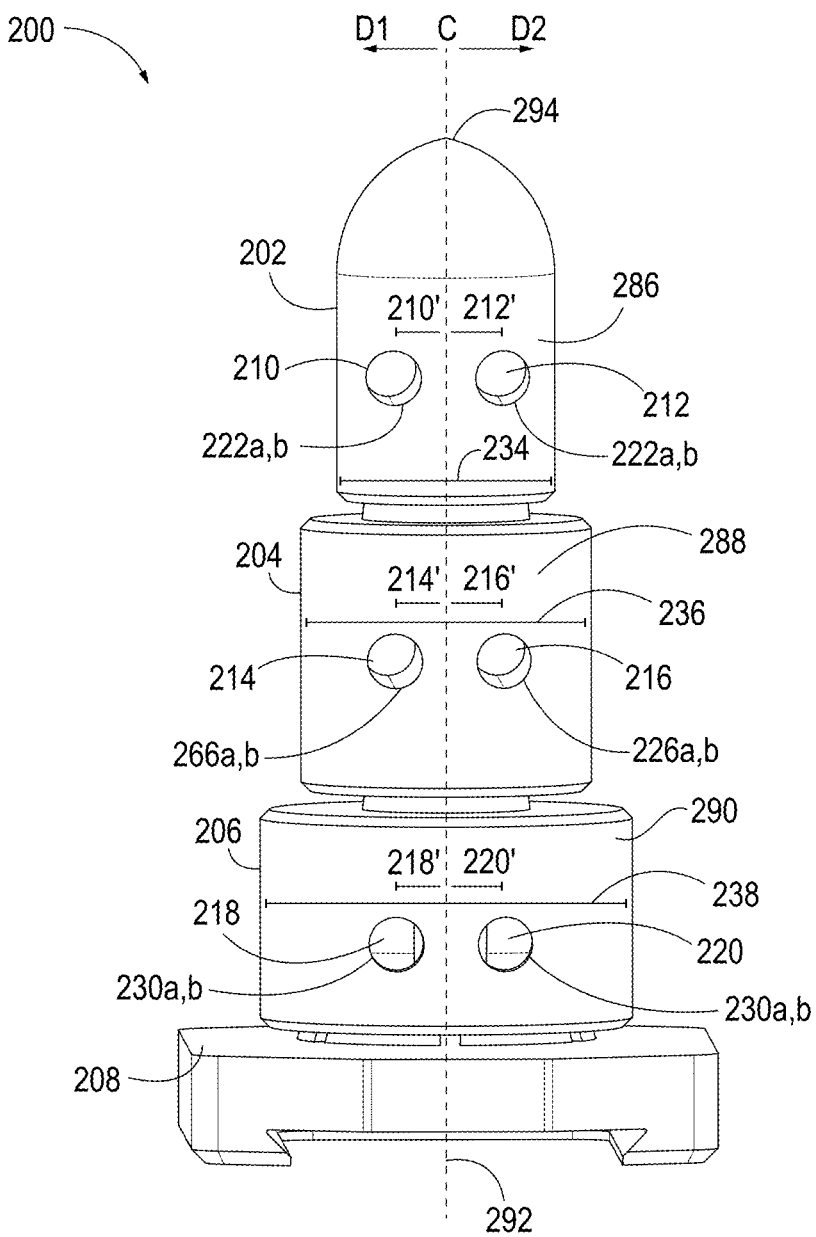
FIG. 28 is a front view of an embodiment of a surgical implant.
Figure 29:
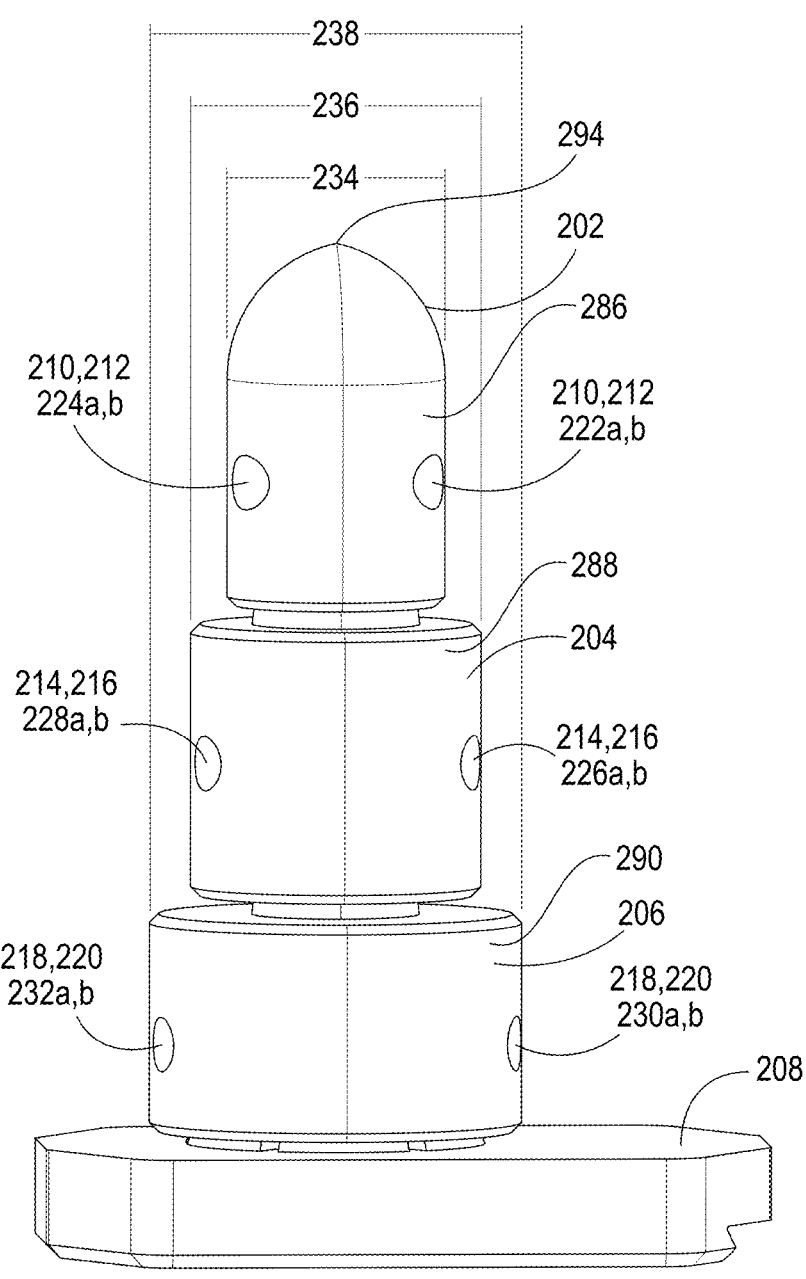
FIG. 29 is a side view of an embodiment of a surgical implant.
Figure 30:
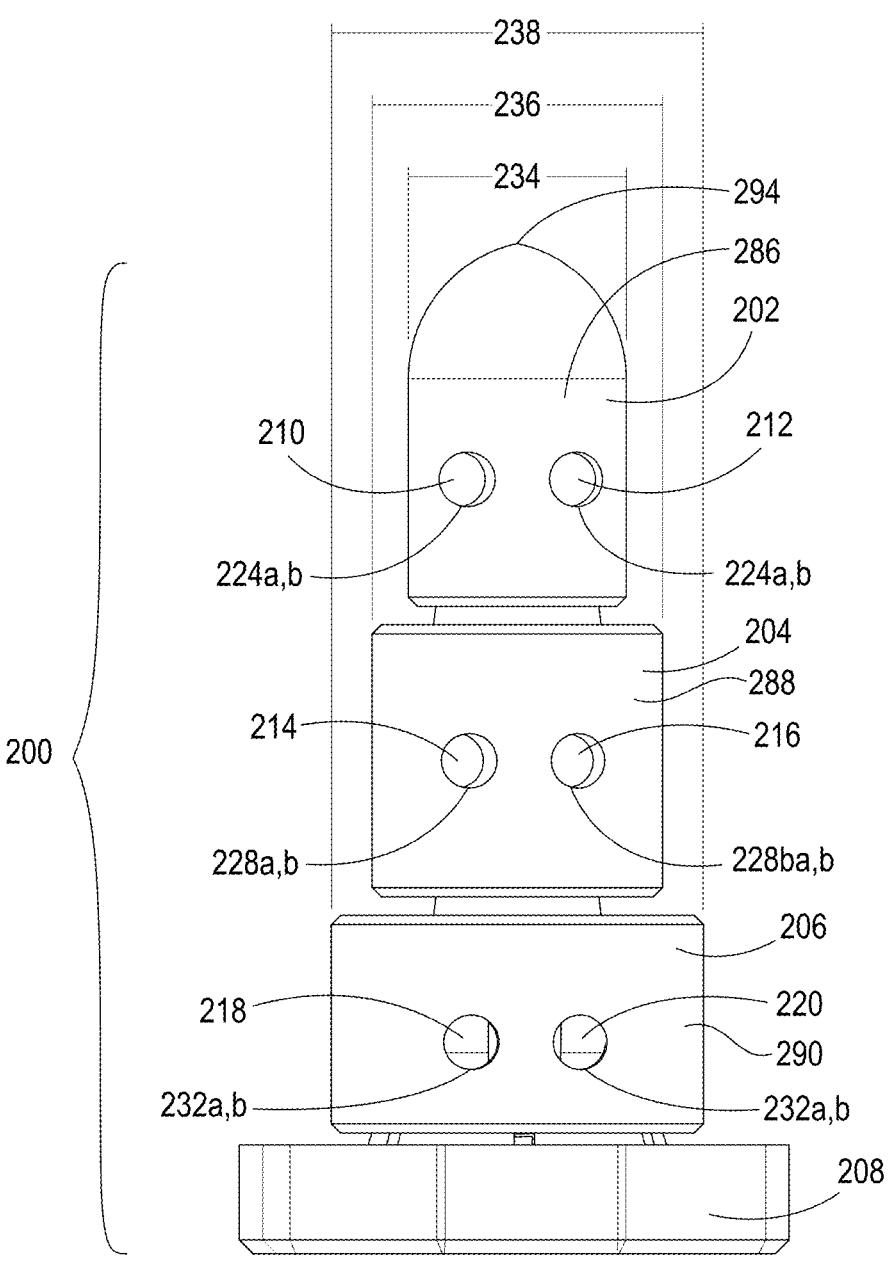
FIG. 30 is a rear view of an embodiment of a surgical implant.
Figure 31:
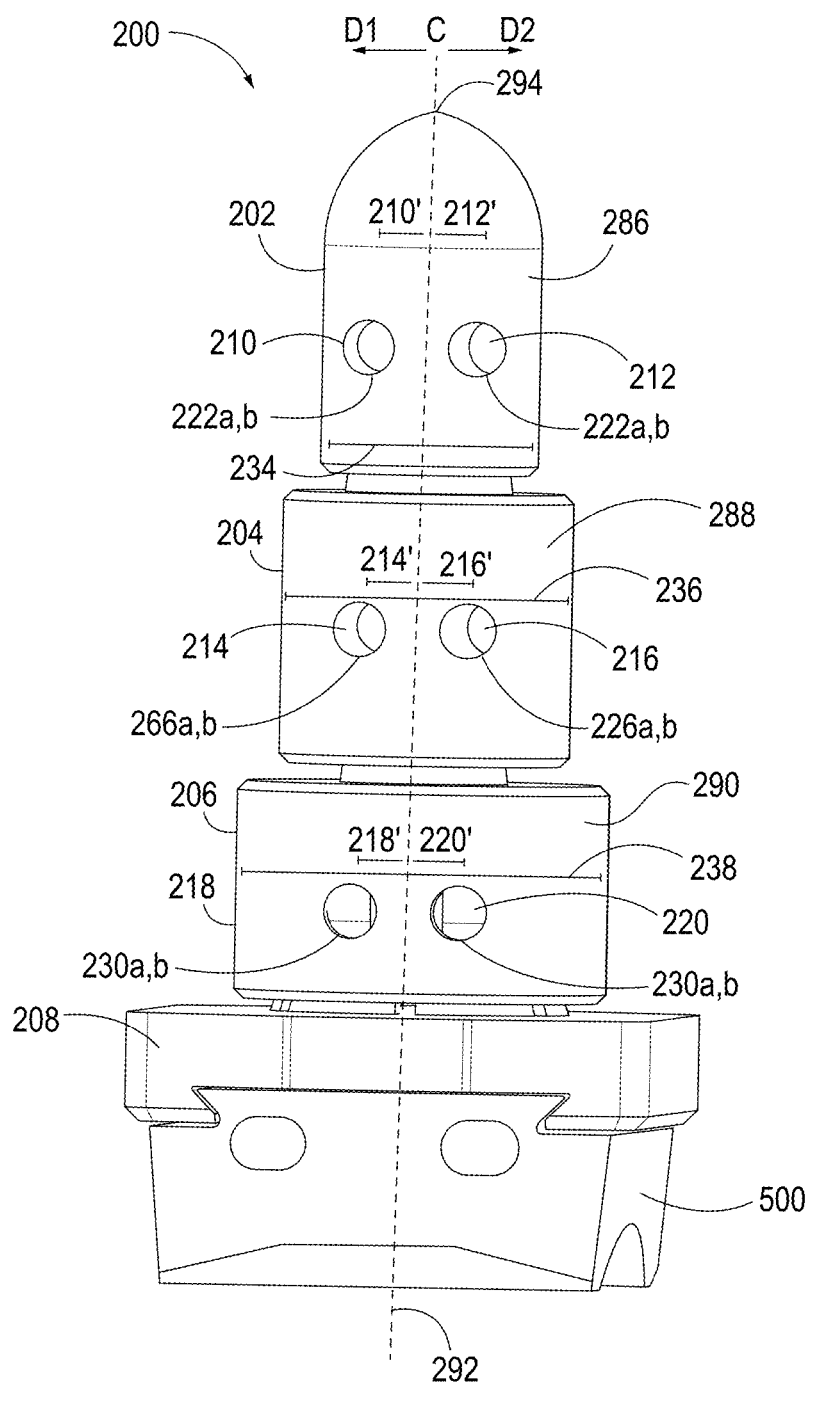
FIG. 31 is a front view of an embodiment of a surgical implant.
Figure 38:
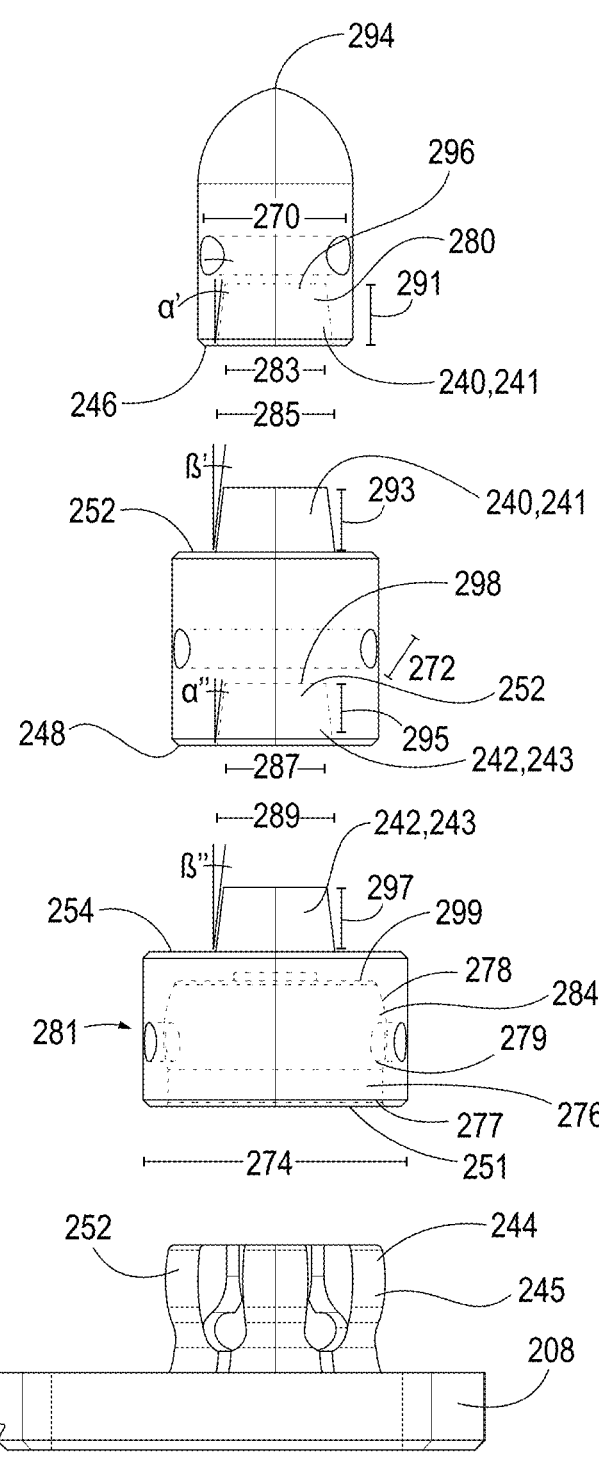
FIG. 38 is an exploded view of an embodiment of a surgical implant.

In embodiments, as shown in FIGS. 28, 35, 38, the projection 241 of the superior face 252 of the at least one intermediate stem component 204 may be configured to be received in the recess 280 of the inferior face 246 of the head stem component 202. The projection 241 and the recess 280 may form a press-fit connection. In embodiments, the projection 243 of the superior face 254 of the base stem component 206 may be configured to be received in the recess 282 of the inferior face 248 of the at least one intermediate stem component 204. The projection 243 and the recess 282 may form a press-fit connection. At least one of the recess 280 of the head stem component 202, projection 241 of the intermediate stem component 204, recess 282 of the at least one intermediate stem component 204, and projection 282 of the base stem component 206 may include a surface feature. The surface feature may be configured to maintain the press-fit connection between adjacent stem components 202, 204, 206. The surface feature may be any suitable feature, including but not limited to surface texture, locking features, adhesives, and magnets. A surface texture may have a suitable surface roughness. The surface roughness may be any suitable roughness. The surface roughness may be between 0 and 2 um Ra or 0 and 2 um Rz. The surface roughness may be between 0 and 1 um Ra or 0 and 1 um Rz. The surface roughness may be approximately 0.8 um Ra or 0.8 um Rz.

In embodiments, as shown in FIGS. 28, 35, 38, the recess 280 of the head stem component 202, projection 241 of the intermediate stem component 204, recess 282 of the at least one intermediate stem component 204, and projection 282 of the base stem component 206 may each include any suitable shape, including but not limited to a taper, a ball member, a lockout element, a multi-point lockout, and an oblong member. The recess 280 of the head stem component 202, projection 241 of the intermediate stem component 204, recess 282 of the at least one intermediate stem component 204, and projection 282 of the base stem component 206 may each include any suitable taper, including but not limited to a Morse taper, a CAT taper, an R8 taper, a national machine tool builders (NMTB) taper, and a pipe thread taper. In one embodiment, the recess 280 of the head stem component 202, projection 241 of the intermediate stem component 204, recess 282 of the at least one intermediate stem component 204, and projection 282 of the base stem component 206 comprise a Morse taper.

In embodiments, as shown in FIGS. 28, 35, 38, the dimensions of Morse taper of the recess 280 of the head stem component 202, projection 241 of the intermediate stem component 204, recess 282 of the at least one intermediate stem component 204, and projection 282 of the base stem component 206 may be substantially equivalent, and configured to form a press-fit. This may result in the configuration of the connections between the recess 280 of the head stem component 202, projection 241 of the intermediate stem component 204, recess 282 of the at least one intermediate stem component 204, and projection 282 of the base stem component 206 to be interchangeable. Accordingly, the recess 280 of the head stem component 202 and the projection 282 of the base stem component 206 may form a press-fit connection, allowing the user to choose not to use the intermediate stem component 204, and only use the head stem component 202 and the base stem component 206. The recess 282 of the at least one intermediate stem component 204 may form a press-fit connection with the projection 241 of another intermediate stem component 204, allowing a user to choose to use multiple intermediate stem components 204.

In embodiments, as shown in FIGS. 28, 35, 38, the recess 280 of the head stem component 202 may include a first recess taper angle α', projection 241 of the intermediate stem component 204 may include a first projection taper angle β', recess 282 of the at least one intermediate stem component 204 may include a second recess taper angle α", and projection 282 of the base stem component 206 may include a second projection taper angle β" The first recess taper angle α', first projection taper angle β', second recess taper angle α", and second projection taper angle β" may have a tolerance of 1°, of 0.2°, of 0.125°, and may be any suitable angle. The first recess taper angle α', first projection taper angle β', second recess taper angle α", and second projection taper angle β" may be approximately 2° to 10°, approximately 4° to 8, approximately 5° to 6°, and may be approximately 5.708°.

In embodiments, as shown in FIGS. 28, 35, 38, the recess 280 of the head stem component 202 may include a first recess height 291 and a first recess width 283. The projection 241 of the at least one intermediate stem component 204 may include a first projection height 293 and a first projection width 285. The recess 242 of the at least one intermediate stem component 204 may include a second recess height 295 and a second recess width 287. The projection 282 of the base stem component 206 may include a second projection height 297 and a second projection width 289. The first recess height 291, first projection height 293, second recess height 295, and second recess height 295 may each be any suitable height. The first recess width 283, first projection width 285, second recess width 287, and second projection width 289 may each be any suitable width.

In embodiments, as shown in FIGS. 28, 35, 38, the first recess height 291, first projection height 293, second recess height 295, and second recess height 295 may be substantially equal, and configured to form a press-fit. The first recess width 283, first projection width 285, second recess width 287, and second projection width 289 may be substantially equal, and configured to form a press-fit.

In embodiments, as shown in FIGS. 28, 35, 38, the first recess height 291, first projection height 293, second recess height 295, and second recess height 295 may have a tolerance of 0.125 mm, or 0.125 mm.

In embodiments, as shown in FIGS. 28, 35, 38, the projection 241 of the superior face 252 of the at least one intermediate stem component 204 may include any suitable cross-section, including but not limited to a substantially frustoconical cross-section, a substantially circular cross-section, a substantially rectangular cross-section, and a substantially trapezoidal cross-section. In embodiments, the recess 280 of the inferior face 246 of the head stem component 202 may include any corresponding cross-section, including but not limited to a substantially frustoconical cross-section, a substantially circular cross-section, a substantially rectangular cross-section, and a substantially trapezoidal cross-section.

In embodiments, as shown in FIGS. 28, 35, 38, the projection 241 of the superior face 252 of the at least one intermediate stem component 204 may include a projection cross-sectional dimension. The projection 243 of the superior face 254 of the base stem component 206 may include a corresponding projection cross-sectional dimension. In embodiments, the projection cross-sectional dimension of the projection 241 and the projection cross-sectional dimension of the projection 243 may be substantially conformal, and configured to form a press-fit connection.

In embodiments, as shown in FIGS. 28, 35, 38, the recess 280 of the inferior face 246 of the head stem component 202 may have a recess cross-sectional dimension. In embodiments, the recess 282 of the inferior face 248 of the at least one intermediate stem component 204 may have a recess cross-sectional dimension. In embodiments, the dimensions of recess cross-sectional dimension of the recess 280 and the recess cross-sectional dimension of the recess 282 may be substantially equivalent.

In embodiments, as shown in FIGS. 28, 35, 38, the dimensions of projection cross-sectional dimension of the projection 241 and the recess cross-sectional dimension of the recess 280 may be substantially equivalent. The dimensions of projection cross-sectional dimension of the projection 243 and the recess cross-sectional dimension of the recess 282 may be substantially equivalent. The dimensions of projection cross-sectional dimension of the projection 241, the recess cross-sectional dimension of the recess 280, the projection cross-sectional dimension of the projection 243, and the recess cross-sectional dimension of the recess 282 may be substantially equivalent and configured to form a press-fit connection.

In embodiments, as shown in FIGS. 28, the head stem component 202 may include a first cross-sectional dimension 234, the at least one intermediate stem component 204 may include a second cross-sectional dimension 236, and the base stem component 206 may include a third cross-sectional dimension 238. The first cross-sectional dimension 234 may be less than or equal to the second cross-sectional dimension 236. The second cross-sectional dimension 236 may be less than or equal to the third cross-sectional dimension 238.

As shown in FIGS. 28-31, in embodiments, the implant 200 may be disposed along a longitudinal axis. The head stem component 202, at least one intermediate stem component 204, and base stem component 206 may each include sidewalls 286, 288, 290. The head stem component 202 may include at least one bore 210, 212 through the sidewalls 286. The at least one intermediate stem component 204 may include at least one bore 214, 216 through the sidewalls 288. The base stem component 206 may include at least one bore 218, 220 through the sidewalls 290. The head stem component 202 may include two bores 210, 212. The at least one intermediate stem component 204 may include two bores 214, 216. The base stem component 206 may include two bores 218, 220. The bores 210, 212, 214, 216, 218, 220 may be oriented substantially perpendicularly to the longitudinal axis of the implant 200.

In embodiments, as shown in FIGS. 28-31, corresponding pairs of bores 210 and 212, 214 and 216, 218 and 220, are substantially parallel to each other, and oriented on a plane substantially perpendicular to the longitudinal axis of the implant 200. In other embodiments, the pairs of bores are located the same distance from the longitudinal axis of the implant 200. In still further embodiments, the pairs of bores have substantially equivalent dimensions to each other, and the other bore pairs.

Embodiments of the present disclosure include a method of implanting a surgical implant 200. The method may include drilling an intramedullary canal in a patient's tibia. Drilling the intramedullary canal may be performed by a nested reamer 12, as discussed above. The method may include inserting a head stem component 202 into the intramedullary canal. The method may include inserting at least one intermediate stem component 204 into the intramedullary canal. The method may include engaging a recess 280 of the head stem component 202 with an engagement feature 240, including a projection 241, of the at least one intermediate stem component 204, before or after insertion of the head stem component 202 into the intramedullary canal, or surgical site O. The method may include forming a press-fit connection between the projection 241 and the recess 280. The method may include inserting a base stem component 206 into the intramedullary canal. The method may include engaging the recess 282 of the intermediate stem component 204 with the projection 243 of the base stem component 206, before or after insertion of the intermediate stem component 204 into the intramedullary canal, or surgical site O. The method may include forming a press-fit connection between the projection 282 and the recess 242.

In embodiments, as shown in FIGS. 28-31, the implant 200 may include a proximal end 292 and a distal end 294 disposed distally to the proximal end 292 with respect to the longitudinal axis. The implant 200 comprises a plurality of stem components 202, 204, 206. The plurality of stem components may include a head stem component 202, at least one intermediate stem component 204, and a base stem component 206. The head stem component 202 may be disposed at the distal end 294 of the implant 200. The head stem component 202 may include an inferior face 246 disposed on a proximal end of the head stem component 202. The head stem component 202 may include a first recess 280 extending distally from the inferior face 246 and extending to a distal recess face 296. The head stem component 202 may include two head stem bores 210, 212 disposed distally with respect to the distal recess face 296. The at least one intermediate stem component 204 may be disposed proximally with respect to the head stem component 202. The at least one intermediate stem component 204 may include an inferior face 248 disposed on a proximal end of the at least one intermediate stem component 204. The at least one intermediate stem component 204 may include a second recess 282 on the inferior face 248 of the at least one intermediate stem component 204 and extending distally from the inferior face 248 to a distal recess face 298. The at least one intermediate stem component 204 may include two intermediate stem bores 214, 216 disposed distally with respect to the distal recess face 298 of the second recess 282.

In embodiments, as shown in FIGS. 28-31, the base stem component 206 may be disposed proximally with respect to the at least one intermediate stem component 204. The base stem component 206 may include an inferior face 250 disposed on a proximal end of the base stem component 206. The base stem component 206 may include a third recess 284 disposed on the inferior face 250 of the base stem component 206 and extending distally to a distal recess face 299. The base stem component 206 may include two base stem bores 218, 220 intersecting with the third recess 284 proximally to the distal recess face 299 of the third recess 284.

In embodiments, as shown in FIGS. 28-31, the implant 200 may include a vertical axis C. The two head stem bores 210, 212 may include a first bore 210 and a second bore 212. The two intermediate stem bores 214, 216 may include a third bore 214 and a fourth bore 216. The two base stem bores 218, 220 may include a fifth bore 218 and a sixth bore 220. The first bore 210 may be laterally offset from the vertical axis C in a first direction D1 to a lateral offset distance 210'. The second bore 212 may be laterally offset from the vertical axis C in a second direction D2 to a lateral offset distance 212'. The third bore 214 may be laterally offset from the vertical axis C in the first direction D1 to a lateral offset distance 214'. The fourth bore 216 may be laterally offset from the vertical centerline in the second direction D2 to a lateral offset distance 216'. The fifth bore 218 may be laterally offset from the vertical axis C in the first direction D1 to a lateral offset distance 218'. The sixth bore 220 may be laterally offset from the vertical centerline in the second direction D2 to a lateral offset distance 220'. In embodiments, the first direction D1 may be opposite to the second direction D2.

In embodiments, as shown in FIGS. 28-31, the first bore 210 may include an anterior opening 222a and a posterior opening 224a. The second bore 212 may include an anterior opening 222b and a posterior opening 224b. The third bore 214 may include an anterior opening 226a and a posterior opening 228a. The fourth bore 216 may include an anterior opening 226b and a posterior opening 228b. The fifth bore 218 may include an anterior opening 230a and a posterior opening 232a. The sixth bore 220 may include an anterior opening 230b and a posterior opening 232b. In embodiments, determination of respective anterior and posterior openings depends only on which way a respective stem component is facing relative to the patient.

In embodiments, as shown in FIGS. 28-31, the first bore 210 and second bore 212 of the head stem component 202 may be substantially coplanar, the third bore 214 and fourth bore 216 of the at least intermediate stem component 204 may be substantially coplanar, and the fifth bore 218 and sixth bore 220 of the base stem component 206 may be substantially coplanar.

In embodiments, as shown in FIGS. 28-31, the head stem component 202 may any suitable cross-sectional shape, including but not limited to a substantially circular cross-sectional shape, a substantially rectangular cross-sectional shape, and a substantially irregular cross-sectional shape. The head stem component 202 may include a first substantially circular cross-sectional shape with a head stem circumference 234. The at least one intermediate stem component 204 may any suitable cross-sectional shape, including but not limited to a substantially circular cross-sectional shape, a substantially rectangular cross-sectional shape, and a substantially irregular cross-sectional shape. The at least one intermediate stem component 204 may include a second substantially circular cross-sectional shape with an intermediate stem circumference 236. The base stem component 206 may any suitable cross-sectional shape, including but not limited to a substantially circular cross-sectional shape, a substantially rectangular cross-sectional shape, and a substantially irregular cross-sectional shape. The base stem component 206 may include a third substantially circular cross-sectional shape with a base stem circumference 238. The head stem circumference 234 may be substantially equal to or less than the first reamer circumference 132. The intermediate stem circumference 236 may be substantially equal to or less than the second reamer circumference 136. The base stem circumference 238 may be substantially equal to or less than the third reamer circumference 138.

In embodiments, at least one of the plurality of stem components 202, 204, 206 may include a traverse opening (not shown). The traverse opening may be configured to receive any suitable fixation element, including but not limited to a traverse fixation screw, a pin, or a rod. In embodiments, the fixation element is secured through the tibia, through one of the respective stem component 202, 204, 206 via the traverse opening, and into the opposite side of the tibia. The traverse opening may be oriented such that the fixation element is inserted in the anterior to posterior or posterior to anterior direction. The traverse opening may be coplanar with the at least one bore 210, 212, 214, 216, 218, 220 of the corresponding stem components 202, 204, 206. The traverse opening may be disposed superior to the at least one bore 210, 212, 214, 216, 218, 220 of the corresponding stem components 202, 204, 206. The traverse opening may be oriented substantially parallel to the at least one bore 210, 212, 214, 216, 218, 220 of the corresponding stem components 202, 204, 206. The traverse opening may be oriented substantially perpendicular to the at least one bore 210, 212, 214, 216, 218, 220 of the corresponding stem components 202, 204, 206. In one embodiment, the traverse opening may be disposed in the head stem component 202. The traverse opening may be disposed superior to the at least one bore 210, 212 of the head stem component 202.

IV. Implant Tray

In embodiments, as shown in FIGS. 28-31, 35-36 the implant 200 may include an expandable surgical device 202, 204, 206 oriented along a longitudinal axis and including a base stem component 206. The base stem component 206 may include a body 206 with any suitable cross-section, including but not limited to a substantially circular cross-section, a substantially rectangular cross-section, a substantially circular cross-section, and a substantially trapezoidal cross-section. The base stem component 206 may include an inferior face 250 with a circumferential opening 251. The base stem component may include a recess 284. The recess 284 may extend distally from the circumferential opening 251 to a distal wall 299 of the recess 284. The recess 284 may include a neck portion 276 extending distally from the circumferential opening 251 and comprising a proximal end 277 disposed at the circumferential opening 251 and a distal end 279. The recess 284 may include a substantially spherical segment 278 extending distally from the distal end 279 of the neck 276 to the distal wall 299. The substantially spherical segment 278 may form a cross-sectional dimension of increasing diameter beginning at the distal end 279 of the neck portion 276 and reaching a maximum recess diameter 281 at an equator and transitioning at the equator to a cross-sectional dimension of decreasing diameter, terminating at the distal wall 299 of the recess 284.

Referring now to FIGS. 30-31, 33, 34-36, 38, in embodiments, the surgical implant 200 may include a tray 208. The tray 208 may be disposed inferior to the expandable surgical device 202, 204, 206. The tray 208 may be selected from a plurality of tray sizes. The tray 208 may be selected from approximately five to seven sizes. The size of the tray 208 may be selected, in part, based on the resection length, discussed above. The tray 208 may include a ball member 245. The ball member 245 may include a plurality of petals 252a-f. The plurality of petals 252a-f may include at least two petals, at least three petals, at least four petals, at least five, and at least six petals. The plurality of petals 252a-f may be centered around a central axis C. The plurality of petals 252a-f may include a rounded outer wall 245, that when combined with the rounded outer wall of all petals 252a-f form a substantially spherical segment 245. The substantially spherical segment 245 of the ball member 245 may substantially match a contour of the substantially spherical segment 278 of the recess 284. The plurality of petals 252a-f may include a radially retracted position (not shown) and a radially extended position. In the radially extended position, each of the plurality of petals 252a-f may be disposed further from the central axis C than when in the radially retracted position. When in the radially retracted position, the ball member 245 may be configured to be received in the neck portion 276 of the recess 284. When in the radially retracted position, the position of the tray 208 may be adjustable relative to the base stem component 206. The tray 208 may be adjustable in any suitable manner, including but not limited to axially, polyaxially, rotatably, laterally, and longitudinally. The tray 208 may be configured to be locked in a position relative to the base stem component 206 when the plurality of petals 252a-f are in the radially extended position. When in the radially extended position, the plurality of petals 252a-f cannot pass through the neck portion 276, thereby retaining the ball member 245 inside the recess 284.

In alternative embodiments, the tray 208 may be configured to connect to the base stem component 208 in any suitable manner (not shown). The tray 208 may include a recess (not shown) whereas the base stem component 208 may include a ball portion (not shown). The tray 208 and base stem component 208 may include any suitable engagement element, including but not limited to a protrusion, a lockout element, and a contoured surface. The tray 208 may include a third engagement feature 244 disposed on a superior face 254 of the tray 208. The base stem component 206 may include a third recess 284.

Figure 36:
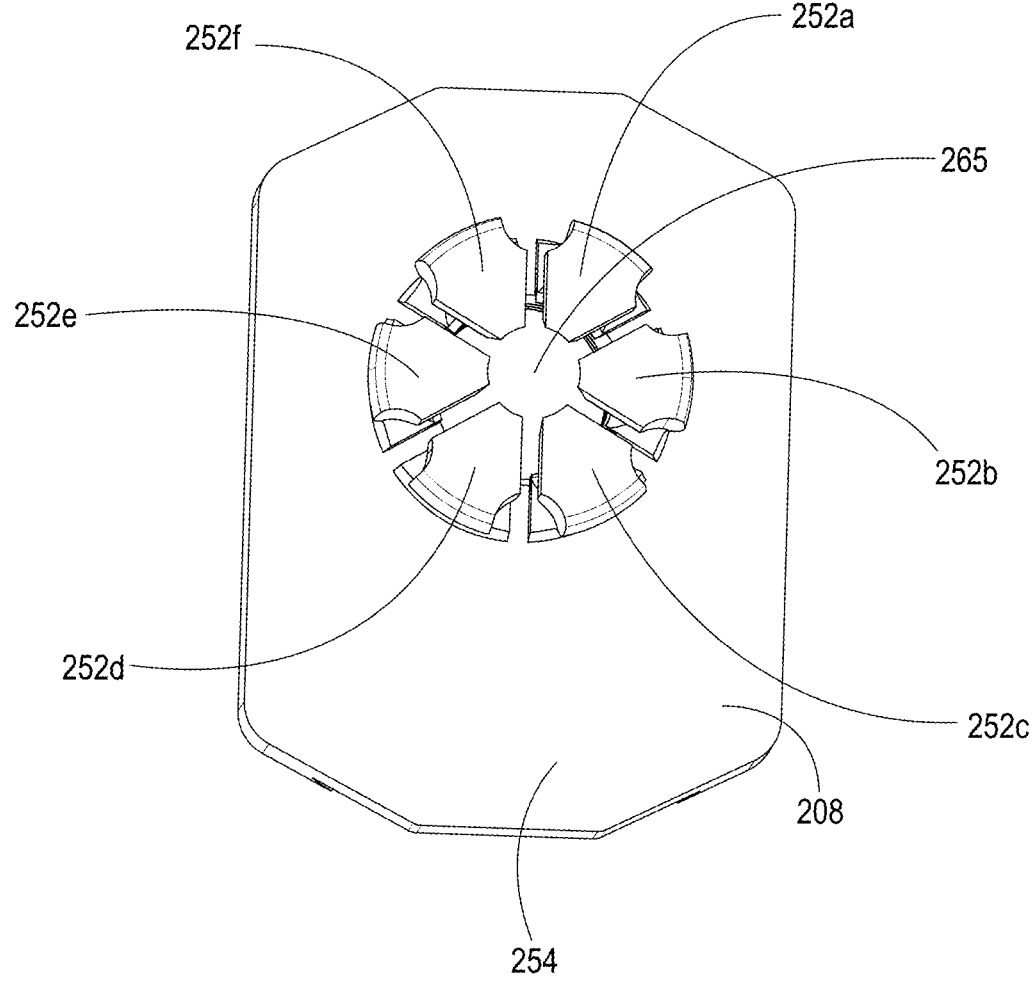
FIG. 36 is a top view of an embodiment of a tibial tray.
Figures 37A, 37B:
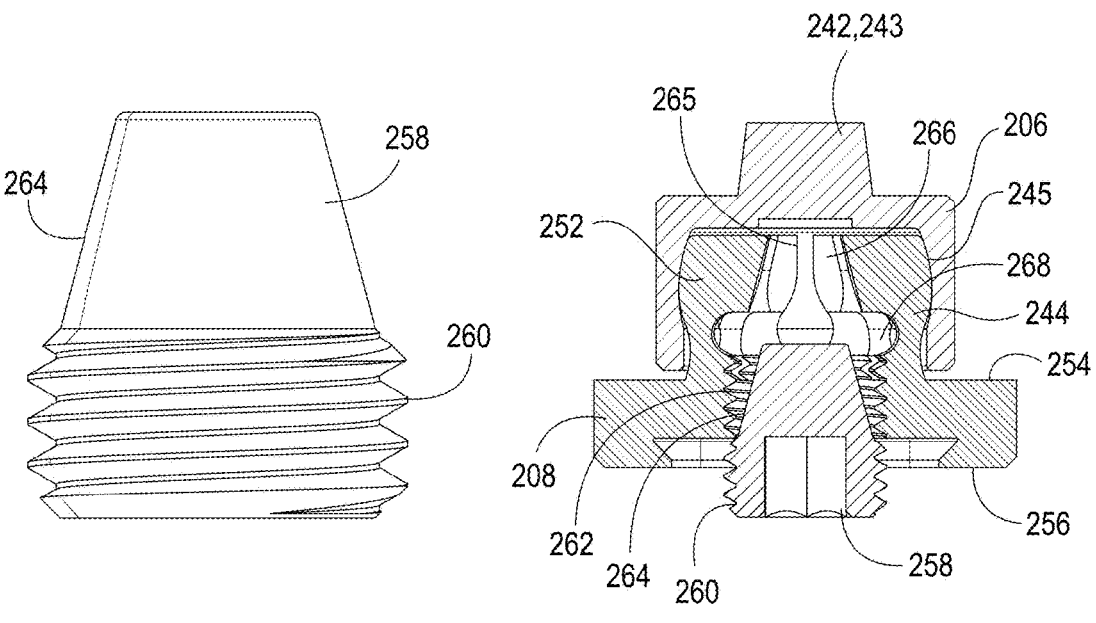
FIG. 37A is a side view of an embodiment of a nut.
FIG. 37B is a cross-sectional side view of an embodiment of a surgical stem component and tibial tray.
Figures 37C, 37D:
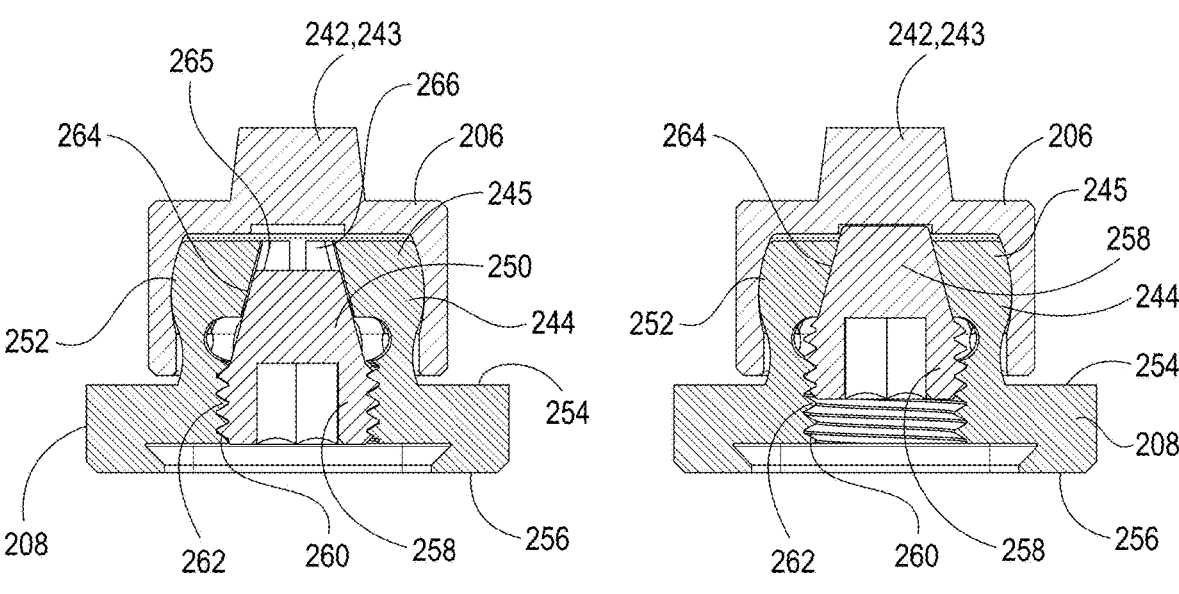
FIG. 37C is a cross-sectional side view of an embodiment of a surgical stem component and tibial tray.
FIG. 37D is a cross-sectional side view of an embodiment of a surgical stem component and tibial tray.

In embodiments, with reference to FIGS. 35-37, the tray 208 may include an opening 265 disposed between petals 252a-f. The opening 265 may include a vertically oriented opening 265 centered around the central axis C. In alternative embodiments, the opening 265 may include a traverse opening. The surgical implant 200 may include a nut 258 configured to be received within the vertically oriented opening 265 of the tray 208. The surgical implant 200 may include a nut 258 configured to be received within the vertically oriented opening 265 of the tray. The surgical implant 200 may include a nut 258 configured to be received within the traverse opening 265 of the tray. The nut 258 may be any suitable element, including but not limited to a nut, a screw, and a press-fit element. The nut 258 may be configured to be at least partially surrounded by the plurality of petals 252a-f.

In embodiments, with reference to FIG. 37, the nut 258 may include any suitably shaped portion, including but not limited to a substantially frustoconical portion 264, a substantially circular portion, a substantially rectangular portion, and a substantially trapezoidal portion.

In embodiments, with reference to FIGS. 35-37, the plurality of petals 252a-f may include a wall 266, including any suitably shaped wall, including but not limited to a substantially frustoconical wall 266, a substantially circular wall, a substantially rectangular wall, and a substantially trapezoidal wall, disposed opposite to the rounded outer wall 245. In one embodiment, the frustoconical portion 264 and the wall 266 have a corresponding frustoconical shape. The substantially frustoconical wall 266 of the plurality of petals 252a-f may be configured to engage the substantially frustoconical portion 264 of the nut 258.

In embodiments, as shown in FIG. 37, at least a portion of the vertically oriented opening 265 may include an internal thread 262. The internal thread 262 may include any suitable thread. In embodiments, at least a portion of the nut 258 may include an external thread 260. The external thread 260 of the nut 258 may be configured to engage the internal thread 262 of the vertically oriented opening 265, such that the nut 258 can be advanced vertically via rotation of the nut. The external thread 260 may include any suitable thread. In embodiments, the nut 258 may be configured to move distally. The nut 258 may be configured to apply a radially outward force on the plurality of petals 252a-f by engagement of the frustoconical portion 264 of the nut 258 with the frustoconical wall 266 of the plurality of petals 252a-f when the nut 258 is advanced distally.

In embodiments, with reference to FIG. 37, the nut 258 may be configured to be rotated by any suitable device, including but not limited to a wrench, a screwdriver, and a power driver. The nut 258 may be configured to be rotated and advanced upward by e.g. a wrench.

Figure 41:
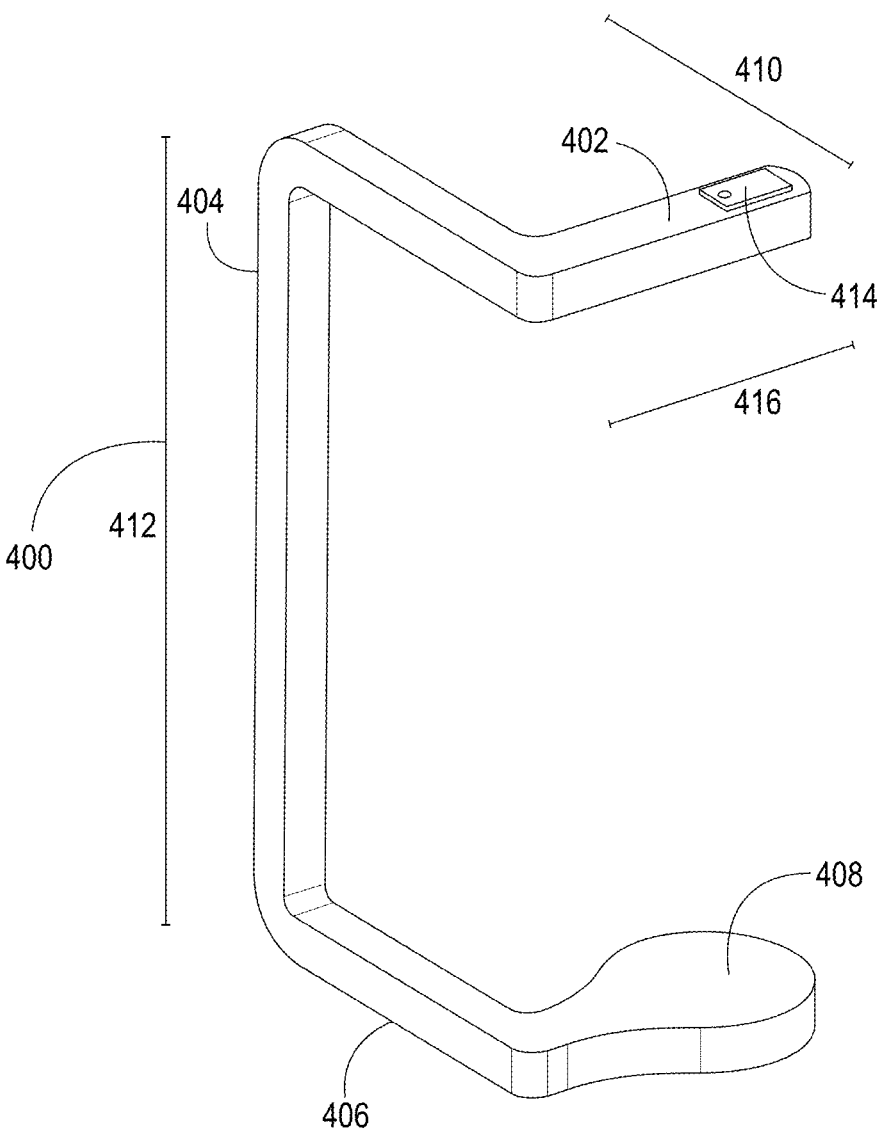
FIG. 41 is a perspective view of an embodiment of a tibial tray tap.
Figure 42:
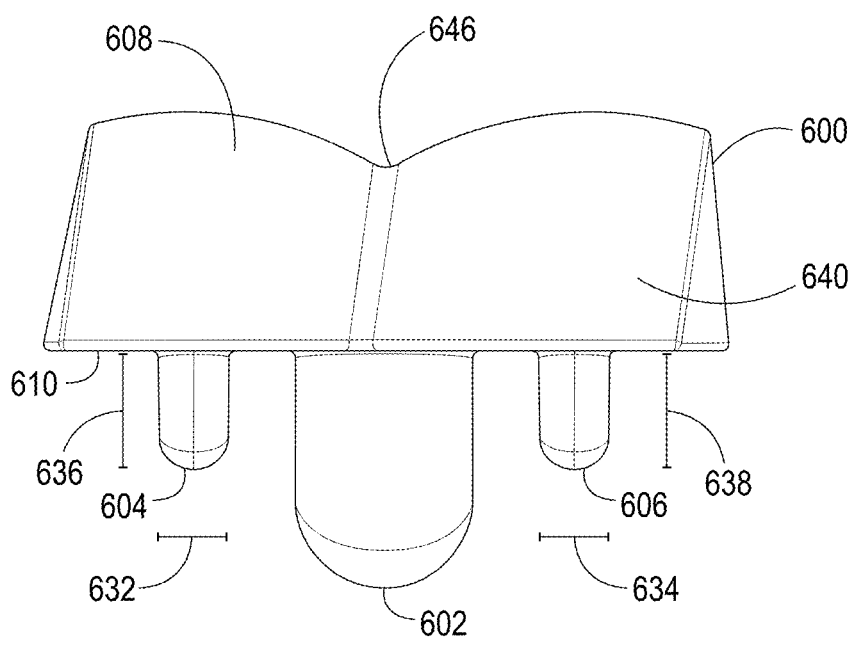
FIG. 42 is a front or rear view of an embodiment of a talar implant.
Figure 43:
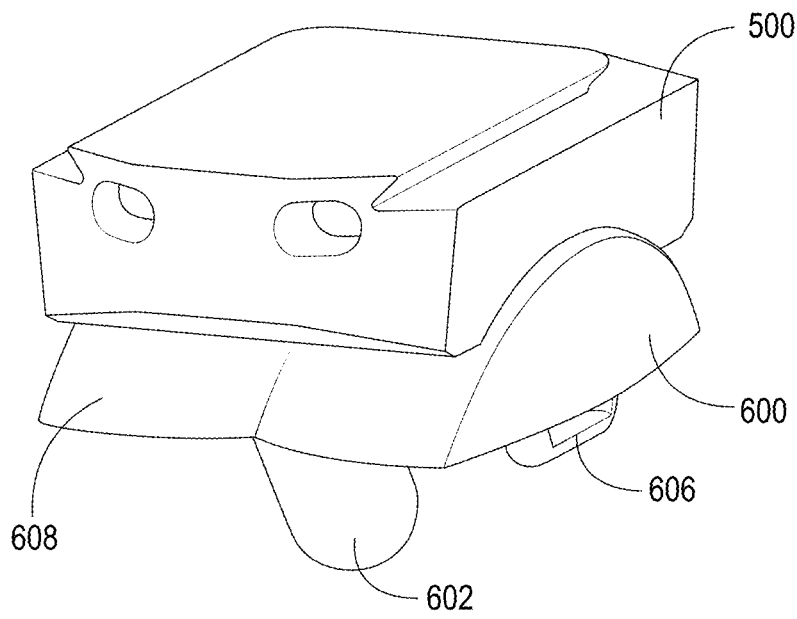
FIG. 43 is a perspective view of an embodiment of a talar implant.

Referring to FIG. 41, in embodiments, the tibial tray tap 400 may include any suitable shape. The tibial tray tap 400 may include a superior arm 402, an intermediate arm 404, an inferior arm 406, and a strike plate 408. The superior arm 402 may include an engagement element 414. The engagement element 414 may be configured to engage the tray 208. The intermediate arm 404 may be laterally offset from and substantially parallel to the longitudinal axis C. The intermediate arm 404 may include a grip element. The tibial tray tap 400 may be configured to engage the tray 208 when the implant 200 is disposed in the intramedullary canal. The tibial tray tap 400 may be configured such that the superior arm 402 contacts the tray 208. Force may be applied to the inferior arm 406, using any suitable device, including but not limited to manually applying force, a hammer, and a mallet to the strike plate 408.

In embodiments, the disclosure may include a method of inserting a surgical implant 200. The method may include providing a surgical implant 200. The implant 200 may include a base stem component 206. The method may include providing a tray 208. The tray may include a ball member 245. The ball member 245 may include a plurality of petals 252a-f. The method may include inserting the base stem component 206 into an intramedullary canal of a patient's tibia. The method may include inserting the ball member 245 into the recess 284 of the base stem component 206. The ball member 245 may be configured to be received in the neck portion 276 of the recess 284 when the plurality of petals 252a-f may be in the radially retracted position. The position of the tray 208 may be rotatably adjusted relative to the base stem component 206 when the plurality of petals 252a-f may be not in a radially extended position. The tray 208 may be locked in position in relation to the base stem component 206 when the plurality of petals 252a-f may be in the radially extended position. In embodiments, the method may include providing a nut 258. The method may include engaging the nut 258 in the vertically oriented opening 265 of the tray 208. The method may include advancing the nut distally through the vertically oriented opening 265 of the tray 208 into an opening 266 disposed within the plurality of petals 252a-f. The method may include expanding the plurality of petals 252a-f radially outward to engage an inner sidewall 278 of the recess 284. In embodiments, advancing the nut 258 distally through the vertically oriented opening 265 of the tray 208 may include providing e.g. a wrench. In embodiments, advancing the nut 258 distally through the vertically oriented opening 265 of the tray 208 may include applying upward force to a tap portion 408 of the lower arm 406 of the tibial tray tap 400.

The method may include applying upward force to the inferior arm 404 of the tibial tray tap 400. In one embodiment, applying upward force includes striking the strike face 408 with hammer or mallet, or other such tool.

In embodiments, the tray 208 may be configured to engage a first artificial joint surface 500. The first artificial joint surface may include any suitable artificial joint surface, including but not limited to an artificial tibial joint surface and an artificial talar joint surface.

V. Implant Stem Placement Tool

Figure 39:
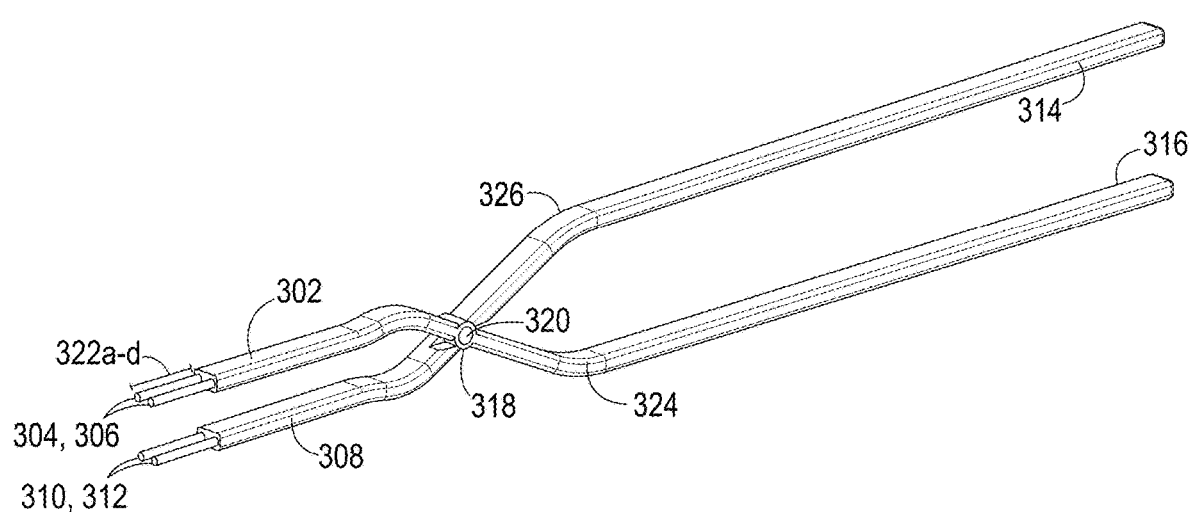
FIG. 39 is a perspective view of an embodiment of a placement tool.
Figure 40:
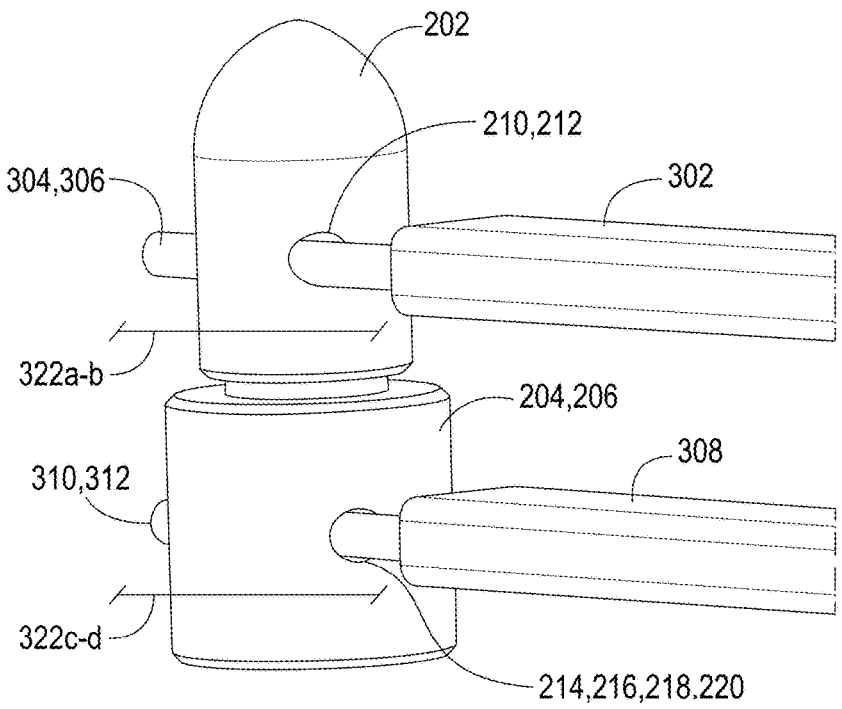
FIG. 40 is a perspective view of an embodiment of a placement tool and a surgical implant.

In embodiments, as shown in FIGS. 39-40, the surgical system 10 may include a placement tool 300. In general, the placement tool 300 may assist in creating a press-fit between adjacent stem components by applying a force to such elements. In embodiments, such force may be applied by inserting engagement elements 304, 306, 310, 312 into adjacent bores of adjacent stem components and squeezing them together via grips 314, 316.

In embodiments, as shown in FIGS. 39-40, the placement tool 300 may include a first prong 302. The placement tool 300 may include a second prong 308. The placement tool 300 may include a first arm 324. The placement tool 300 may include a second arm 314. The first arm 316 and the second arm 314 may include a first grip 314, and a second grip 316. The first arm 326 and the second arm 314 may be configured to intersect at a pivot point 318. The first prong 302 and the second prong 308 may be configured to engage with at least two of the at least one bore 210, 212, 214, 216, 218, 220 of the head stem component 202, at least one intermediate stem component 204, and base stem component 206. The first prong 302 and second prong 308 may be configured to engage with bores 210, 212, 214, 216, 218, 220 of adjacent stem components, e.g., the first prong 302 may be configured to engage the at least one bore 210, 212 of the head stem component 202 while the second prong 308 may be configured to engage the at least one bore 214, 216 of the at least one intermediate stem component 204.

In embodiments, as shown in FIGS. 39-40, the first prong 302 may include a first engagement element 304 and a second engagement element 306. The second prong 308 may include a third engagement element 310 and a fourth engagement element 312. The first engagement element 304 and third engagement element 308 may be configured to be inserted into the at least one bore 210, 212, 214, 216, 218, 220 of adjacent stem components 202, 204, 206. The second engagement element 306 and fourth engagement element 312 may be configured to be inserted into the at least one adjacent bore 210, 212, 214, 216, 218, 220 of adjacent stem components 202, 204, 206. When the first engagement element 304 may be configured to be inserted into one of the at least one bore 210, 212 of the head stem component 202, the third engagement element 310 may be configured to be inserted into one of the at least one bore 214, 216 of the at least one intermediate stem component 204. When the second engagement element 306 may be configured to be inserted into one of the at least one bore 210, 212 of the head stem component 202, the fourth engagement element 310 may be configured to be inserted into one of the at least one bore 214, 216 of the at least one intermediate stem component 204.

In embodiments, as shown in FIGS. 39-40, when the first engagement element 304 is inserted into one of the at least one bore 214, 216 of the at least one intermediate stem component 204, the third engagement element 310 may be configured to be inserted into one of the at least one bore 218, 220 of the head stem component 206. When the second engagement element 306 may be configured to be inserted into one of the at least one bore 214, 216 of the at least one intermediate stem component 204, the fourth engagement element 310 may be configured to be inserted into one of the at least one bore 218, 220 of the base stem component 206.

In embodiments, as shown in FIG. 39, the first arm 324 may include the first prong 302 and a first grip section 316. The second arm 326 may include the second prong 308 and a second grip section 314. In embodiments, as shown in FIG. 39, the placement tool 300 may include a pivot component 320 at the pivot point 318.

In embodiments, as shown in FIGS. 39-40, the first prong 302 may include a first engagement element 304 and a second engagement element 306. The second prong 308 may include a third engagement element 310 and a second engagement element 312. The first engagement element 304 may be configured to be inserted into one of the anterior opening 222a, 226a, 240a or posterior opening 224a, 228a, 232a of the first bore 210, third bore 214, and fifth bore 218. When the first engagement element 304 is inserted into the anterior opening 222a, 226a, 240a of one of the first bore 210, third bore 214, and fifth bore 218, the second engagement element 306 is configured to be inserted into an adjacent opening 222b, 226b, 240b. When the first engagement element 304 is inserted into the posterior opening 224a, 228a, 232a of one of the first bore 210, third bore 214, and fifth bore 218, the second engagement element 306 is configured to be inserted into an adjacent opening 224b, 228b, 232b. When the third engagement element 310 is inserted into the anterior opening 222a, 226a, 240a or posterior opening 224a, 228a, 232a of the first bore 210, third bore 214, and fifth bore 218, the fourth engagement element is configured to be inserted into an adjacent opening 222b, 226b, 240b. When the third engagement element 310 is inserted into the posterior opening 224a, 228a, 232a of one of the first bore 210, third bore 214, and fifth bore 218, the fourth engagement element is configured to be inserted into an adjacent opening 224b, 228b, 232b.

In embodiments, as shown in FIGS. 39-40, the first engagement element 304, second engagement element 306, third engagement element 310, and fourth engagement element 312 may include a first insertion length 322a, second insertion length 322b, third insertion length 322c, and fourth insertion length 322d, respectively. The first bore 210, second bore 212, third bore 214, fourth bore 216, fifth bore 218, and sixth bore 220 may include a first bore length 270, second bore length 270, third bore length 272, fourth bore length 272, fifth bore length 274, and sixth bore length 274, respectively. In embodiments, the respective insertion lengths 322a-d are substantially equivalent, and greater than the bore lengths 270, 272, 274.

Embodiments of the present disclosure include a method of implanting a surgical implant 200 into an intramedullary canal of a tibia. The surgical implant 200 may be inserted into the intramedullary canal before or after the plurality of stem components 202, 204, 206 are affixed to one another. The method may include the use of all stem components 202, 204, 206, or the user may choose to only use certain components, for example head stem component 202 and base stem component 206. The method may include providing the implant 200 and providing the placement tool 300. The method may include inserting the first engagement element 304 into the first bore 210 and the second engagement element 306 into the second bore 212. The method may include inserting the third engagement element 310 into the third bore 214 and the fourth engagement element 312 into the fourth bore 216. The method may include inserting a first engagement feature 240 of the at least one intermediate stem component 204 into a first recess 280 of the head stem component. The method may include squeezing the placement tool 300 to apply pressure to the head stem component 202 and the at least one intermediate stem component 204 to engage the first engagement feature 240 and the first recess 280, thereby forming a press-fit connection. The method may include inserting the at least one intermediate stem component 204 into the intramedullary canal using the placement tool 300 before or after forming a press-fit connection between the head stem component 202 and the at least one intermediate stem component 204. The method may include removing the first engagement element 304, second engagement element 306, third engagement element 310, and fourth engagement element 312 from the first bore 310, second bore 312, third bore 314, and fourth bore 316, respectively.

In embodiments, the method may include inserting a second engagement feature 242 of the base stem component 206 into a second recess 282 of the at least one intermediate stem component 204. In embodiments, the method may include squeezing the placement tool 300 to apply pressure to the at least one intermediate stem component 204 and the base stem component 206 to engage the second engagement feature 242 and second recess 282. In embodiments, the method may include providing a tray 208. The method may include inserting the third engagement feature 244 into the third recess 284.

In embodiments, the method may include inserting the first engagement element 304 into the third bore 214 and the second engagement element 306 into the fourth bore 216. The method may include inserting the third engagement element 310 into the fifth bore 218 and the fourth engagement element 312 into the sixth bore 220. The method may include inserting the second engagement feature 242 into the second recess 282. The method may include squeezing the gripping mechanism 314, 316 to apply pressure to the at least one intermediate stem component 204 and the base stem component 206 to engage the second engagement feature 242 and the second recess 282, thereby forming a press-fit connection. The method may include inserting the base stem component 206 into the intramedullary canal using the placement tool 300. The method may include removing the first engagement element 304, second engagement element 306, third engagement element 310, and fourth engagement element 312 from the third bore 214, fourth bore 216, fifth bore 218, and sixth bore 220, respectively.

VI. Talar Implant

In embodiments, as shown in FIGS. 42-45, the present disclosure may include a talar implant 600 configured to be implanted on a resected surface of a talus. The talar implant 600 may include a body 640. The body 640 may include an inferior face 610. The talar implant 600 may include at least one keel 604. The at least one keel 604 may include a first keel 604. The at least one keel 604 may be disposed on the inferior face 610 of the body 640. The at least one keel 604 may include a first keel length 612, a first keel depth 636, and a first keel width 632. The first keel length 612 may be greater than the first keel depth 636 and the first keel width 632. The at least one keel 604 may be disposed on an anterior side, posterior side, or lateral side of the inferior face 610.

In embodiments, as shown in FIGS. 42-45, the talar implant 600 may include a second keel 606. The second keel may include a second keel length 614, a second keel depth 638, and a second keel width 634. In embodiments, the second keel length 614 may be greater than the second keel depth 638 and the first keel width 634.

Figures 44, 45:
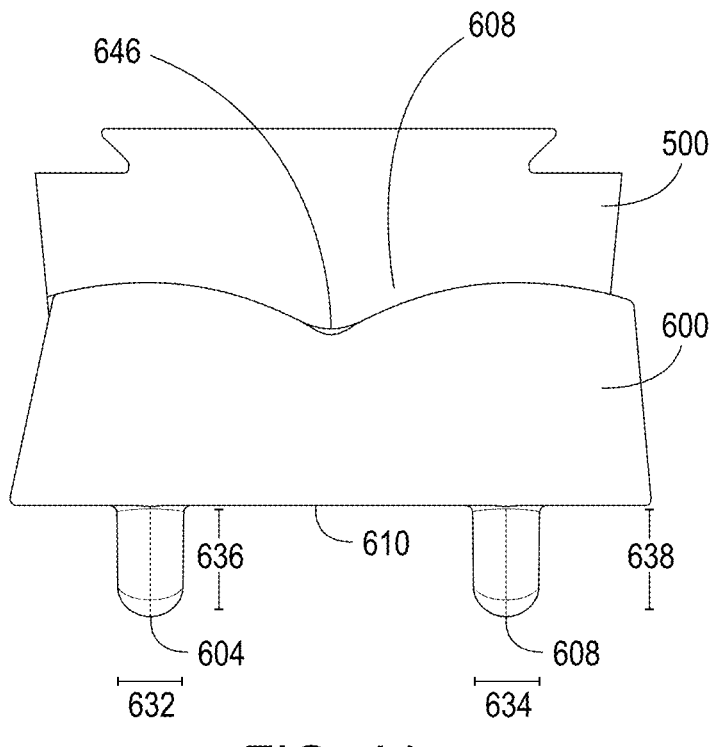
FIG. 44 is a front or rear view of an embodiment of a talar implant.
FIG. 45 is a sideview of an embodiment of a talar implant.
Figure 46B:
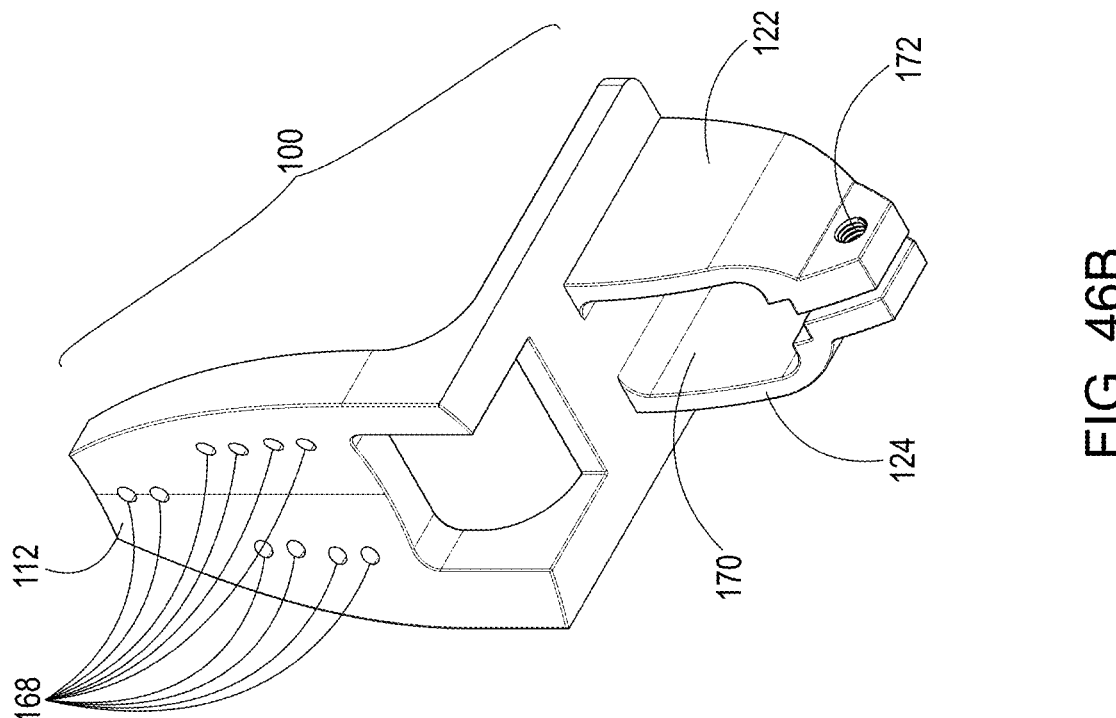
FIG. 46B is a perspective view of an embodiment of an adjustment mechanism.
Figure 46A:
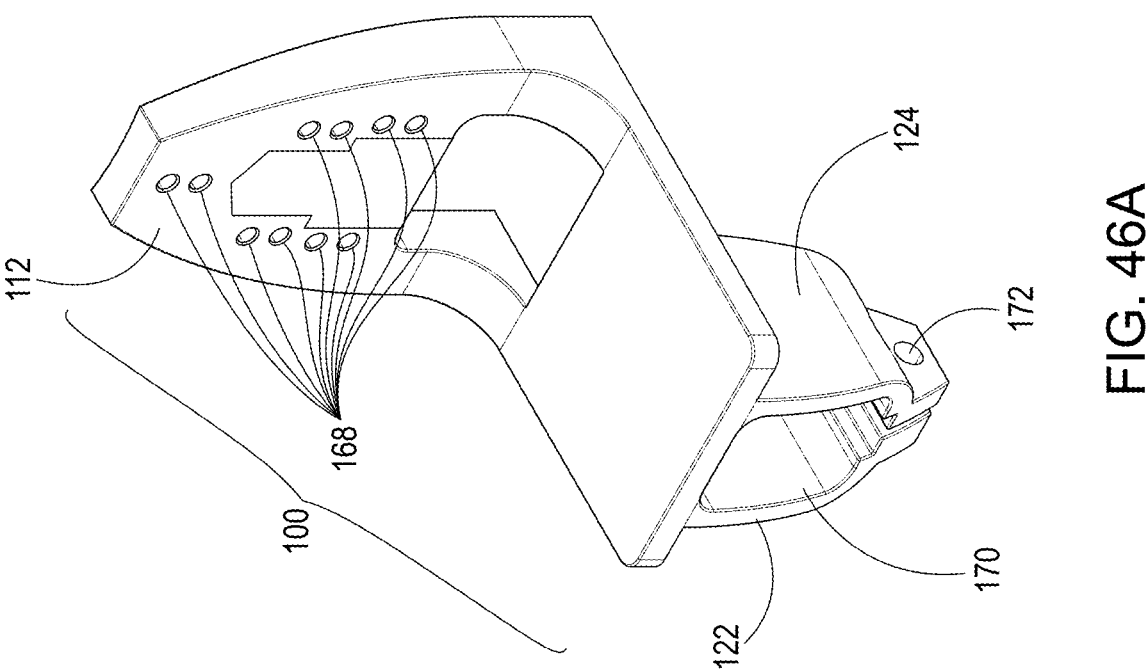
FIG. 46A is a perspective view of an embodiment of an adjustment mechanism.

In embodiments, as shown in FIGS. 44-45, the first keel 604 and the second keel 606 may include substantially trapezoidal cross-sections. In embodiments, the first keel 604 and the second keel 606 may include proximal keel lengths 612, 614 proximal to the body 640. The first keel 604 and the second keel 606 may include distal keel lengths 620, 622 distal to the body 640. In embodiments, the proximal keel lengths 612, 614 may be greater than the distal keel lengths 620, 622.

In embodiments, the first keel 604 and second keel 606 may include keel features (not shown). The keel features may include any suitable feature, including but not limited to textured surfaces, recesses, porous surfaces, and protrusions.

In embodiments, as shown in FIG. 45, at least one of the first keel 604 and second keel 606 may include cross-sectional keel openings 616, 618. The cross-sectional keel openings 616, 618 may be configured to traverse the entirety of the first keel width 632 and second keel width 634. In embodiments, the cross-sectional keel openings may include a shape selected from one of substantially trapezoidal cross-sections, oblong cross-sections, and non-circular cross-sections.

In embodiments, as shown in FIG. 45, the first keel 604 and second keel 606 may include a first keel arm 624 and second keel arm 626, respectively. In embodiments, the first keel arm 624 and second keel arm 626 may be disposed at the angle θ with respect to the inferior face 610 of the body 640.

In embodiments, as shown in FIG. 42-45, the talar implant 600 may include a peg 602. In embodiments, the peg 602 may include a substantially cylindrical shape 642 terminating in a substantially hemispherical shape 644. In embodiments, the peg 602 may be disposed at an angle θ with respect to the inferior face 610 of the body 640. The peg 602, first keel 604, and second keel 606 may be configured to be inserted into corresponding surfaces of a resected talus. The peg 602 may be disposed on an anterior side, posterior side, or lateral side of the inferior face 610. When the first keel 604 and second keel 606 are disposed on the anterior side of the inferior face 610, the peg 602 is disposed on the posterior side of the inferior face 610. In one embodiment, peg 602 is located approximately on a center line between first keel 604 and second keel 606. When the first keel 604 and second keel 606 are disposed on the posterior side of the inferior face 610, the peg 602 is disposed on the anterior side of the inferior face 610. When the first keel 604 and second keel 606 are disposed on a first lateral side of the inferior face 610, the peg 602 is disposed on an opposite lateral side of the inferior face 610.

In embodiments, as shown in FIG. 42-45, the body 640 may include a superior face 608. The superior face 608 may include a sulcus 656. In embodiments, a first artificial joint surface 500 may be configured to engage the superior face 608 of the body 640.

While the disclosure may be described herein, using a limited number of embodiments, these specific embodiments may be not intended to limit the scope of the disclosure as otherwise described and claimed herein. The precise arrangement of various elements and order of the steps of articles and methods described herein may be not to be considered limiting. For instance, although the steps of the methods may be described with reference to sequential series of reference signs and progression of the blocks in the FIGS., the method can be implemented in an order as desired.

The invention claimed is:

1. A surgical device comprising:
   a housing comprising:
      a longitudinal length disposed along a first axis;
      a width, and
      at least one location feature disposed on the longitudinal length;
   a reamer nested entirely within the housing and comprising a plurality of nested reamer elements comprising a first reamer element and a second reamer element nested within the first reamer element, the first reamer element and the second reamer element configured to telescope out of the housing; and
   an adjustment mechanism comprising:
      a first adjustment mechanism face disposed on a second axis and configured to contact an anterior surface of a patient's tibia; and
      wherein the adjustment mechanism is configured to be movably attached to the housing along the longitudinal length.

2. The surgical device of claim 1, wherein the first adjustment mechanism face is configured to contact the anterior surface of the patient's tibia when the adjustment mechanism is at a contact location along the longitudinal length, and wherein the at least one location feature is configured to determine the contact location.

3. The surgical device of claim 1 wherein the at least one location feature comprises an indicator along at least a portion of the width of the housing.

4. The surgical device of claim 1 wherein the reamer is oriented substantially perpendicularly to the longitudinal length of the housing.

5. The surgical device of claim 1, the housing further comprising a shaft oriented substantially parallel to the first axis, the housing comprising a patient distal end and a patient proximal end, wherein the shaft is configured to be engaged by a power driver at the patient distal end.

6. The surgical device of claim 5, the housing further comprising a first gear and a second gear, wherein the shaft is configured to engage the first gear at a first location within the housing disposed between the patient proximal end and the patient distal end;

wherein the second gear is configured to engage the first gear at a second location within the housing disposed between the patient proximal end and the first location and is configured to engage the reamer at a third location within the housing disposed between the patient proximal end and the second location;

wherein rotation of the shaft is configured to cause rotation of the first gear and the second gear;

wherein rotation of the first gear and the second gear is configured to cause rotation of the reamer; and wherein rotation of the reamer is configured to cause expansion of the plurality of nested reamer elements in a superior direction from the housing from a collapsed state into an expanded state.

7. The surgical device of claim 6, wherein the reamer comprises a first height in the collapsed state and a second height in the expanded state, wherein the second height is greater than the first height, and wherein a diameter along any portion of the reamer does not increase during expansion into the expanded state.

8. The surgical device of claim 6, wherein the surgical device further comprises a clutch coupled to the housing and the reamer, wherein the clutch is configured to control rotation of at least one of the shaft, the first gear, the second gear, and the reamer.

9. The surgical device of claim 1, wherein the plurality of nested reamer elements further comprises a head reamer element, at least one intermediate reamer element comprising leading faces comprising cutting teeth, and a base reamer element.

10. The surgical device of claim 9, wherein the head reamer element is disposed superior to all other of the plurality of nested reamer elements when in an expanded state and wherein the head reamer element is comprised and nested within an adjacent one of the plurality of nested reamer elements.

11. The surgical device of claim 1, wherein the plurality of nested reamer elements further comprises a third reamer element, wherein the second reamer element is threadably coupled to the first reamer element and the third reamer element is threadably coupled to the second reamer element, and wherein rotation of the shaft is configured to cause the first reamer element to rotate and expand in the superior direction relative to a second reamer element and the third reamer element.

12. The surgical device of claim 1, wherein the surgical device is configured to be connected to the patient's tibia using a plurality of pins.

13. The surgical device of claim 1, wherein the first reamer element further comprises an internal thread and an external thread and the second reamer element further comprises an internal thread and an external thread, wherein the external thread of the first reamer element is configured to threadingly engage the internal thread of the second reamer element.

14. The surgical device of claim 1, wherein the reamer further comprises at least one stop element configured to inhibit further advancement of at least one of the plurality of reamer elements in a superior direction beyond a certain expansion distance relative to an adjacent one of the plurality of nested reamer elements.

15. A method of orienting a reamer comprising:

providing the reamer comprising a plurality of nested reamer elements;

orienting the reamer within a housing, the housing comprising at least one location feature;

providing an adjustment mechanism comprising a first adjustment mechanism face configured to contact an anterior surface of a patient's tibia;

movably affixing the adjustment mechanism to the housing;

positioning the housing partially within a resected area of a patient's tibia joint based on a position of the at least one location feature of the housing with respect to the anterior surface of the patient's tibia;

sliding the adjustment mechanism along a longitudinal length of the housing until the first adjustment mechanism face contacts the anterior surface of the patient's tibia; and determining whether the adjustment mechanism, when contacting the anterior surface of the patient's tibia, aligns the reamer with an intramedullary canal of the patient's tibia.

16. The method of claim 15, wherein, when the adjustment mechanism is determined not to align with the intramedullary canal of patient's tibia, the method further comprising:

positioning the housing partially within the resected area of the patient's tibia joint based on a position of a second location feature of the housing with respect to the anterior surface of the patient's tibia; and determining whether the adjustment mechanism, when contacting the anterior surface of the patient's tibia, aligns the reamer with the intramedullary canal of the patient's tibia.

17. The method of claim 15, wherein, when the adjustment mechanism is determined to align the reamer with the intramedullary canal of the patient's tibia, further comprising locking the adjustment mechanism relative to the at least one location feature of the housing.

18. The method of claim 17, further comprising expanding the reamer, the housing further comprising a patient distal end and a patient proximal end and comprising a first gear and a second gear, wherein a shaft is configured to engage a power driver at the patient distal end and is configured to engage the first gear at a first location within the housing disposed between the patient proximal end and the patient distal end;

wherein the second gear is configured to engage the first gear at a second location within the housing disposed between the patient proximal end and the first location;

wherein rotation of the shaft causes rotation of the first gear and the second gear;

wherein rotation of the first gear and the second gear causes rotation of the reamer; and wherein rotation of the reamer cause expansion of the plurality of nested reamer elements.

19. The method of claim 18, wherein the plurality of nested reamer elements further comprises a head reamer element, at least one intermediate reamer element, and a base reamer element, the head reamer element and the at least one intermediate reamer element further comprising leading faces comprising cutting teeth.

20. The method of claim 15, wherein the surgical device is configured to be connected to the patient's tibia using a plurality of pins.

* * * * *